(12) United States Patent
Tsuboi et al.

(10) Patent No.: US 8,471,038 B2
(45) Date of Patent: Jun. 25, 2013

(54) BICYCLIC HETEROCYCLIC COMPOUND

(75) Inventors: Katsunori Tsuboi, Suita (JP); Yusuke Yamai, Suita (JP); Hitoshi Watanabe, Suita (JP); Hironori Kinoshita, Suita (JP)

(73) Assignee: Dainippon Sumitomo Pharma Co., Ltd., Osaka-shi (JP)

( * ) Notice: Subject to any disclaimer, the term of this patent is extended or adjusted under 35 U.S.C. 154(b) by 0 days.

(21) Appl. No.: 13/141,301

(22) PCT Filed: Dec. 25, 2009

(86) PCT No.: PCT/JP2009/071529
§ 371 (c)(1),
(2), (4) Date: Aug. 17, 2011

(87) PCT Pub. No.: WO2010/074193
PCT Pub. Date: Jul. 1, 2010

(65) Prior Publication Data
US 2011/0294804 A1    Dec. 1, 2011

(30) Foreign Application Priority Data
Dec. 26, 2008    (JP) .................................. 2008-332796

(51) Int. Cl.
*A61K 31/4184* (2006.01)
*C07D 235/14* (2006.01)

(52) U.S. Cl.
USPC ........ 548/309.7; 546/118; 544/139; 544/370; 548/304.7; 514/234.5; 514/254.06; 514/394; 514/303

(58) Field of Classification Search
USPC ...................................................... 548/309.7
See application file for complete search history.

(56) References Cited

FOREIGN PATENT DOCUMENTS
| | | |
|---|---|---|
| WO | WO 02/28839 A1 | 4/2002 |
| WO | WO 02/42278 A2 | 5/2002 |
| WO | WO 2008-033739 A2 | 3/2008 |
| WO | WO 2009/079011 A1 | 6/2009 |

OTHER PUBLICATIONS

Barten et al., Drug Design, Development and Therapy (2010), vol. 4, pp. 343-366.*
Akopian et al., *Nature*, 379: 257-262 (1996).
Rabert et al., *Pain*, 78: 107-114 (1998).
Renganathan et al., *Brain Research*, 959: 235-242 (2003).
Yoshimura et al., *Urology*, 57 (Suppl. 6A): 116-117 (2001).
Japanese Patent Office, International Search Report in International Patent Application No. PCT/JP2009/071529 (Feb. 2, 2010).
European Patent Office, Extended European Search Report in European Patent Application No. 09834989.7 (Dec. 7, 2012).

* cited by examiner

*Primary Examiner* — Laura L. Stockton
(74) *Attorney, Agent, or Firm* — Leydig, Voit & Mayer, Ltd.

(57) ABSTRACT

The invention provides a compound for the treatment or prophylaxis of pathology involving SNS, specifically diseases such as neuropathic pain, nociceptive pain, dysuria, multiple sclerosis and the like. The compound is represented by formula (1) or a pharmaceutically acceptable salt thereof wherein $R^1$ is a hydrogen atom or the like, L is a single bond, —O— or the like, $R^2$ is a phenyl group or the like, X is a carbon atom or a nitrogen atom, and $R^3$, $R^4$, $R^{5a}$, $R^{5b}$, $R^6$ and $R^7$ are each independently a substituted or unsubstituted alkyl group or the like:

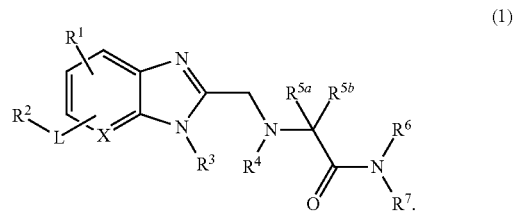

(1)

40 Claims, No Drawings

BICYCLIC HETEROCYCLIC COMPOUND

TECHNICAL FIELD

The present invention relates to a drug for the treatment or prophylaxis of pathology in general in which SNS (sensory neuron specific sodium channel) is involved, which comprises a novel compound having a benzimidazole or imidazopyridine skeleton as a bicyclic heterocycle or a pharmaceutically acceptable salt thereof as an active ingredient. Specifically, the present invention relates to a drug for the treatment or prophylaxis of diseases such as neuropathic pain, nociceptive pain, dysuria, multiple sclerosis and the like.

BACKGROUND ART

In 1952, Hodgkin and Huxley showed that the main body of neural activity is an Na channel, after which Na channel blockers have been developed as antiarrhythmic or topical anesthetics. In 1961, lidocain, which is one of the Na channel blockers, was found to provide an analgesic effect, and clinical application thereof as an analgesic was started. However, since Na channel is also present in nonneural tissues such as muscle, heart and the like, side effects by systemic administration remained as a problem.

With the advance of molecular biology, subtypes of Na channel have been elucidated one after another, and Na channel α subunit that forms pore is known to include 10 kinds at present. A sensory neuron specific sodium channel (sensory nerve-specific Na channel), i.e., SNS, is one of such Na channel α subunits, is a tetrodotoxin (TTX)-resistant Na channel localized in the small diameter cell (C fiber) of dorsal root ganglion involved in nerval perception, and is also called SCN10A, PN3 or NaV1.8 (non-patent documents 1, 2). It has been reported that SNS knockout mouse is insensitive to mechanical stimulations, and administration of antisense to SNS to neuropathic pain or inflammatory pain models attenuates hypersensitivity and abnormal perception.

Therefore, an SNS inhibitor is considered to provide a therapeutic or prophylactic drug showing an analgesic effect for diseases such as neuropathic pain, nociceptive pain and the like, which accompany pain, numbness, burning sensation, dull pain and the like, each involving C fiber. Moreover, since SNS is not expressed in nonneural tissues and central nervous system, a medicament that selectively inhibits SNS is considered to be a medicament free of side effects derived from nonneural tissues or central nervous system.

In dysuria, moreover, it has been clarified that frequent urination, its main symptom, is caused by overactivity of the C fiber; in other words, dysfunction of afferent sensory nervous pathway from the lower urinary tract is involved in overactive bladder and cystalgia, and suppression of C fiber sensory nerve from the bladder is effective thereon (non-patent document 3). Therefore, a medicament that inhibits SNS mainly causing the neural activity of C fiber is expected to be a therapeutic or prophylactic drug for dysuria, which has a novel point of action.

On the other hand, a recent report has documented that SNS found only in C fiber is ectopically expressed in cerebellar Purkinje cell of multiple sclerosis patients, and is involved in the occurrence of an abnormal firing pattern in the cerebellum (non-patent document 4). As such, an SNS inhibitor is expected to be a first therapeutic or prophylactic drug toward the induction of symptoms caused by abnormal firing associated with SNS expression in the cerebellar neuron, such as ataxia and the like in multiple sclerosis.

The following shows the actual treatment state of the aforementioned diseases in clinical practice.

(1) Neuropathic Pain

Neuropathic pain refers to a pain including spontaneous pain and chronic pain developed by nerve damage or nerve stimulation even when trauma is absent and tissue inflammation is absent after complete recovery. Examples thereof include neuralgia after lumbar operation, diabetic neuropathy, neuralgia after herpes zoster, reflex sympathetic dystrophy, phantom limb pain, spinal cord damage, late stage carcinomatous pain, and prolonged postoperative pain. NSAIDS (non-steroidal anti-inflammatory drugs) such as aspirin and the like are completely ineffective for neuropathic pain, and opioids such as morphine and the like are problematic in drug resistance and induction of psychological symptom.

At present, a sole medicament in the market, which is allegedly effective for neuropathic pain, is mexiletine applicable to diabetic neuropathy. Since mexiletine does not have selectivity to Na channel, though it provides an analgesis effect, side effects are feared and administration at a high dose has been reported to be unavailable. Some other medicaments are clinically applied as aids. Examples thereof include antidepressant (sulpiride, trazodone, fluvoxatine, milnacipran), adrenaline agonist (clonidine, dexmedetomidine), NMDA receptor antagonists (ketamine hydrochloride, dextromethorphan), antianxiety drug (diazepam, lorazepam, etizolam, hydroxyzine hydrochloride), anticonvulsant (carbamazepine, phenyloin, sodium valproate, zonisamide), calcium antagonist (nifedipine, verapamil hydrochloride, lomerizine hydrochloride) and the like, all of which are used as aids. From the above, a therapeutic drug free of side effects derived from nonneural tissue or central nervous system and specifically effective for pain is desired.

(2) Nociceptive Pain

Nociceptive pain refers to a pain caused by the activation of nociceptor (Aδ, C fiber) by mechanical, hyperthermic or chemical noxious stimulation due to tissue injury and the like. Nociceptor is sensitized by endogenous chemical stimulation (algetic substance) such as serotonin, substance P, bradykinin, prostaglandin and histamine. Examples of the nociceptive pain include lumbago, abdominal pain, and pain due to rheumatoid arthritis or osteoarthritis. In clinical practice, NSAIDS (acetylsalicylic acid, acetaminophen, diclofenac sodium, indomethacin, mofezolac, flurbiprofen, loxoprofen sodium, ampiroxicam), steroid drugs (prednisolone, methylprednisolone, dexamethasone, betamethasone), $PGE_1$ (prostaglandin E1) (alprostadil, lipo alprostadil, limaprost alprostadil) and $PGI_2$ (beraprost sodium) are used.

(3) Dysuria (Urinary Disturbance)

Dysuria is a disease mainly showing urinary frequency, urorrhea, feeling of residual urine and urodynia as main symptoms. At present, the main drug treatment of overactive bladder uses a muscarinic receptor inhibitor that suppresses the bladder parasympathetic nerve pathway. However, its limitation has also been clarified. Capsaicin and resinifera toxin, which are vanilloid receptor stimulants, have been reported to specifically act on C fiber to suppress its function. However, a medicament that acts on SNS localized in C fiber has not been found.

(4) Multiple Sclerosis

Multiple sclerosis is one kind of demyelination diseases, which shows scattered foci of demyelination in the white matter of the central nervous system, with various old and new lesions. The lesions appear more commonly in the white matter of lateral cerebral ventricle periphery, optic nerve, brain stem, spinal cord and the like. Histologically, myelin sheath is destroyed and axon and nerve cell are not damaged.

As clinical symptoms, symptoms such as optic neuritis, double vision, eyeball motion impairments such as nystagmus, convulsive paralysis, painful tonic convulsive attack, Lhermitte's syndrome, ataxia, logopathy, bladder rectal disorder and the like appear in various combinations. The etiology thereof is unknown, though autoimmune disease theory, infection theory and the like are proposed. At present, an effective prophylactic or therapeutic drug for multiple sclerosis is highly desired.

Patent document 1 to be mentioned later relates to a selective modulator of CRF1 receptor and specifically describes a compound represented by the following formula (A) (Example 5, k). The compounds encompassed in the patent document characteristically have an amide bond in methylene on the imidazole ring, and are different from the compound of the present invention having an amino group in methylene on the imidazole ring. In addition, patent document 1 does not at all contain a description suggesting the present invention.

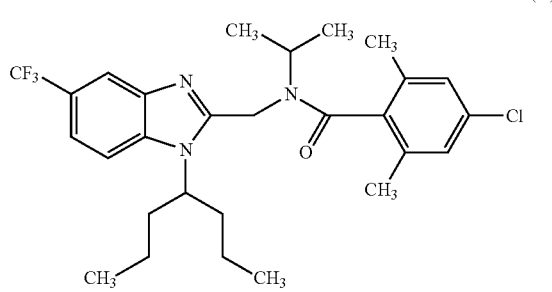

(A)

Patent document 2 to be mentioned later relates to a Rho kinase inhibitor, and specifically describes a compound represented by the following formula (B) (Example 321). The compounds encompassed in the patent document do not have a substituent on the nitrogen atom of imidazole ring, and are different from the compound of the present invention essential having the substituent. In addition, patent document 2 does not at all contain a description suggesting the present invention.

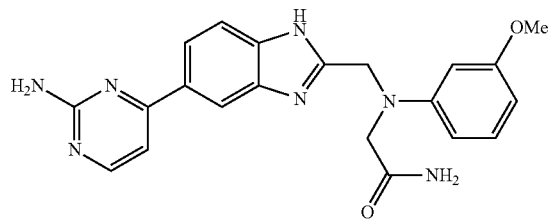

(B)

DOCUMENT LIST

Patent Document

Patent Document 1: WO 02/28839
Patent Document 2: WO 2009/79011

Non-Patent Document non-Patent Document 1: Nature 379: 257, 1996
non-Patent Document 2: Pain 78: 107, 1998
non-Patent Document 3: Urology 57: 116, 2001
non-Patent Document 4: Brain Research 959: 235, 2003

SUMMARY OF THE INVENTION

Problems to be Solved by the Invention

The problem of the present invention is to provide a drug for the prophylaxis or treatment of pathology in general in which SNS is involved, specifically, diseases such as neuropathic pain, nociceptive pain, dysuria, multiple sclerosis and the like.

Means of Solving the Problems

The present inventors have conducted intensive studies in an attempt to solve the aforementioned problem and found that a bicyclic compound having an imidazole ring or a pharmaceutically acceptable salt thereof inhibits TTX resistant Na channel in human SNS gene expressing cell, namely, has an SNS inhibitory activity, and is useful as a therapeutic or prophylactic drug for diseases such as a neuropathic pain, a nociceptive pain, dysuria, multiple sclerosis and the like, which resulted in the completion of the present invention.

Accordingly, the present invention provides the following.
[1] a compound represented by the following formula (1) or a pharmaceutically acceptable salt thereof (hereinafter sometimes referred to as "the compound of the present invention"):
a compound represented by

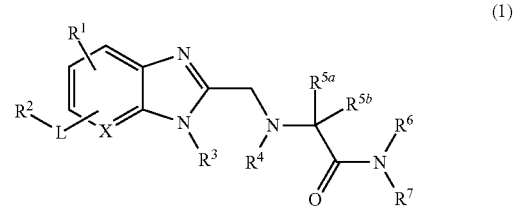

(1)

wherein
$R^1$ is a hydrogen atom, a halogen atom, an alkyl group having 1 to 6 carbon atoms, a haloalkyl group having 1 to 6 carbon atoms, an alkoxy group having 1 to 6 carbon atoms or a haloalkoxy group having 1 to 6 carbon atoms ($R^1$ can substitute the benzene ring or pyridine ring at any substitutable position thereon),
L is a single bond, —O— or —CH$_2$O— (L can substitute the benzene ring or pyridine ring at any substitutable position thereon),
$R^2$ is a substituted or unsubstituted 6- to 10-membered aryl group, or a substituted or unsubstituted 5- to 10-membered aromatic heterocyclic group,
X is a carbon atom or a nitrogen atom,
$R^3$ is a substituted or unsubstituted alkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, or a substituted or unsubstituted 5- to 10-membered unsaturated aliphatic heterocyclic group,
$R^4$ is a hydrogen atom, a substituted or unsubstituted alkyl group having 1 to 6 carbon atoms, or a substituted or unsubstituted 3- to 8-membered cycloalkyl group, $R^{5a}$ and $R^{5b}$ are each independently a hydrogen atom, or a substituted or unsubstituted alkyl group having 1 to 6 carbon atoms, or $R^4$ and $R^{5a}$ are optionally bonded to form, together with the nitrogen atom that $R^4$ is bonded to, a 4- to 8-membered saturated nitrogen-containing aliphatic heterocycle (in this case, $R^{5b}$ is a hydrogen atom), $R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, a substituted or unsubstituted 5- to 10-membered unsaturated aliphatic heterocyclic group, a substituted or unsubstituted 6- to 10-membered aryl group, or a substituted or unsubstituted 5- to 10-membered aromatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms)

(hereinafter sometimes referred to as "compound (1)") or a pharmaceutically acceptable salt thereof;

[2] the compound of [1], which is represented by the following formula (2):

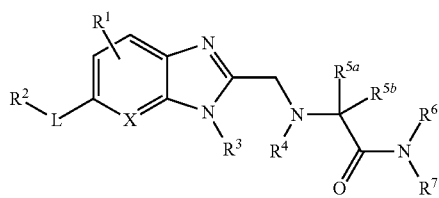

(2)

wherein $R^1$, $R^2$, $R^3$, $R^4$, $R^{5a}$, $R^{5b}$, $R^6$, $R^7$, L and X are as defined in [1] (hereinafter sometimes referred to as "compound (2)") or a pharmaceutically acceptable salt thereof;

[3] the compound of [1], which is represented by the following formula (3):

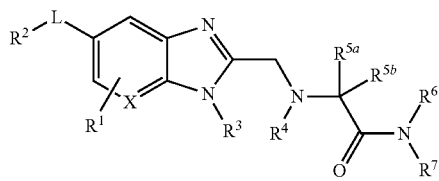

(3)

wherein $R^1$, $R^2$, $R^3$, $R^4$, $R^{5a}$, $R^{5b}$, $R^6$, $R^7$, L and X are as defined in [1] (hereinafter sometimes referred to as "compound (3)") or a pharmaceutically acceptable salt thereof;

[4] the compound of any one of [1] to [3], wherein $R^2$ is a substituted or unsubstituted phenyl group, or a pharmaceutically acceptable salt thereof;

[5] the compound of any one of [1] to [4], wherein $R^3$ is a substituted or unsubstituted alkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, or a pharmaceutically acceptable salt thereof;

[6] the compound of any one of [1] to [5], wherein $R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms), or a pharmaceutically acceptable salt thereof;

[7] the compound of any one of [1] to [6], wherein $R^4$ is a hydrogen atom, or a substituted or unsubstituted alkyl group having 1 to 6 carbon atoms, or a pharmaceutically acceptable salt thereof;

[8] the compound of any one of [1] to [7], wherein $R^{5a}$ and $R^{5b}$ are each independently a hydrogen atom, or a substituted or unsubstituted alkyl group having 1 to 6 carbon atoms, or a pharmaceutically acceptable salt thereof;

[9] the compound of any one of [1] to [8], wherein X is a carbon atom, or a pharmaceutically acceptable salt thereof;

[10] the compound of any one of [1] to [9], wherein $R^1$ is a hydrogen atom or a halogen atom, or a pharmaceutically acceptable salt thereof;

[11] the compound of any one of [1] to [10], wherein L is a single bond, or a pharmaceutically acceptable salt thereof;

[12] the compound of any one of [1] to [10], wherein L is —O—, or a pharmaceutically acceptable salt thereof;

[13] the compound of any one of [1] to [10], wherein L is —CH$_2$O—, or a pharmaceutically acceptable salt thereof;

[14] $N^2$-{[1-(2-ethoxyethyl)-6-(4-fluorophenoxy)-1H-benzimidazol-2-yl]methyl}glycinamide, $N^2$-{[1-(2-ethoxyethyl)-6-(4-fluorophenoxy)-1H-benzimidazol-2-yl]methyl}-2-methylalaninamide, $N^2$-{[1-cyclopropyl-6-(4-fluorophenoxy)-1H-benzimidazol-2-yl]methyl}-L-alaninamide, $N^2$-{[1-cyclobutyl-6-(4-fluorophenoxy)-1H-benzimidazol-2-yl]methyl}-L-alaninamide, $N^2$-{[6-(4-chlorophenoxy)-1-(2-ethoxyethyl)-1H-benzimidazol-2-yl]methyl}-L-alaninamide, $N^2$-{[6-(4-fluorophenoxy)-1-(2-hydroxy-2-methylpropyl)-1H-benzimidazol-2-yl]methyl}-L-alaninamide, $N^2$-{[1-(2-ethoxyethyl)-6-(4-fluorophenoxy)-1H-benzimidazol-2-yl]methyl}-L-alaninamide, $N^2$-{[6-(4-fluorophenoxy)-1-(3-methoxypropyl)-1H-benzimidazol-2-yl]methyl}-L-alaninamide, $N^2$-{[6-(2-chloro-4-fluorophenoxy)-1-(2-ethoxyethyl)-1H-benzimidazol-2-yl]methyl}-L-alaninamide, $N^2$-{[1-ethyl-6-(4-methylphenoxy)-1H-benzimidazol-2-yl]methyl}-L-alaninamide, $N^2$-{[6-(2,4-difluorophenoxy)-1-(2-hydroxy-2-methylpropyl)-1H-benzimidazol-2-yl]methyl}-L-alaninamide, $N^2$-{[1-(2-ethoxyethyl)-5-fluoro-6-(4-fluorophenyl)-1H-benzimidazol-2-yl]methyl}-L-alaninamide, N²-{[1-ethyl-5-fluoro-6-(4-fluorophenyl)-1H-benzimidazol-2-yl]methyl}-L-alaninamide, N²-{[1-(3-methoxypropyl)-6-(4-methylphenoxy)-1H-benzimidazol-2-yl]methyl}-L-alaninamide, N²-{[6-(4-methylphenoxy)-1-(tetrahydro-2H-pyran-4-yl)-1H-benzimidazol-2-yl]methyl}-L-alaninamide, N²-{[5-chloro-1-(2-ethoxyethyl)-6-(4-fluorophenyl)-1H-benzimidazol-2-yl]methyl}-L-alaninamide, or N²-{[5-chloro-6-(3,4-difluorophenyl)-1-(2-ethoxyethyl)-1H-benzimidazol-2-yl]methyl}-L-alaninamide, or a pharmaceutically acceptable salt thereof;

[15] a medicament comprising the compound of any one of [1] to [14] or a pharmaceutically acceptable salt thereof as an active ingredient;

[16] the medicament of [15], which is an agent for the prophylaxis or treatment of neuropathic pain, nociceptive pain, dysuria or multiple sclerosis;

[17] a SNS inhibitor comprising the compound of any one of [1] to [14] or a pharmaceutically acceptable salt thereof as an active ingredient;

[18] a pharmaceutical composition comprising the compound of any one of [1] to [14] or a pharmaceutically acceptable salt thereof, and a pharmaceutically acceptable carrier.

Effect of the Invention

The present invention provides an SNS inhibitor comprising a novel bicyclic compound or a pharmaceutically acceptable salt thereof. The SNS inhibitor of the present invention is useful as a drug for the treatment or prophylaxis of pathology in general in which SNS is involved, and is specifically applicable to patients with neuropathic pain, nociceptive pain, dysuria, multiple sclerosis and the like.

DESCRIPTION OF EMBODIMENTS

In the present specification, examples of the "halogen atom" include a fluorine atom, a chlorine atom, a bromine atom and an iodine atom.

The "alkyl group" means a straight chain or branched alkyl group having 1 to 6 carbon atoms, and specific examples thereof include methyl group, ethyl group, propyl group (1-propyl group), isopropyl group (2-propyl group), butyl group (1-butyl group), sec-butyl group (2-butyl group), isobutyl group (2-methyl-1-propyl group), tert-butyl group (2-methyl-2-propyl group), pentyl group (1-pentyl group), hexyl group (1-hexyl group) and the like. The alkyl group is preferably an alkyl group having 1 to 4 carbon atoms.

The "haloalkyl group" means a straight chain or branched alkyl group having 1 to 6 carbon atoms, which is substituted by the same or different 1 to 5 halogen atoms, and specific examples thereof include trifluoromethyl group, 2,2-difluoroethyl group, 2,2,2-trifluoroethyl group, 2-chloroethyl group, pentafluoroethyl group, 3,3,3-trifluoropropyl group and the like. The haloalkyl group is preferably a haloalkyl group alkyl group having 1 to 4 carbon atoms.

The "alkenyl group" means a straight chain or branched alkenyl group having 2 to 6 carbon atoms, and specific examples thereof include vinyl group, 1-propenyl group, 2-propenyl group, 1-methylvinyl group, 1-butenyl group, 1-ethylvinyl group, 1-methyl-2-propenyl group, 2-butenyl group, 3-butenyl group, 2-methyl-1-propenyl group, 2-methyl-2-propenyl group, 1-pentenyl group, 1-hexenyl group and the like. The alkenyl group is preferably an alkenyl group having 2 to 4 carbon atoms.

The "alkynyl group" means a straight chain or branched alkynyl group having 2 to 6 carbon atoms, and specific examples thereof include ethynyl group, 1-propynyl group, 2-propynyl group, 1-butynyl group, 1-methyl-2-propynyl group, 3-butynyl group, 1-pentynyl group, 1-hexynyl group and the like. The alkynyl group is preferably an alkynyl group having 2 to 4 carbon atoms.

The "alkoxy group" means a straight chain or branched alkoxy group having 1 to 6 carbon atoms, and specific examples thereof include methoxy group, ethoxy group, propoxy group, 1-methylethoxy group, butoxy group, 1-methylpropoxy group, 2-methylpropoxy group, 1,1-dimethylethoxy group, pentyloxy group, hexyloxy group and the like. The alkoxy group is preferably an alkoxy group having 1 to 4 carbon atoms.

The "haloalkoxy group" means a straight chain or branched alkoxy group having 1 to 6 carbon atoms, which is substituted by the same or different 1 to 5 halogen atoms, and specific examples thereof include trifluoromethoxy group, 2,2-difluoroethoxy group, 2,2,2-trifluoroethoxy group, 2-chloroethoxy group, pentafluoroethoxy group, 3,3,3-trifluoropropoxy group and the like. The haloalkoxy group is preferably a haloalkoxy group having 1 to 4 carbon atoms.

The "cycloalkyl group" means a 3- to 8-membered monocyclic or bicyclic cycloalkyl group, and specific examples thereof include cyclopropyl group, cyclobutyl group, cyclopentyl group, cyclohexyl group, cycloheptyl group, cyclooctyl group and the like. The cycloalkyl group is preferably a 4- to 6-membered cycloalkyl group.

The "cycloalkenyl group" means a 4- to 8-membered monocyclic or bicyclic cycloalkenyl group, and specific examples thereof include cyclobutenyl group, cyclopentenyl group, cyclohexenyl group, cycloheptenyl group and cyclooctenyl group. The position of double bond on the ring is not particularly limited. The cycloalkenyl group is preferably a 5- or 6-membered cycloalkenyl group.

The "saturated aliphatic heterocyclic group" means a O-5 to 8-membered monocyclic or bicyclic saturated aliphatic heterocyclic group containing 1 to 3 hetero atoms selected from a nitrogen atom, an oxygen atom and a sulfur atom (provided that the numbers of the oxygen atom and sulfur atom contained in the saturated aliphatic heterocycle are each up to 2). The position of the hetero atom is not particularly limited as long as the saturated aliphatic heterocyclic group is chemically stable. Specific examples thereof include azetidinyl group, pyrrolidinyl group, piperidyl group, piperidino group, piperazinyl group, azepanyl group, azocanyl group, tetrahydrofuryl group, tetrahydrothienyl group, tetrahydropyranyl group, morpholinyl group, morpholino group, thiomorpholinyl group, 1,4-dioxanyl group, 1,2,5-thiadiazinyl group, 1,4-oxazepanyl group, 1,4-diazepanyl group and the like.

The "unsaturated aliphatic heterocyclic group" means a 5- to 10-membered monocyclic or bicyclic unsaturated aliphatic heterocyclic group containing 1 to 3 double bonds and 1 to 3 hetero atoms selected from a nitrogen atom, an oxygen atom and a sulfur atom (provided that the numbers of the oxygen atom and sulfur atom contained in the unsaturated aliphatic heterocycle are each up to 2). The positions of the hetero atom and double bond are not particularly limited as long as the unsaturated aliphatic heterocyclic group is chemically stable. Specific examples thereof include pyrrolinyl group, imidazolinyl group, tetrahydroisoquinolyl group and the like, and 2-pyrrolinyl group and 2-imidazolinyl group are preferable.

The "saturated nitrogen-containing aliphatic heterocycle" means a 4- to 8-membered monocyclic or bicyclic saturated aliphatic heterocycle containing at least one nitrogen atom and optionally further containing 1 to 3 hetero atoms selected from a nitrogen atom, an oxygen atom and a sulfur atom (provided that the numbers of the oxygen atom and sulfur atom contained in the saturated aliphatic heterocycle are each up to 2). The position of the hetero atom is not particularly limited as long as the saturated nitrogen-containing aliphatic heterocycle is chemically stable. Specific examples thereof include azetidine ring, pyrrolidine ring, imidazolidine ring, pyrazolidine ring, piperidine ring, piperazine ring, azepane ring, azocane ring, morpholine ring, thiomorpholine ring, oxazolidine ring, thiazolidine ring and the like.

The "unsaturated nitrogen-containing aliphatic heterocycle" means a 4- to 8-membered monocyclic or bicyclic unsaturated aliphatic heterocycle containing at least one nitrogen atom and optionally further containing 1 to 3 hetero atoms selected from a nitrogen atom, an oxygen atom and a sulfur atom (provided that the numbers of the oxygen atom and sulfur atom contained in the unsaturated aliphatic heterocycle are each up to 2). The position of the hetero atom is not particularly limited as long as the unsaturated nitrogen-containing aliphatic heterocycle is chemically stable. Specific examples thereof include pyrroline ring, piperidine ring, imidazoline ring, pyrazoline ring, oxazoline ring, thiazoline ring, tetrahydroquinoline ring, tetrahydroisoquinoline ring and the like.

The "aryl group" means a 6- to 10-membered monocyclic or bicyclic aryl group, and specific examples thereof include phenyl group, 1-naphthyl group, 2-naphthyl group and the like.

The "aromatic heterocyclic group" means a 5- to 10-membered monocyclic or bicyclic aromatic heterocyclic group containing 1 to 4 hetero atoms selected from a nitrogen atom, an oxygen atom and a sulfur atom (provided that the numbers of the oxygen atom and sulfur atom contained in the aromatic heterocyclic group are each up to 2). The position of the hetero atom is not particularly limited as long as the aromatic heterocyclic group is chemically stable. Specific examples thereof include furyl group, thienyl group, pyrrolyl group, oxazolyl group, isoxazolyl group, thiazolyl group, isothiazolyl group, imidazolyl group, pyrazolyl group, furazanyl group, oxadiazolyl group, triazolyl group, pyridyl group, pyrimidinyl group, pyrazinyl group, indolyl group, quinolyl group, isoquinolyl group, quinazolinyl group, imidazo[2,1-b][1,3]thiazolyl group and the like.

The "alkylthio group" means a straight chain or branched alkylthio group having 1 to 6 carbon atoms, and specific examples thereof include methylthio group, ethylthio group, propylthio group, 1-methylethylthio group, butylthio group, 1-methylpropylthio group, 2-methylpropylthio group, 1,1-dimethylethylthio group, pentylthio group, hexylthio group and the like. The alkylthio group is preferably an alkylthio group having 1 to 4 carbon atoms.

Examples of the alkyl of the "alkylcarbonyl group" include those similar to the aforementioned alkyl group. Preferable examples of the alkylcarbonyl group include acetyl group, propionyl group, butyryl group and the like.

The "alkylcarbonyloxy group" means a group wherein the oxygen atom is bonded to the carbonyl carbon of the aforementioned "alkylcarbonyl group".

Examples of the alkyl of the "alkylsulfonyl group" include those similar to the aforementioned "alkyl group". Preferable examples of the alkylsulfonyl group include methylsulfonyl group, ethylsulfonyl group, propylsulfonyl group and the like.

Examples of the alkoxy of the "alkoxycarbonyl group" include those similar to the aforementioned "alkoxy group". Preferable examples of the alkoxycarbonyl group include methoxycarbonyl group, ethoxycarbonyl group, propoxycarbonyl group, butoxycarbonyl group, tert-butoxycarbonyl group and the like.

Examples of the alkyl group of the "amino group optionally substituted by one alkyl group or the same or different two alkyl groups", "carbamoyl group optionally substituted by one alkyl group or the same or different two alkyl groups" and "sulfamoyl group optionally substituted by one alkyl group or the same or different two alkyl groups" include those similar to the aforementioned "alkyl group".

Preferable examples of the "amino group optionally substituted by one alkyl group or the same or different two alkyl groups" include methylamino group, ethylamino group, propylamino group, dimethylamino group, diethylamino group, methylethylamino group and the like.

Preferable examples of the "carbamoyl group optionally substituted by one alkyl group or the same or different two alkyl groups" include methylcarbamoyl group, ethylcarbamoyl group, propylcarbamoyl group, isopropylcarbamoyl group, dimethylcarbamoyl group, diethylcarbamoyl group, methylethylcarbamoyl group and the like.

Preferable examples of the "sulfamoyl group optionally substituted by one alkyl group or the same or different two alkyl groups" include methylsulfamoyl group, ethylsulfamoyl group, propylsulfamoyl group, dimethylsulfamoyl group, diethylsulfamoyl group, methylethylsulfamoyl group and the like.

Examples of the "alkoxycarbonyl group" of the "amidino group optionally substituted by one alkoxycarbonyl group or the same or different two alkoxycarbonyl groups" include those similar to the aforementioned "alkoxycarbonyl group". Preferable examples of the "amidino group optionally substituted by one alkoxycarbonyl group or the same or different two alkoxycarbonyl groups" include methoxycarbonylamidino group, ethoxycarbonylamidino group, propoxycarbonylamidino group and the like.

The aryl group of the "aryloxy group", "arylcarbonyl group" and "arylsulfonyl group" is as defined for the aforementioned "aryl group".

The aromatic heterocyclic group of the "aromatic heterocyclyloxy group", "aromatic heterocyclylcarbonyl group" and "aromatic heterocyclylsulfonyl group" is as defined for the aforementioned "aromatic heterocyclic group".

The substituent for the "alkyl group", "alkenyl group" and "alkynyl group" is selected from the group consisting of the following (i) to (v), and the same or different plural substituents may be present:
(i) a halogen atom, a hydroxyl group, a carboxyl group and a cyano group;
(ii) a substituted or unsubstituted amino group, a substituted or unsubstituted carbamoyl group, and a substituted or unsubstituted sulfamoyl group;
(iii) an alkoxy group, a haloalkoxy group, an alkylcarbonyl group, an alkylcarbonyloxy group, an alkoxycarbonyl group, an alkylthio group and an alkylsulfonyl group
[these groups are optionally substituted by one or more substituents selected from a halogen atom, a hydroxyl group, a carboxyl group, an amino group optionally substituted by one alkyl group or the same or different two alkyl groups, an alkoxy group, a haloalkoxy group, an alkoxycarbonyl group, an optionally substituted aryl group and an optionally substituted aromatic heterocyclic group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];

(iv) a cycloalkyl group, a cycloalkenyl group, and a saturated or unsaturated aliphatic heterocyclic group
[these groups are optionally substituted by one or more substituents selected from a halogen atom, a hydroxyl group, a carboxyl group, an oxo group, a thioxo group, an amino group optionally substituted by one alkyl group or the same or different two alkyl groups, a carbamoyl group optionally substituted by one alkyl group or the same or different two alkyl groups, an alkoxy group, a haloalkoxy group, an optionally substituted alkoxycarbonyl group, an optionally substituted alkylcarbonyl group, an optionally substituted alkylsulfonyl group, an optionally substituted alkyl group, an optionally substituted aryl group and an optionally substituted aromatic heterocyclic group. Examples of the substituent for the alkoxycarbonyl group, alkylcarbonyl group, alkylsulfonyl group and alkyl group include a halogen atom, a hydroxyl group, a carboxyl group, an alkoxy group, a haloalkoxy group and a carbamoyl group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];
(v) an aryl group, an aromatic heterocyclic group, an aryloxy group, an aromatic heterocyclyloxy group, an arylcarbonyl group, an aromatic heterocyclylcarbonyl group, an arylsulfonyl group and an aromatic heterocyclylsulfonyl group
[these groups are optionally substituted by one or more substituents selected from a halogen atom, a hydroxyl group, a carboxyl group, a substituted or unsubstituted amino group, a substituted or unsubstituted carbamoyl group, a substituted or unsubstituted sulfamoyl group, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group].

The substituent for the "cycloalkyl group", "cycloalkenyl group", "saturated aliphatic heterocyclic group", "unsaturated aliphatic heterocyclic group", "saturated nitrogen-containing aliphatic heterocycle" and "unsaturated nitrogen-containing aliphatic heterocycle" is one substituent or the same or different two or more substituents, which are selected from the group consisting of the following (vi) to (x):
(vi) a halogen atom, a hydroxyl group, a carboxyl group, a cyano group, an oxo group, a thioxo group, and an amidino group optionally substituted by one alkoxycarbonyl group or the same or different two alkoxycarbonyl groups;
(vii) a substituted or unsubstituted amino group, a substituted or unsubstituted carbamoyl group, and a substituted or unsubstituted sulfamoyl group;
(viii) an alkyl group, a haloalkyl group, an alkoxy group, a haloalkoxy group, an alkylcarbonyl group, an alkylcarbonyloxy group, an alkoxycarbonyl group, an alkylthio group and an alkylsulfonyl group
[these groups are optionally substituted by one or more substituents selected from a halogen atom, a hydroxyl group, a carboxyl group, a carbamoyl group optionally substituted by one alkyl group or the same or different two alkyl groups, an alkoxy group optionally substituted by alkoxy group(s) and/or a carbamoyl group(s), a haloalkoxy group, an alkylthio group, an alkoxycarbonyl group, an optionally substituted aryloxy group, an optionally substituted aromatic heterocyclyloxy group, an optionally substituted aryl group, an optionally substituted aromatic heterocyclic group and optionally substituted amino group. Examples of the substituent for the aryloxy group, aromatic heterocyclyloxy group, aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group. Examples of the substituent for the amino group include an optionally substituted alkyl group, an optionally substituted alkylcarbonyl group, an optionally substituted alkylsulfonyl group, and a carbamoyl group optionally substituted by one alkyl group or the same or different two alkyl groups. Examples of the substituent for the alkyl group of the alkyl group, alkylcarbonyl group, alkylsulfonyl group and carbamoyl group include a halogen atom, a hydroxyl group, a carboxyl group, an alkoxy group, a haloalkoxy group and a carbamoyl group];
(ix) a cycloalkyl group, a cycloalkenyl group, and a saturated or unsaturated aliphatic heterocyclic group
[these groups are optionally substituted by one or more substituents selected from a halogen atom, a hydroxyl group, a carboxyl group, an oxo group, a thioxo group, an amino group optionally substituted by one alkyl group or the same or different two alkyl groups, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];
(x) an aryl group, an aromatic heterocyclic group, an aryloxy group, an aromatic heterocyclyloxy group, an arylcarbonyl group, an aromatic heterocyclylcarbonyl group, an arylsulfonyl group and an aromatic heterocyclylsulfonyl group
[these groups are optionally substituted by one or more substituents selected from a halogen atom, a hydroxyl group, a carboxyl group, a cyano group, a substituted or unsubstituted amino group, a substituted or unsubstituted carbamoyl group, a substituted or unsubstituted sulfamoyl group, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group].

The substituent for the "phenyl group", "aryl group" and "aromatic heterocyclic group" is 1 to 5 substituents selected from the group consisting of the following (xi) to (xv):
(xi) a halogen atom, a hydroxyl group, a carboxyl group, a cyano group, a nitro group, a methylenedioxy group, an ethylenedioxy group and —$(CH_2)n$— (n is an integer of 3 to 5);
(xii) a substituted or unsubstituted amino group, a substituted or unsubstituted carbamoyl group, and a substituted or unsubstituted sulfamoyl group;

(xiii) an alkyl group, a haloalkyl group, an alkenyl group, an alkynyl group, an alkoxy group, a haloalkoxy group, an alkylcarbonyl group, an alkylcarbonyloxy group, an alkoxycarbonyl group, an alkylthio group and an alkylsulfonyl group
[these groups are optionally substituted by one or more substituents selected from a halogen atom, a hydroxyl group, a carboxyl group, an amino group optionally substituted by one alkyl group or the same or different two alkyl groups, an optionally substituted alkoxy group, a haloalkoxy group, an alkoxycarbonyl group, an optionally substituted aryl group and an optionally substituted aromatic heterocyclic group. Examples of the substituent for the alkoxy group, aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];

(xiv) a cycloalkyl group, a cycloalkenyl group, and a saturated or unsaturated aliphatic heterocyclic group
[these groups are optionally substituted by one or more substituents selected from a halogen atom, a hydroxyl group, a carboxyl group, an oxo group, a thioxo group, an amino group optionally substituted by one alkyl group or the same or different two alkyl groups, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];

(xv) an aryl group, an aromatic heterocyclic group, an aryloxy group, an aromatic heterocyclyloxy group, an arylcarbonyl group, an aromatic heterocyclylcarbonyl group, an arylsulfonyl group and an aromatic heterocyclylsulfonyl group
[these groups are optionally substituted by one or more substituents selected from a halogen atom, a hydroxyl group, a carboxyl group, a substituted or unsubstituted amino group, a substituted or unsubstituted carbamoyl group, a substituted or unsubstituted sulfamoyl group, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group].

The substituent for the "amino group", "carbamoyl group" and "sulfamoyl group" is one substituent or the same or different two substituents, which are selected from the group consisting of the following (xvi)-(xviii):

(xvi) an alkyl group, a haloalkyl group, an alkenyl group, an alkynyl group, an alkylcarbonyl group, an alkylsulfonyl group and an alkoxycarbonyl group
[these groups are optionally substituted by one or more substituents selected from a halogen atom, a hydroxyl group, a carboxyl group, an amino group optionally substituted by one alkyl group or the same or different two alkyl groups, a carbamoyl group, an alkoxy group, a haloalkoxy group, an alkoxycarbonyl group, a saturated or unsaturated aliphatic heterocyclic group, an optionally substituted aryl group and an optionally substituted aromatic heterocyclic group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];

(xvii) a cycloalkyl group, a cycloalkenyl group, and a saturated or unsaturated aliphatic heterocyclic group
[these groups are optionally substituted by one or more substituents selected from a halogen atom, a hydroxyl group, a carboxyl group, an oxo group, a thioxo group, an amino group optionally substituted by one alkyl group or the same or different two alkyl groups, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group];

(xviii) an aryl group, an aromatic heterocyclic group, an arylcarbonyl group, an aromatic heterocyclylcarbonyl group, an arylsulfonyl group and an aromatic heterocyclylsulfonyl group
[these groups are optionally substituted by one or more substituents selected from a halogen atom, a hydroxyl group, a carboxyl group, an amino group optionally substituted by one alkyl group or the same or different two alkyl groups, a carbamoyl group optionally substituted by one alkyl group or the same or different two alkyl groups, a sulfamoyl group optionally substituted by one alkyl group or the same or different two alkyl groups, an alkoxy group, a haloalkoxy group, an alkoxycarbonyl group, an optionally substituted alkyl group, an optionally substituted aryl group and an optionally substituted aromatic heterocyclic group. Examples of the substituent for the alkyl group include a halogen atom, a hydroxyl group, a carboxyl group, an alkoxy group and a haloalkoxy group. Examples of the substituent for the aryl group and aromatic heterocyclic group include a halogen atom, a hydroxyl group, a carboxyl group, an alkyl group, a haloalkyl group, an alkoxy group, a haloalkoxy group, an alkoxycarbonyl group, a nitro group, a cyano group and a carbamoyl group].

In addition, the two substituents for the "amino group", "carbamoyl group" or "sulfamoyl group" are optionally bonded to form, together with the adjacent nitrogen atom, a 5- to 10-membered nitrogen-containing aliphatic heterocycle. Examples of the nitrogen-containing aliphatic heterocycle include pyrrolidine ring, piperidine ring, an azepane ring, an azocane ring, a piperazine ring, a morpholine ring, a thiomorpholine ring and a tetrahydroisoquinoline ring. In addition, the nitrogen-containing aliphatic heterocycle is optionally substituted by one or more substituents selected from halogen, a hydroxyl group, a carboxyl group, an optionally substituted alkyl group, a haloalkyl group, an alkoxy group and a haloalkoxy group. Examples of the substituent for the alkyl group include a halogen atom, a hydroxyl group, a carboxyl group, an alkoxy group, a haloalkoxy group and a carbamoyl group.

In the compound of the present invention represented by the formula (1), each of the groups is preferably as follows.

$R^1$ is a hydrogen atom, a halogen atom, an alkyl group having 1 to 6 carbon atoms, a haloalkyl group having 1 to 6 carbon atoms, an alkoxy group having 1 to 6 carbon atoms or a haloalkoxy group having 1 to 6 carbon atoms, preferably a hydrogen atom, a halogen atom, an alkyl group having 1 to 6 carbon atoms or a haloalkyl group having 1 to 6 carbon atoms, more preferably a hydrogen atom, a halogen atom or an alkyl group having 1 to 6 carbon atoms, more preferably a hydrogen atom or a halogen atom, particularly preferably a hydrogen atom. $R^1$ can be present on the benzene ring or pyridine ring at any substitutable position.

Specific examples of $R^1$ include a hydrogen atom, a fluorine atom, a chlorine atom, a methyl group, an ethyl group, a propyl group, a trifluoromethyl group and the like. Among them, a hydrogen atom, a fluorine atom and a chlorine atom are preferable, and a hydrogen atom is more preferable.

L is a single bond, —O— or —CH$_2$O—, preferably, a single bond or —O—, more preferably —O—. L can be present on the benzene ring or pyridine ring at any substitutable position. When L is —CH$_2$O—, the oxygen atom of —CH$_2$O— is bonded to the benzene ring or pyridine ring, and the methylene chain is bonded to $R^2$.

$R^2$ is a substituted or unsubstituted 6- to 10-membered aryl group, or a substituted or unsubstituted 5- to 10-membered aromatic heterocyclic group, preferably a substituted or unsubstituted 6- to 10-membered aryl group, more preferably a substituted or unsubstituted phenyl group.

Preferable examples of the substituent of the aryl group or aromatic heterocyclic group for $R^2$ include a halogen atom, a substituted or unsubstituted alkyl group (preferably an unsubstituted alkyl group having 1 to 6 carbon atoms), a haloalkyl group (preferably a haloalkyl group having 1 to 6 carbon atoms), an alkoxy group (preferably an alkoxy group having 1 to 6 carbon atoms), a haloalkoxy group (preferably a haloalkoxy group having 1 to 6 carbon atoms), a cyano group and the like, specifically, a fluorine atom, a chlorine atom, a methyl group, an ethyl group, an isopropyl group, a tert-butyl group, a trifluoromethyl group, a trifluoromethoxy group, a methoxy group, an ethoxy group, a cyano group and the like. Among them, a fluorine atom, a methyl group and a trifluoromethoxy group are preferable.

Specific examples of the substituted or unsubstituted aryl group for $R^2$ include a phenyl group and a phenyl group substituted by preferable substituent(s) for the aforementioned aryl group, and the like.

Specific examples of the aromatic heterocyclic group for $R^2$ include a pyridyl group, a furyl group, a thienyl group, a pyrimidinyl group, a pyrazinyl group and the like. Among them, a pyridyl group and a furyl group are preferable.

$R^3$ is a substituted or unsubstituted alkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, or a substituted or unsubstituted 5- to 10-membered unsaturated aliphatic heterocyclic group, preferably a substituted or unsubstituted alkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, more preferably a substituted or unsubstituted alkyl group having 1 to 6 carbon atoms, a substituted or unsubstituted 3- to 8-membered cycloalkyl group, or a substituted or unsubstituted 4- to 8-membered saturated aliphatic heterocyclic group, still more preferably a substituted or unsubstituted alkyl group having 1 to 6 carbon atoms, or a substituted or unsubstituted 3- to 8-membered cycloalkyl group.

Preferable examples of the substituent for the alkyl group for $R^3$ include a hydroxyl group, an alkoxy group (preferably an alkoxy group having 1 to 6 carbon atoms), a 4- to 8-membered saturated aliphatic heterocyclic group and the like, specifically, a hydroxyl group, a methoxy group, an ethoxy group, an isopropoxy group, a tetrahydrofuryl group, a tetrahydropyranyl group and the like.

Preferable examples of the substituent for the saturated aliphatic heterocyclic group for $R^3$ include an alkylcarbonyl group, an alkoxycarbonyl group, an alkylsulfonyl group, a mono-alkylcarbamoyl group (the alkyl moiety has preferably 1 to 6 carbon atoms) and the like, specifically, an acetyl group, a tert-butoxycarbonyl group, a methylsulfonyl group, an isopropylcarbamoyl group and the like.

Specific examples of $R^3$ include an ethyl group, an isopropyl group, a cyclopropyl group, a cyclobutyl group, a cyclopentyl group, a methoxyethyl group, an ethoxyethyl group, an isopropoxyethyl group, a hydroxyethyl group, a methoxypropyl group, an ethoxypropyl group, a hydroxypropyl group, a tetrahydropyranyl group, a tetrahydrofuryl group, a 2,2-dimethyl-2-hydroxyethyl group, a tetrahydropyranylmethyl group, a tetrahydrofurylmethyl group, a 4-piperidyl group, a 1-(tert-butoxycarbonyl)piperidin-4-yl group, a 1-isopropylcarbamoylpiperidin-4-yl group, a 1-acetylpiperidin-4-yl group, a 1-methylsulfonylpiperidin-4-yl group and the like. $R^3$ is more preferable a cyclobutyl group, a 2-ethoxyethyl group or an ethyl group.

$R^4$ is a hydrogen atom, a substituted or unsubstituted alkyl group having 1 to 6 carbon atoms, or a substituted or unsubstituted 3- to 8-membered cycloalkyl group, preferably a hydrogen atom, or a substituted or unsubstituted alkyl group having 1 to 6 carbon atoms, more preferably a hydrogen atom.

Preferable examples of the substituent for the alkyl group and cycloalkyl group for $R^4$ include a halogen atom, a hydroxyl group, an alkoxy group (preferably an alkoxy group having 1 to 6 carbon atoms), a 4- to 8-membered saturated aliphatic heterocyclic group and the like, specifically, a fluorine atom, a chlorine atom, a hydroxyl group, a methoxy group, an ethoxy group, a tetrahydrofuryl group, a tetrahydropyranyl group and the like.

Specific examples of $R^4$ include a hydrogen atom, a methyl group, cyclopropyl group and the like. Among them, a hydrogen atom and a methyl group are preferable, and a hydrogen atom is more preferable.

$R^{5a}$ and $R^{5b}$ are each independently a hydrogen atom, or a substituted or unsubstituted alkyl group having 1 to 6 carbon atoms, or $R^4$ and $R^{5a}$ are optionally bonded to form, together with the nitrogen atom that $R^4$ is bonded to, a 4- to 8-membered saturated nitrogen-containing aliphatic heterocycle (in this case, $R^{5b}$ is a hydrogen atom), preferably independently each a hydrogen atom, or a substituted or unsubstituted alkyl group having 1 to 6 carbon atoms. Preferable examples of the substituent for the alkyl group for $R^{5a}$ or $R^{5b}$ include a halogen atom, a hydroxyl group, an alkoxy group (preferably an alkoxy group having 1 to 6 carbon atoms), a 4- to 8-membered saturated aliphatic heterocyclic group and the like, specifically, a fluorine atom, a chlorine atom, a hydroxyl group, a methoxy group, an ethoxy group, tetrahydrofuryl group, tetrahydropyranyl group and the like.

Specific examples of $R^{5a}$ and $R^{5b}$ include independently each a hydrogen atom, a methyl group, an ethyl group and an isopropyl group (preferably $R^{5a}$ is a hydrogen atom, a methyl group, an ethyl group or an isopropyl group, and $R^{5b}$ is a methyl group, an ethyl group or an isopropyl group). Among them, a hydrogen atom and a methyl group are preferable (preferably $R^{5a}$ is a hydrogen atom, and $R^{5b}$ is a methyl group).

When $R^{5a}$ and $R^{5b}$ are different from each other, the carbon atom that they are bonded to is an asymmetric carbon atom, and the steric configuration is preferably S-configuration from the aspects of easy availability of the starting materials.

Specific examples of the 4- to 8-membered saturated nitrogen-containing aliphatic heterocycle formed by $R^4$ and $R^{5a}$ which are bonded to each other, together with the nitrogen atom that $R^4$ is bonded to, include an azetidine ring, a pyrrolidine ring, a piperidine ring and the like. Among them, pyrrolidine ring is preferable.

$R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, a substituted or unsubstituted 5- to 10-membered unsaturated aliphatic heterocyclic group, a substituted or unsubstituted 6- to 10-membered aryl group, or a substituted or unsubstituted 5- to 10-membered aromatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms), preferably independently each a hydrogen atom, a substituted or unsubstituted alkyl group having 1 to 6 carbon atoms, a haloalkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, more preferably independently each a hydrogen atom, or a substituted or unsubstituted alkyl group having 1 to 6 carbon atoms, more preferably a hydrogen atom.

Preferable examples of the substituent for the alkyl group for $R^6$ or $R^7$ include a hydroxyl group, an alkoxy group (preferably an alkoxy group having 1 to 6 carbon atoms), a 4- to 8-membered saturated aliphatic heterocyclic group and the like, specifically, a hydroxyl group, a methoxy group, an ethoxy group, a tetrahydrofuryl group, a tetrahydropyranyl group, a pyrrolidinyl group, a piperidyl group, a piperidino group, a piperazinyl group, a morpholino group and the like. Specific examples of the substituted alkyl group for $R^6$ or $R^7$ include a methoxyethyl group, a 2,2-dimethyl-2-hydroxyethyl group, a morpholinoethyl group and the like.

Preferable specific examples of $R^6$ or $R^7$ include a hydrogen atom, a methyl group, an ethyl group, an isopropyl group and the like. Among them, a hydrogen atom and a methyl group are preferable, and a hydrogen atom is more preferable.

Specific examples of the substituted or unsubstituted 4- to 8-membered saturated nitrogen-containing aliphatic heterocycle and substituted or unsubstituted 5- to 10-membered unsaturated nitrogen-containing aliphatic heterocycle, which are formed by $R^6$ and $R^7$ which are bonded to each other, together with the nitrogen atom that they are bond to, include a morpholine ring, a pyrrolidine ring, a piperidine ring, a piperazine ring and the like. Among them, a morpholine ring and a piperazine ring are preferable.

Preferable examples of the substituent for the above-mentioned saturated nitrogen-containing aliphatic heterocycle and unsaturated nitrogen-containing aliphatic heterocycle include an oxo group, a cyano group, a haloalkyl group (preferably a haloalkyl group having 1 to 6 carbon atoms) and the like. Among them, an oxo group, a cyano group and a trifluoromethyl group are preferable.

Preferable examples of compound (1) include the following compounds and a pharmaceutically acceptable salt thereof.

Preferable embodiments thereof include a compound wherein $R^1$ is a hydrogen atom or a halogen atom,
L is a single bond or —O—,
$R^2$ is a substituted or unsubstituted phenyl group,
X is a carbon atom,
$R^3$ is a substituted or unsubstituted alkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group,
$R^4$ is a hydrogen atom, or a substituted or unsubstituted alkyl group having 1 to 6 carbon atoms,
$R^{5a}$ and $R^{5b}$ are each independently a hydrogen atom, or a substituted or unsubstituted alkyl group having 1 to 6 carbon atoms, and
$R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms).

Other preferable embodiments thereof include a compound wherein $R^1$ is a hydrogen atom, a halogen atom or an alkyl group having 1 to 6 carbon atoms,
L is a single bond or —O—,
$R^2$ is a substituted or unsubstituted 6- to 10-membered aryl group (the substituent is preferably a halogen atom, an alkyl group having 1 to 6 carbon atoms or a haloalkoxy group having 1 to 6 carbon atoms, more preferably a fluorine atom, a methyl group or a trifluoromethoxy group),
X is a carbon atom,
$R^3$ is a substituted or unsubstituted alkyl group having 1 to 6 carbon atoms (the substituent is preferably a hydroxyl group, an alkoxy group having 1 to 6 carbon atoms or a 4- to 8-membered saturated aliphatic heterocyclic group, more preferably a hydroxyl group, a methoxy group, an ethoxy group, an isopropoxy group, a tetrahydrofuryl group or a tetrahydropyranyl group), a substituted or unsubstituted 3- to 8-membered cycloalkyl group (preferably an unsubstituted 3- to 8-membered cycloalkyl group), a substituted or unsubstituted 4- to 8-membered saturated aliphatic heterocyclic group (preferably an unsubstituted 4- to 8-membered saturated aliphatic heterocyclic group), or a substituted or unsubstituted 5- to 10-membered unsaturated aliphatic heterocyclic group (preferably an unsubstituted 5- to 10-membered unsaturated aliphatic heterocyclic group), $R^4$ is a hydrogen atom, or a substituted or unsubstituted alkyl group having 1 to 6 carbon atoms (preferably an unsubstituted alkyl group having 1 to 6 carbon atoms), $R^{5a}$ and $R^{5b}$ are each independently a hydrogen atom, or a substituted or unsubstituted alkyl group having 1 to 6 carbon atoms (preferably an unsubstituted alkyl group having 1 to 6 carbon atoms), and $R^6$ and $R^7$ are each independently a hydrogen atom, or a substituted or unsubstituted alkyl group having 1 to 6 carbon atoms (preferably an unsubstituted alkyl group having 1 to 6 carbon atoms).

Among them, a compound wherein
$R^1$ is a hydrogen atom or a halogen atom,
L is a single bond or —O—,
$R^2$ is a substituted or unsubstituted phenyl group (the substituent is preferably a halogen atom, an alkyl group having 1 to 6 carbon atoms or a haloalkoxy group having 1 to 6 carbon atoms, more preferably a fluorine atom, a methyl group or a trifluoromethoxy group),
X is a carbon atom,
$R^3$ is a substituted or unsubstituted alkyl group having 1 to 6 carbon atoms (the substituent is preferably a hydroxyl group, an alkoxy group having 1 to 6 carbon atoms or a 4- to 8-membered saturated aliphatic heterocyclic group, more preferably a hydroxyl group, a methoxy group, an ethoxy group, an isopropoxy group, a tetrahydrofuryl group or a tetrahydropyranyl group), or a substituted or unsubstituted 3- to 8-membered cycloalkyl group (preferably an unsubstituted 3- to 8-membered cycloalkyl group),
$R^4$ is a hydrogen atom or a methyl group,
$R^{5a}$ and $R^{5b}$ are each independently a hydrogen atom, a methyl group, an ethyl group or an isopropyl group (preferably $R^{5a}$ is a hydrogen atom, a methyl group, an ethyl group or an isopropyl group, and $R^{5b}$ is a methyl group, an ethyl group or an isopropyl group), and
$R^6$ and $R^7$ is a hydrogen atom,
is preferable, and
a compound wherein
$R^1$ is a hydrogen atom,
L is —O—,
$R^2$ is a substituted or unsubstituted phenyl group (the substituent is preferably a halogen atom, an alkyl group having 1 to 6 carbon atoms or a haloalkoxy group having 1 to 6 carbon atoms, more preferably a fluorine atom, a methyl group or a trifluoromethoxy group),
X is a carbon atom,
$R^3$ is a substituted or unsubstituted alkyl group having 1 to 6 carbon atoms (the substituent is preferably a hydroxyl group, an alkoxy group having 1 to 6 carbon atoms or a 4- to 8-membered saturated aliphatic heterocyclic group, more preferably a hydroxyl group, a methoxy group, an ethoxy group, an isopropoxy group, a tetrahydrofuryl group or a tetrahydropyranyl group), or a substituted or unsubstituted 3- to 8-membered cycloalkyl group (preferably an unsubstituted 3- to 8-membered cycloalkyl group),
$R^4$ is a hydrogen atom or a methyl group,
$R^{5a}$ and $R^{5b}$ are each independently a hydrogen atom or a methyl group (preferably $R^{5a}$ is a hydrogen atom, and $R^{5b}$ is a methyl group), and
$R^6$ and $R^7$ is a hydrogen atom,
is more preferable.

The compound of the present invention is preferably compound (2) or compound (3) or a pharmaceutically acceptable salt thereof, more preferably compound (2) or a pharmaceutically acceptable salt thereof.

Preferable specific examples thereof include the following compounds and a pharmaceutically acceptable salt thereof.

Specific examples thereof include a compound wherein
$R^1$ is
(1) a hydrogen atom,
(2) a halogen atom (preferably a fluorine atom, a chlorine atom),
(3) a $C_{1-6}$ alkyl group (preferably methyl) or
(4) a $C_{1-6}$ haloalkyl group (preferably trifluoromethyl),
L is
(1) a single bond,
(2) —O— or
(3) —CH$_2$O—,
$R^2$ is
(1) a $C_{6-10}$ aryl group (the $C_{6-10}$ aryl group is optionally condensed with a $C_{3-6}$ cycloalkane) (preferably phenyl, indanyl, more preferably phenyl) optionally substituted by 1 to 3 substituents selected from
  (a) a halogen atom (preferably a fluorine atom, a chlorine atom),
  (b) a $C_{1-6}$ alkyl group (preferably methyl, ethyl, isopropyl, tert-butyl),
  (c) a $C_{1-6}$ haloalkyl group (preferably trifluoromethyl),
  (d) a $C_{1-6}$ alkoxy group (preferably methoxy, ethoxy),
  (e) a $C_{1-6}$ haloalkoxy group (preferably trifluoromethoxy) and
  (f) a cyano group, or
(2) a 5- to 10-membered aromatic heterocyclic group (preferably a 5- or 6-membered aromatic heterocyclic group, more preferably pyridyl, furyl),
X is a carbon atom or a nitrogen atom,
$R^3$ is
(1) a $C_{1-6}$ alkyl group (preferably methyl, ethyl, propyl, isopropyl, isobutyl) optionally substituted by 1 to 3 substituents selected from
  (a) a $C_{1-6}$ alkoxy group (preferably methoxy, ethoxy, isopropoxy),
  (b) a 4- to 8-membered saturated aliphatic heterocyclic group (preferably a 5- or 6-membered saturated aliphatic heterocyclic group, more preferably tetrahydropyranyl, tetrahydrofuryl), and
  (c) a hydroxyl group,
(2) a $C_{3-8}$ cycloalkyl group (preferably cyclopropyl, cyclobutyl, cyclopentyl), or
(3) a 4- to 8-membered saturated aliphatic heterocyclic group (preferably a 5- or 6-membered saturated aliphatic heterocyclic group, more preferably tetrahydropyranyl, piperidyl) optionally substituted by 1 to 3 substituents selected from
  (a) a $C_{1-6}$ alkyl-carbonyl group (preferably acetyl),
  (b) a $C_{1-6}$ alkoxy-carbonyl group (preferably tert-butoxycarbonyl),
  (c) a $C_{1-6}$ alkylsulfonyl group (preferably methylsulfonyl), and
  (d) a carbamoyl group optionally mono- or di-substituted by $C_{1-6}$ alkyl group(s) (preferably isopropyl),
$R^4$ is
(1) a hydrogen atom, or
(2) a $C_{1-6}$ alkyl group (preferably methyl),
$R^{5a}$ and $R^{5b}$ are each independently
(1) a hydrogen atom, or
(2) a $C_{1-6}$ alkyl group (preferably methyl, ethyl, isopropyl), or
$R^4$ and $R^{5a}$ are optionally bonded to form, together with the nitrogen atom that $R^4$ is bonded to, a 4- to 8-membered saturated nitrogen-containing aliphatic heterocycle (preferably a 5- or 6-membered saturated nitrogen-containing aliphatic heterocycle, more preferably pyrrolidine) (in this case, $R^{5b}$ is a hydrogen atom), and
$R^6$ and $R^7$ are each independently
(1) a hydrogen atom, or
(2) a $C_{1-6}$ alkyl group (preferably ethyl, isobutyl) optionally substituted by 1 to 3 substituents selected from
    (a) a hydroxyl group,
    (b) a $C_{1-6}$ alkoxy group (preferably methoxy), and
    (c) a 4- to 8-membered saturated aliphatic heterocyclic group (preferably a 5- or 6-membered saturated aliphatic heterocyclic group, more preferably morpholinyl), or
$R^6$ and $R^7$ are optionally bonded to form, together with the nitrogen atom that they are bond to, a 4- to 8-membered saturated nitrogen-containing aliphatic heterocycle (preferably a 5- or 6-membered saturated nitrogen-containing aliphatic heterocycle, more preferably morpholine, piperazine) optionally substituted by 1 to 3 substituents selected from
    (a) an oxo group,
    (b) a cyano group, and
    (c) a $C_{1-6}$ haloalkyl group (preferably trifluoromethyl).

Preferable specific examples thereof include a compound wherein
$R^1$ is
(1) a hydrogen atom, or
(2) a halogen atom (preferably a fluorine atom, a chlorine atom),
L is
(1) a single bond, or
(2) —O—,
$R^2$ is a phenyl group optionally substituted by 1 to 3 substituents selected from
    (a) a halogen atom (preferably a fluorine atom, a chlorine atom),
    (b) a $C_{1-6}$ alkyl group (preferably methyl, ethyl, isopropyl, tert-butyl),
    (c) a $C_{1-6}$ haloalkyl group (preferably trifluoromethyl),
    (d) a $C_{1-6}$ alkoxy group (preferably methoxy, ethoxy),
    (e) a $C_{1-6}$ haloalkoxy group (preferably trifluoromethoxy), and
    (f) a cyano group,
X is a carbon atom,
$R^3$ is
(1) a $C_{1-6}$ alkyl group (preferably methyl, ethyl, propyl, isopropyl, isobutyl) optionally substituted by 1 to 3 substituents selected from
    (a) a $C_{1-6}$ alkoxy group (preferably methoxy, ethoxy, isopropoxy),
    (b) a 4- to 8-membered saturated aliphatic heterocyclic group (preferably a 5- or 6-membered saturated aliphatic heterocyclic group, more preferably tetrahydropyranyl, tetrahydrofuryl), and
    (c) a hydroxyl group,
(2) a $C_{3-8}$ cycloalkyl group (preferably cyclopropyl, cyclobutyl, cyclopentyl), or
(3) a 4- to 8-membered saturated aliphatic heterocyclic group (preferably a 5- or 6-membered saturated aliphatic heterocyclic group, more preferably tetrahydropyranyl, piperidyl) optionally substituted by 1 to 3 substituents selected from
    (a) a $C_{1-6}$ alkyl-carbonyl group (preferably acetyl),
    (b) a $C_{1-6}$ alkoxy-carbonyl group (preferably tert-butoxycarbonyl),
    (c) a $C_{1-6}$ alkylsulfonyl group (preferably methylsulfonyl), and
    (d) a carbamoyl group optionally mono- or di-substituted by $C_{1-6}$ alkyl group(s) (preferably isopropyl),
$R^4$ is
(1) a hydrogen atom, or
(2) a $C_{1-6}$ alkyl group (preferably methyl),
$R^{5a}$ and $R^{5b}$ are each independently
(1) a hydrogen atom, or
(2) a $C_{1-6}$ alkyl group (preferably methyl, ethyl, isopropyl), and
$R^6$ and $R^7$ are each independently
(1) a hydrogen atom, or
(2) a $C_{1-6}$ alkyl group (preferably ethyl, isobutyl) optionally substituted by 1 to 3 substituents selected from
    (a) a hydroxyl group,
    (b) a $C_{1-6}$ alkoxy group (preferably methoxy), and
    (c) a 4- to 8-membered saturated aliphatic heterocyclic group (preferably a 5- or 6-membered saturated aliphatic heterocyclic group, more preferably morpholinyl), or
$R^6$ and $R^7$ are optionally bonded to form, together with the nitrogen atom that they are bond to, a 4- to 8-membered saturated nitrogen-containing aliphatic heterocycle (preferably a 5- or 6-membered saturated nitrogen-containing aliphatic heterocycle, more preferably morpholine, piperazine) optionally substituted by 1 to 3 substituents selected from
    (a) an oxo group,
    (b) a cyano group, and
    (c) a $C_{1-6}$ haloalkyl group (preferably trifluoromethyl).

Other preferable specific examples thereof include a compound wherein
$R^1$ is
(1) a hydrogen atom,
(2) a halogen atom (preferably a fluorine atom, a chlorine atom), or
(3) a $C_{1-6}$ alkyl group (preferably methyl),
L is
(1) a single bond, or
(2) —O—,
$R^2$ is a $C_{6-10}$ aryl group (the $C_{6-10}$ aryl group is optionally condensed with a $C_{3-6}$ cycloalkane) (preferably phenyl, indanyl, more preferably phenyl) optionally substituted by 1 to 3 substituents selected from
    (a) a halogen atom (preferably a fluorine atom, a chlorine atom),
    (b) a $C_{1-6}$ alkyl group (preferably methyl, ethyl, isopropyl, tert-butyl),
    (c) a $C_{1-6}$ haloalkyl group (preferably trifluoromethyl),
    (d) a $C_{1-6}$ alkoxy group (preferably methoxy, ethoxy),
    (e) a $C_{1-6}$ haloalkoxy group (preferably trifluoromethoxy), and
    (f) a cyano group,
X is a carbon atom,
$R^3$ is
(1) a $C_{1-6}$ alkyl group (preferably methyl, ethyl, propyl, isopropyl, isobutyl) optionally substituted by 1 to 3 substituents selected from
    (a) a $C_{1-6}$ alkoxy group (preferably methoxy, ethoxy, isopropoxy),
    (b) a 4- to 8-membered saturated aliphatic heterocyclic group (preferably a 5- or 6-membered saturated aliphatic heterocyclic group, more preferably tetrahydropyranyl, tetrahydrofuryl), and
    (c) a hydroxyl group,
(2) a $C_{3-8}$ cycloalkyl group (preferably cyclopropyl, cyclobutyl, cyclopentyl), or
(3) a 4- to 8-membered saturated aliphatic heterocyclic group (preferably a 5- or 6-membered saturated aliphatic heterocyclic group, more preferably tetrahydropyranyl, piperidyl) optionally substituted by 1 to 3 substituents selected from
  (a) a $C_{1-6}$ alkyl-carbonyl group (preferably acetyl),
  (b) a $C_{1-6}$ alkoxy-carbonyl group (preferably tert-butoxycarbonyl),
  (c) a $C_{1-6}$ alkylsulfonyl group (preferably methylsulfonyl), and
  (d) a carbamoyl group optionally mono- or di-substituted by $C_{1-6}$ alkyl group(s) (preferably isopropyl),
$R^4$ is
(1) a hydrogen atom, or
(2) a $C_{1-6}$ alkyl group (preferably methyl),
$R^{5a}$ and $R^{5b}$ are each independently
(1) a hydrogen atom, or
(2) a $C_{1-6}$ alkyl group (preferably methyl, ethyl, isopropyl), and
$R^6$ and $R^7$ are each independently
(1) a hydrogen atom, or
(2) a $C_{1-6}$ alkyl group (preferably ethyl, isobutyl) optionally substituted by 1 to 3 substituents selected from
  (a) a hydroxyl group,
  (b) a $C_{1-6}$ alkoxy group (preferably methoxy), and
  (c) a 4- to 8-membered saturated aliphatic heterocyclic group (preferably a 5- or 6-membered saturated aliphatic heterocyclic group, more preferably morpholinyl).

Among them, a compound wherein
$R^1$ is
(1) a hydrogen atom, or
(2) a halogen atom (preferably a fluorine atom, a chlorine atom),
L is
(1) a single bond, or
(2) —O—,
$R^2$ is a phenyl group optionally substituted by 1 to 3 substituents selected from
  (a) a halogen atom (preferably a fluorine atom, a chlorine atom),
  (b) a $C_{1-6}$ alkyl group (preferably methyl, ethyl, isopropyl, tert-butyl),
  (c) a $C_{1-6}$ haloalkyl group (preferably trifluoromethyl),
  (d) a $C_{1-6}$ alkoxy group (preferably methoxy, ethoxy),
  (e) a $C_{1-6}$ haloalkoxy group (preferably trifluoromethoxy), and
  (f) a cyano group,
X is a carbon atom,
$R^3$ is
(1) a $C_{1-6}$ alkyl group (preferably methyl, ethyl, propyl, isopropyl, isobutyl) optionally substituted by 1 to 3 substituents selected from
  (a) a $C_{1-6}$ alkoxy group (preferably methoxy, ethoxy, isopropoxy),
  (b) a 4- to 8-membered saturated aliphatic heterocyclic group (preferably a 5- or 6-membered saturated aliphatic heterocyclic group, more preferably tetrahydropyranyl, tetrahydrofuryl), and
  (c) a hydroxyl group, or
(2) a $C_{3-8}$ cycloalkyl group (preferably cyclopropyl, cyclobutyl, cyclopentyl),
$R^4$ is a hydrogen atom or a methyl group,
$R^{5a}$ and $R^{5b}$ are each independently a hydrogen atom, a methyl group, an ethyl group or an isopropyl group (preferably $R^{5a}$ is a hydrogen atom, a methyl group, an ethyl group or an isopropyl group, and $R^{5b}$ is a methyl group, an ethyl group or an isopropyl group), and $R^6$ and $R^7$ is a hydrogen atom,
is preferable, and
a compound wherein
$R^1$ is a hydrogen atom,
L is —O—,
$R^2$ is a phenyl group optionally substituted by 1 to 3 substituents selected from
  (a) a halogen atom (preferably a fluorine atom, a chlorine atom),
  (b) a $C_{1-6}$ alkyl group (preferably methyl, ethyl, isopropyl, tert-butyl),
  (c) a $C_{1-6}$ haloalkyl group (preferably trifluoromethyl),
  (d) a $C_{1-6}$ alkoxy group (preferably methoxy, ethoxy),
  (e) a $C_{1-6}$ haloalkoxy group (preferably trifluoromethoxy), and
  (f) a cyano group,
X is a carbon atom,
$R^3$ is
(1) a $C_{1-6}$ alkyl group (preferably methyl, ethyl, propyl, isopropyl, isobutyl) optionally substituted by 1 to 3 substituents selected from
  (a) a $C_{1-6}$ alkoxy group (preferably methoxy, ethoxy, isopropoxy),
  (b) a 4- to 8-membered saturated aliphatic heterocyclic group (preferably a 5- or 6-membered saturated aliphatic heterocyclic group, more preferably tetrahydropyranyl, tetrahydrofuryl), and
  (c) a hydroxyl group, or
(2) a $C_{3-8}$ cycloalkyl group (preferably cyclopropyl, cyclobutyl, cyclopentyl),
$R^4$ is a hydrogen atom or a methyl group, and
$R^{5a}$ and $R^{5b}$ are each independently a hydrogen atom or a methyl group (preferably $R^{5a}$ is a hydrogen atom, and $R^{5b}$ is a methyl group), and
$R^6$ and $R^7$ is a hydrogen atom,
is more preferable.

Other preferable specific examples thereof include
$N^2$-{[1-(2-ethoxyethyl)-6-(4-fluorophenoxy)-1H-benzimidazol-2-yl]methyl}glycinamide,
$N^2$-{[1-(2-ethoxyethyl)-6-(4-fluorophenoxy)-1H-benzimidazol-2-yl]methyl}-2-methylalaninamide,
$N^2$-{[1-cyclopropyl-6-(4-fluorophenoxy)-1H-benzimidazol-2-yl]methyl}-L-alaninamide,
$N^2$-{[1-cyclobutyl-6-(4-fluorophenoxy)-1H-benzimidazol-2-yl]methyl}-L-alaninamide,
$N^2$-{[6-(4-chlorophenoxy)-1-(2-ethoxyethyl)-1H-benzimidazol-2-yl]methyl}-L-alaninamide,
$N^2$-{[6-(4-fluorophenoxy)-1-(2-hydroxy-2-methylpropyl)-1H-benzimidazol-2-yl]methyl}-L-alaninamide,
$N^2$-{[1-(2-ethoxyethyl)-6-(4-fluorophenoxy)-1H-benzimidazol-2-yl]methyl}-L-alaninamide,
$N^2$-{[6-(4-fluorophenoxy)-1-(3-methoxypropyl)-1H-benzimidazol-2-yl]methyl}-L-alaninamide,
$N^2$-{[6-(2-chloro-4-fluorophenoxy)-1-(2-ethoxyethyl)-1H-benzimidazol-2-yl]methyl}-L-alaninamide,
$N^2$-{[1-ethyl-6-(4-methylphenoxy)-1H-benzimidazol-2-yl]methyl}-L-alaninamide,
$N^2$-{[6-(2,4-difluorophenoxy)-1-(2-hydroxy-2-methylpropyl)-1H-benzimidazol-2-yl]methyl}-L-alaninamide,
$N^2$-{[1-(2-ethoxyethyl)-5-fluoro-6-(4-fluorophenyl)-1H-benzimidazol-2-yl]methyl}-L-alaninamide,
$N^2$-{[1-ethyl-5-fluoro-6-(4-fluorophenyl)-1H-benzimidazol-2-yl]methyl}-L-alaninamide,
$N^2$-{[1-(3-methoxypropyl)-6-(4-methylphenoxy)-1H-benzimidazol-2-yl]methyl}-L-alaninamide,
$N^2$-{[6-(4-methylphenoxy)-1-(tetrahydro-2H-pyran-4-yl)-1H-benzimidazol-2-yl]methyl}-L-alaninamide, N²-{[5-chloro-1-(2-ethoxyethyl)-6-(4-fluorophenyl)-1H-benzimidazol-2-yl]methyl}-L-alaninamide, and N²-{[5-chloro-6-(3,4-difluorophenyl)-1-(2-ethoxyethyl)-1H-benzimidazol-2-yl]methyl}-L-alaninamide, and pharmaceutically acceptable salts thereof.

Compound (1) can be prepared, for example, according to the method shown below.

Reaction Scheme-1

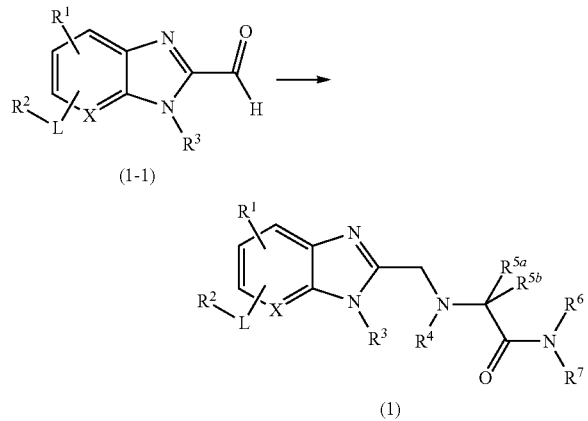

wherein $R^1$, $R^2$, $R^3$, $R^4$, $R^{5a}$, $R^{5b}$, $R^6$, $R^7$, L and X are as defined above.

Compound (1) can be prepared by subjecting compound (1-1) to a reductive amination with the corresponding amine compound. As the solvent, ether solvents such as tetrahydrofuran, 1,4-dioxane and the like, halogenated solvents such as dichloromethane, chloroform, 1,2-dichloroethane and the like, alcohol solvents such as methanol, ethanol and the like, ethyl acetate, N,N-dimethylformamide, acetonitrile and the like can be used. Among them, tetrahydrofuran, dichloromethane and methanol are preferable. As the reducing agent, sodium borohydride, sodium triacetoxyborohydride, sodium cyanoborohydride and the like can be used. The reaction temperature is −20° C.—the refluxing temperature of the reaction solvent, and particularly preferably 0° C.—near room temperature. Molecular sieves or sodium sulfate may be added as a dehydrating agent. Acetic acid or hydrochloric acid may be added as an additive.

Compound (1A), which is compound (1) wherein $R^4$ and $R^{5a}$ are not bonded, can also be prepared from compound (1-1) according to the method shown in Reaction Scheme-2 below.

Reaction Scheme-2

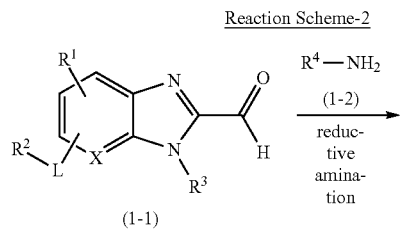

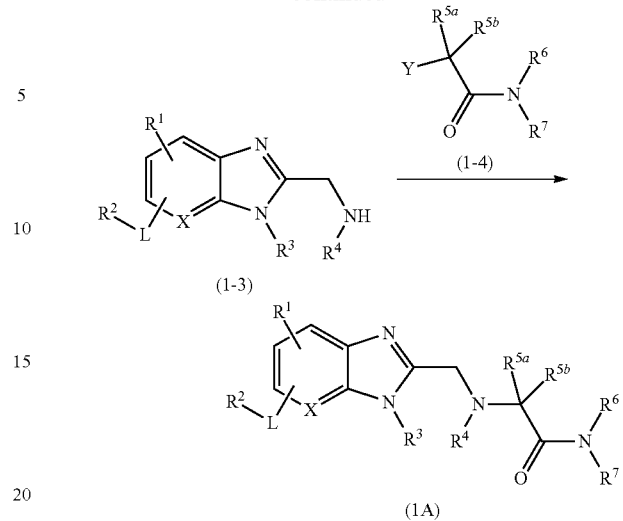

wherein $R^1$, $R^2$, $R^3$, $R^4$, $R^{5a}$, $R^{5b}$, $R^6$, $R^7$, L and X are as defined above except that $R^4$ and $R^{5a}$ are not bonded, and Y is a leaving group such as a halogen atom, a mesyloxy group, a tosyloxy group and the like.

Compound (1-1) is subjected to a reductive amination with compound (1-2) to give compound (1-3), and compound (1-3) is reacted with compound (1-4) in the presence of a base, in a solvent such as ether solvent (e.g., tetrahydrofuran, 1,4-dioxane and the like), halogenated solvent (e.g., dichloromethane, chloroform, 1,2-dichloroethane and the like), ethyl acetate, N,N-dimethylformamide, acetonitrile and the like, at 0° C.—the refluxing temperature of the reaction solvent to give compound (1A). While the base is not particularly limited, inorganic bases such as potassium carbonate, cesium carbonate, sodium hydroxide, sodium hydride, potassium hydride, potassium tert-butoxide and the like, and organic bases such as triethylamine, diisopropylethylamine and the like can be used.

In addition, compound (1) can also be prepared according to the method shown in Reaction Scheme-3 below.

Reaction Scheme-3

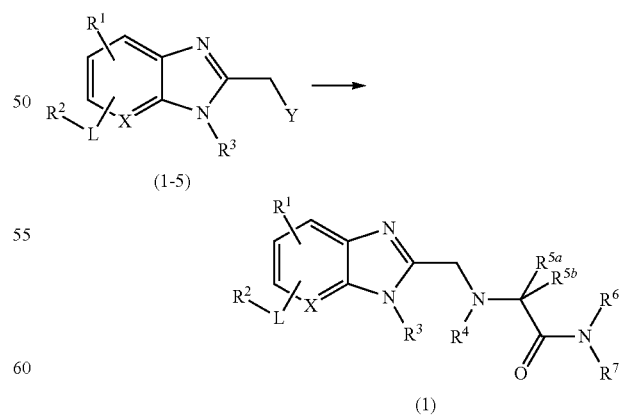

wherein $R^1$, $R^2$, $R^3$, $R^4$, $R^{5a}$, $R^{5b}$, $R^6$, $R^7$, L, Y and X are as defined above.

Compound (1) can be prepared by reacting compound (1-5) with the corresponding amine compound in the presence of a base, in a solvent such as ether solvent (e.g., tetrahydrofuran, 1,4-dioxane and the like), halogenated solvent (e.g., dichloromethane, chloroform, 1,2-dichloroethane and the like), ethyl acetate, N,N-dimethylformamide, acetonitrile and the like, at 0° C.—the refluxing temperature of the reaction solvent. While the base is not particularly limited, inorganic bases such as potassium carbonate, cesium carbonate, sodium hydroxide, sodium hydride, potassium hydride, potassium tert-butoxide and the like, and organic bases such as triethylamine, diisopropylethylamine and the like can be used.

Compound (1B), which is compound (1) wherein $R^4$ is a hydrogen atom, can be prepared, for example, by the method shown in Reaction Scheme-4 below.

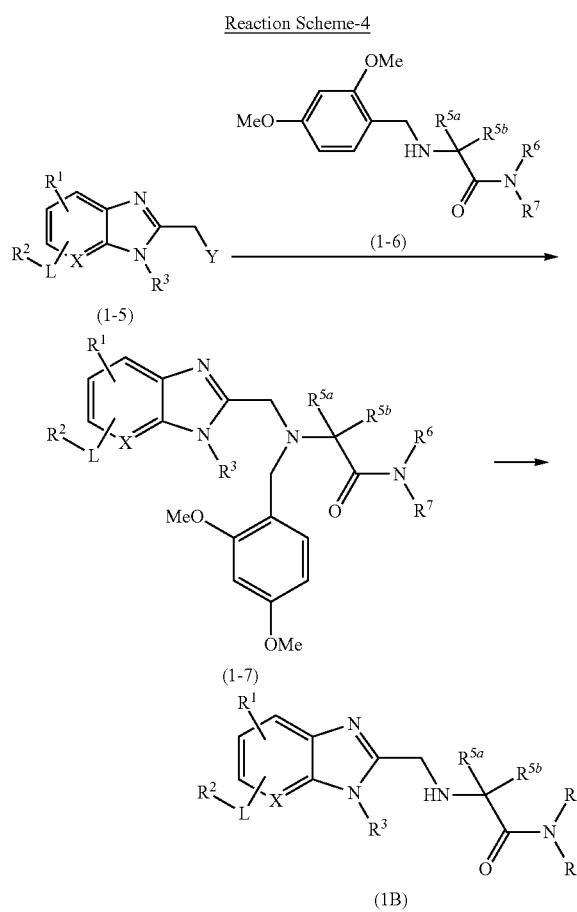

wherein $R^1$, $R^2$, $R^3$, $R^{5a}$, $R^{5b}$, $R^6$, $R^7$, L, Y and X are as defined above.

Compound (1B) can be prepared by reacting compound (1-7), which is obtained from compound (1-5) and compound (1-6) in the same manner as in Reaction Scheme-3, in an acidic solvent such as trifluoroacetic acid, trifluoromethanesulfonic acid, hydrochloric acid, sulfuric acid and the like, at room temperature—the refluxing temperature of the reaction solvent. The reaction is more preferably performed in trifluoroacetic acid at around 50° C.

The above-mentioned compounds (1-1) and (1-5) can be prepared by the method shown below and a method analogous thereto.

Of the above-mentioned compound (1-1), compound (2-1) can be prepared, for example, by the method shown in Reaction Scheme-5 below.

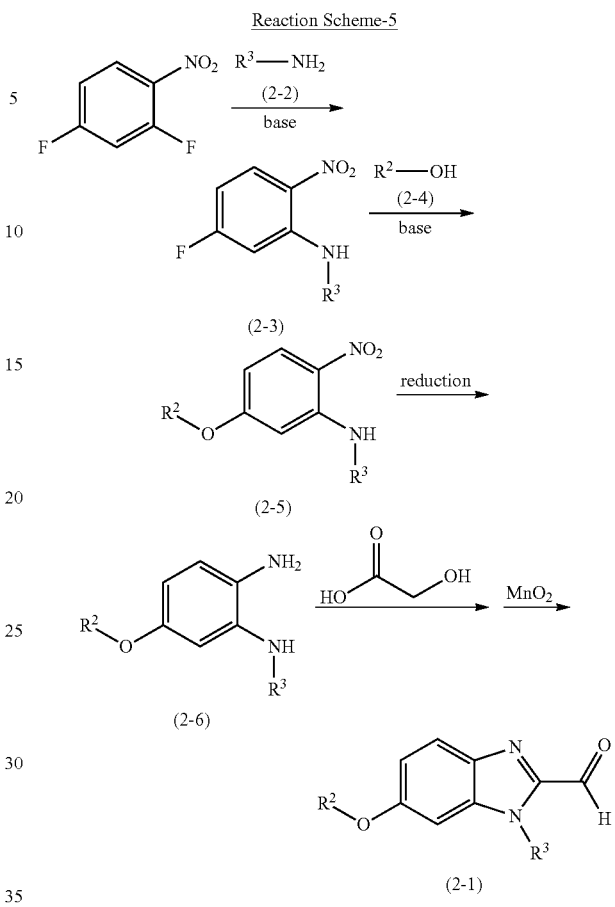

wherein $R^2$ and $R^3$ are as defined above.

Compound (2-3) can be prepared by reacting 2,4-Difluoronitrobenzene with compound (2-2) in the presence of a base, in a solvent such as ether solvent (e.g., tetrahydrofuran, dimethoxyethane, 1,4-dioxane and the like), N,N-dimethylformamide, acetonitrile and the like, at room temperature—the refluxing temperature of the reaction solvent. As the base, potassium carbonate, cesium carbonate, sodium hydroxide, sodium hydride, potassium hydride, potassium tert-butoxide and the like can be used, and potassium carbonate is preferably used. As the solvent, 1,4-dioxane is preferable.

Compound (2-5) can be prepared by reacting compound (2-3) with compound (2-4) in the presence of a base, in a solvent such as ether solvent (e.g., tetrahydrofuran, dimethoxyethane, 1,4-dioxane and the like), N,N-dimethylformamide, acetonitrile and the like, at room temperature—the refluxing temperature of the reaction solvent. As the base, potassium carbonate, cesium carbonate, sodium hydroxide, sodium hydride, potassium hydride, potassium tert-butoxide and the like can be used, and cesium carbonate is preferably used. As the solvent, 1,4-dioxane is preferable.

Compound (2-6) can be prepared by reducing the nitro group of compound (2-5) to an amino group. The reduction to be used in this reaction may be performed under conventional reduction conditions. Preferred are catalytic reduction by palladium-carbon and the like, reduction using a metal such as iron and the like, and the like. The solvent to be used for the reduction is preferably selected according to the reduction conditions. For example, for catalytic reduction, methanol, ethanol, tetrahydrofuran, ethyl acetate and the like are preferably selected and, for reduction using a metal such as iron and the like, tetrahydrofuran, acetic acid, methanol, ethanol, water and the like are selected. The catalytic reduction is preferably performed at room temperature, and the reduction using a metal such as iron and the like is preferably performed at 50° C.—the refluxing temperature of the reaction solvent.

Compound (2-1) can be prepared by mixing compound (2-6) with glycolic acid and heating them from 100° C. to 150° C., and by oxidizing the hydroxyl group of the obtained corresponding cyclic compound. The oxidation to be used for this reaction may be performed under conventional oxidation conditions. Examples thereof include oxidation with manganese dioxide, chrome and the like, and oxidation with organic oxidant represented by dimethyl sulfoxide. The oxidation with manganese dioxide and Swern oxidation are preferable. Of these, oxidation with manganese dioxide is particularly preferable. The solvent to be used for the oxidation is preferably selected according to the oxidation conditions. For example, for oxidation with a metal, halogenated solvents such as dichloromethane, chloroform and the like, and ether solvents such as tetrahydrofuran, dimethoxyethane, 1,4-dioxane and the like are preferably selected. For oxidation with an organic oxidant, halogenated solvents such as dichloromethane, chloroform and the like are preferable. The oxidation with metal is preferably performed at room temperature, and the oxidation with an organic oxidant is preferably performed at −78° C.—room temperature.

In the above-mentioned compound (1-1), compound (3-1) can also be prepared, for example, by the method shown in Reaction Scheme-6 below.

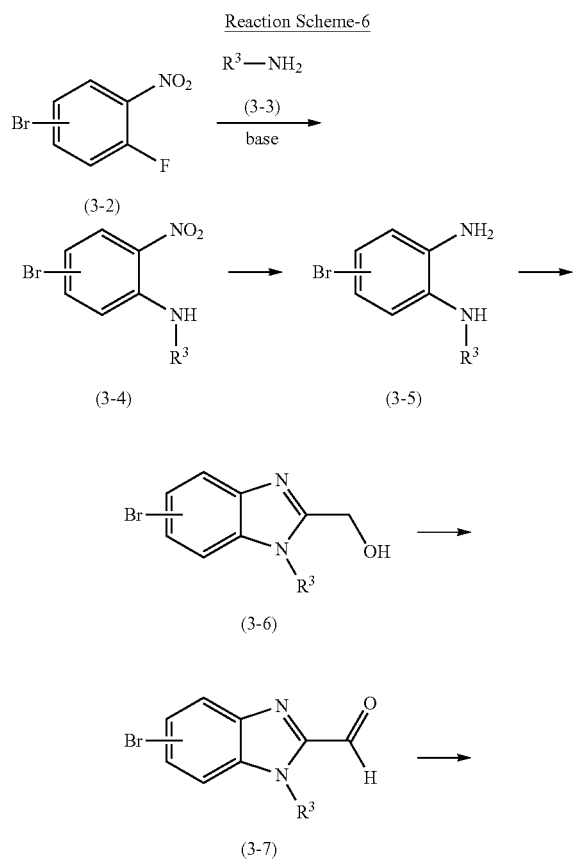

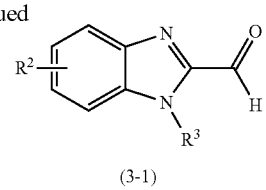

(3-1)

wherein $R^2$ and $R^3$ are as defined above.

Compound (3-4) can be prepared by reacting compound (3-2) with compound (3-3) in the presence of a base, in a solvent such as ether solvent (e.g., tetrahydrofuran, dimethoxyethane, 1,4-dioxane and the like), N,N-dimethylformamide, acetonitrile and the like, at room temperature—the refluxing temperature of the reaction solvent. As the base, potassium carbonate, cesium carbonate, sodium hydroxide, sodium hydride, potassium hydride, potassium tert-butoxide and the like can be used, and potassium carbonate is preferably used. As the solvent, 1,4-dioxane is preferable.

Compound (3-5) can be prepared by reducing the nitro group of compound (3-4) to an amino group. The reduction to be used in this reaction is preferably a reduction using a metal such as iron, tin etc., and the like. A solvent to be used for the reduction is preferably tetrahydrofuran, acetic acid, methanol, ethanol, water and the like. The reduction using a metal is preferably performed at 50° C.—the refluxing temperature of the reaction solvent.

Compound (3-6) can be prepared by mixing compound (3-5) with glycolic acid and heating them from 100° C. to 150° C. Compound (3-7) can be prepared by oxidizing the hydroxyl group of compound (3-6). The oxidation to be used for this reaction may be performed under conventional oxidation conditions. Examples thereof include oxidation with manganese dioxide, chrome and the like, and oxidation with an organic oxidant represented by dimethyl sulfoxide. The oxidation with manganese dioxide and Swern oxidation are preferable. Of these, oxidation with manganese dioxide is particularly preferable. The solvent to be used for the oxidation is preferably selected according to the oxidation conditions. For example, for oxidation with a metal, halogenated solvent such as dichloromethane, chloroform and the like, ether solvent such as tetrahydrofuran, dimethoxyethane, 1,4-dioxane and the like are preferable and, for oxidation with an organic oxidant, halogenated solvent such as dichloromethane, chloroform and the like are preferable. The oxidation with a metal is preferably performed at room temperature, and the oxidation with an organic oxidant is preferably performed at −78° C. to room temperature.

Compound (3-1) can be prepared by reacting compound (3-7) with the corresponding boranic acid compound by using a palladium catalyst, a ligand and a base, in a solvent such as dimethoxyethane, 1,4-dioxane, toluene, ethanol and the like, at room temperature—the refluxing temperature of the solvent. Examples of the palladium catalyst include, but are not particularly limited to, palladium acetate, tetrakistriphenylphosphine palladium, trisbenzylideneacetone dipalladium and the like. While the ligand is not particularly limited, examples thereof include triphenylphosphine, tri-o-tolylphosphine, tri-tert-butylphosphine and the like. While the base is not particularly limited, examples thereof include sodium carbonate, potassium carbonate, cesium carbonate and the like.

In the above-mentioned compound (1-1), compound (4-1) can be prepared, for example, according to the method shown in Reaction Scheme-7 below.

Reaction Scheme-7

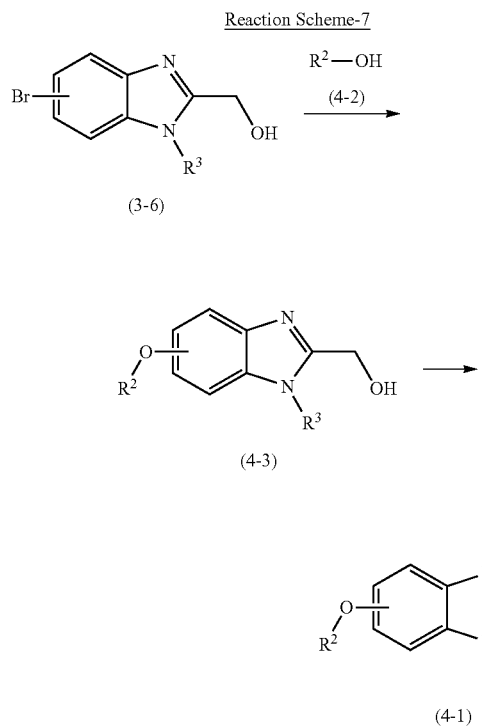

Reaction Scheme-8

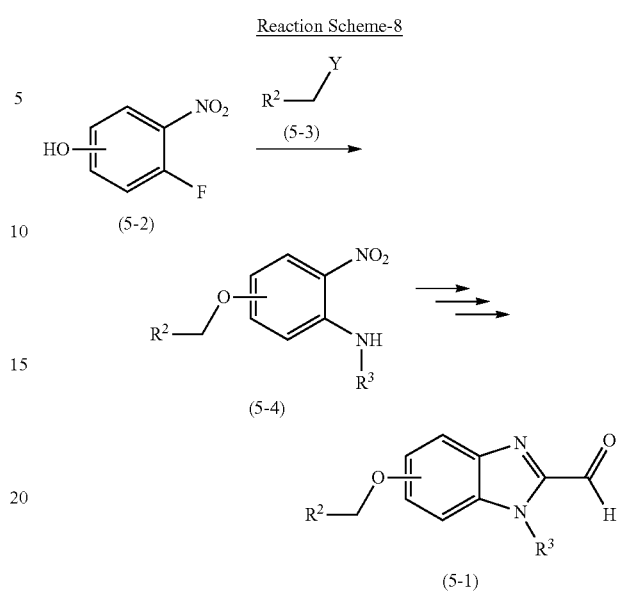

wherein $R^2$ and $R^3$ are as defined above.

Compound (4-3) can be prepared by reacting compound (3-6) with compound (4-2) by using a copper catalyst, a ligand and a base, in a solvent such as N-methylpyrrolidinone, 1,4-dioxane, dimethyl sulfoxide, N,N-dimethylformamide and the like, at room temperature—the refluxing temperature of the solvent. While the copper catalyst is not particularly limited, examples thereof include copper iodide, copper bromide, copper chloride and the like. While the ligand is not particularly limited, examples thereof include 2,2,6,6-tetramethylheptane-3,5-dione, N,N-dimethylglycine and the like. While the base is not particularly limited, examples thereof include sodium carbonate, potassium carbonate, cesium carbonate and the like.

Compound (4-1) can be prepared by oxidizing the hydroxyl group of compound (4-3). The oxidation to be used for this reaction may be performed under conventional oxidation conditions. Examples thereof include oxidation with manganese dioxide, chrome and the like, and oxidation with organic oxidant represented by dimethyl sulfoxide. The oxidation with manganese dioxide and Swern oxidation are preferable. Of these, oxidation with manganese dioxide is particularly preferable. The solvent to be used for the oxidation is preferably selected according to the oxidation conditions. For example, for oxidation with a metal, halogenated solvents such as dichloromethane, chloroform and the like, and ether solvents such as tetrahydrofuran, dimethoxyethane, 1,4-dioxane and the like are preferably selected. For oxidation with an organic oxidant, halogenated solvents such as dichloromethane, chloroform and the like are preferable. The oxidation with metal is preferably performed at room temperature, and the oxidation with an organic oxidant is preferably performed at −78° C.—room temperature.

In the above-mentioned compound (1-1), compound (5-1) can be prepared, for example, by the method shown in Reaction Scheme-8 below.

wherein $R^2$, $R^3$ and Y are as defined above.

Compound (5-4) can be prepared by reacting compound (5-2) with compound (5-3) in the presence of a base, in a solvent such as ether solvent (e.g., tetrahydrofuran, dimethoxyethane, 1,4-dioxane and the like), N,N-dimethylformamide and the like, at room temperature—the refluxing temperature of the reaction solvent. As the base, potassium carbonate, cesium carbonate, sodium hydroxide, sodium hydride, potassium hydride, potassium tert-butoxide and the like can be used, and potassium carbonate is preferably used. As the solvent, N,N-dimethylformamide is preferable.

Compound (5-1) can be obtained from compound (5-4) in the same manner as in Reaction Scheme-5.

In the above-mentioned compound (1-1), compound (6-1) can be prepared, for example, according to Reaction Scheme-9 below.

Reaction Scheme-9

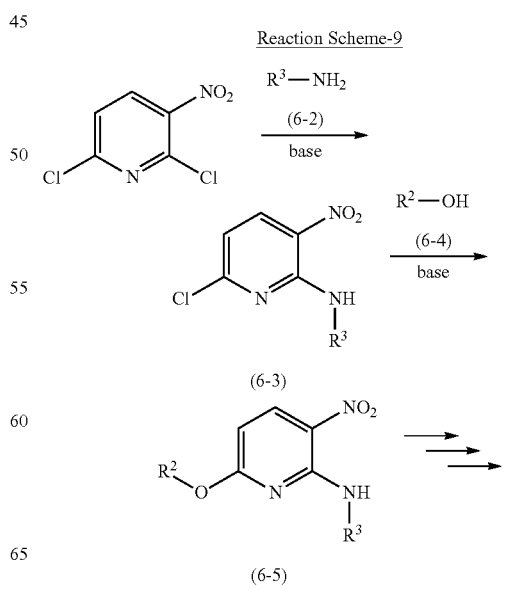

-continued

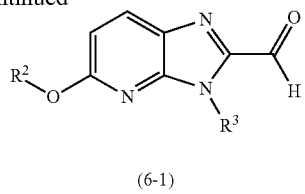

(6-1)

wherein $R^2$ and $R^3$ are as defined above.

Compound (6-3) can be prepared by reacting 2,6-Dichloro-3-nitropyridine with compound (6-2) in the presence of a base, in a solvent such as ether solvent (e.g., tetrahydrofuran, dimethoxyethane, 1,4-dioxane and the like), N,N-dimethylformamide, acetonitrile and the like, at room temperature—the refluxing temperature of the reaction solvent. As the base, potassium carbonate, cesium carbonate, sodium hydroxide, sodium hydride, potassium hydride, potassium tert-butoxide and the like can be used, and potassium carbonate is preferably used. As the solvent, 1,4-dioxane is preferable.

Compound (6-5) can be prepared by reacting compound (6-3) with compound (6-4) in the presence of a base, in a solvent such as ether solvent (e.g., tetrahydrofuran, dimethoxyethane, 1,4-dioxane and the like), N,N-dimethylformamide, acetonitrile and the like, at room temperature—the refluxing temperature of the reaction solvent. As the base, potassium carbonate, cesium carbonate, sodium hydroxide, sodium hydride, potassium hydride, potassium tert-butoxide and the like can be used, and cesium carbonate is preferably used. As the solvent, 1,4-dioxane is preferable.

Compound (6-1) can be obtained from compound (6-5) in the same manner as in Reaction Scheme-5.

In the above-mentioned compound (1-1), compound (7-1) can be prepared, for example, by the method shown in Reaction Scheme-10 below.

Reaction Scheme-10

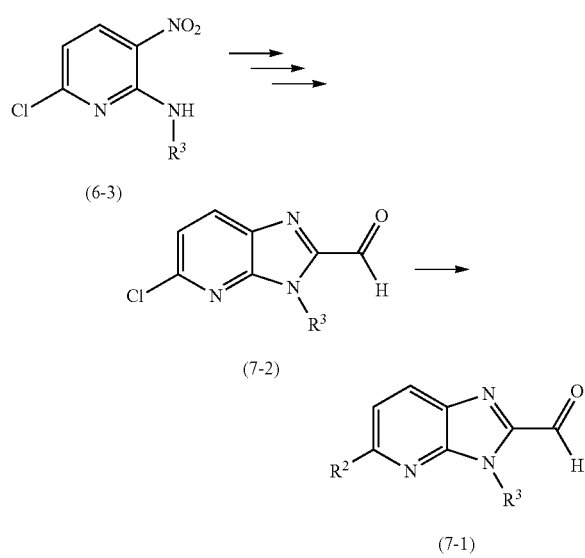

wherein $R^2$ and $R^3$ are as defined above.

Compound (7-2) can be obtained from compound (6-3) in the same manner as in Reaction Scheme-6.

Compound (7-1) can be prepared by reacting compound (7-2) with the corresponding boranic acid compound by using a palladium catalyst, a ligand and a base, in a solvent such as dimethoxyethane, 1,4-dioxane, toluene, ethanol and the like, at room temperature—the refluxing temperature of the solvent. Examples of the palladium catalyst include, but are not particularly limited to, palladium acetate, tetrakistriphenylphosphine palladium, trisbenzylideneacetone dipalladium and the like. While the ligand is not particularly limited, examples thereof include triphenylphosphine, tri-o-tolylphosphine, tri-tert-butylphosphine and the like. While the base is not particularly limited, examples thereof include sodium carbonate, potassium carbonate, cesium carbonate and the like.

The above-mentioned compound (1-5) can be prepared from compound (8-1), for example, by the method shown in Reaction Scheme-11 below.

Reaction Scheme-11

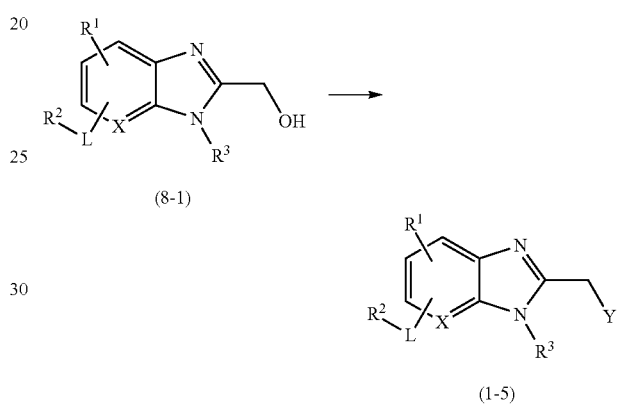

wherein $R^1$, $R^2$, $R^3$, L, X and Y are as defined above.

As a conversion step to a leaving group, when the leaving group Y is a mesyloxy group or a tosyloxy group, corresponding chloride (mesyl chloride, tosyl chloride) is reacted in the presence of a base such as triethylamine, pyridine and the like to give corresponding mesyl or tosyl form. When the leaving group Y is a halogen atom, the methods described in Comprehensive Organic Transformation [R. C. Larock, VCH Publishers Inc. (1989)], 4th Edition Jikken Kagaku Kouza (Maruzen), Shinjikken Kagaku Koza (Courses in Experimental Chemistry) (Maruzen) and the like can be employed. For example, corresponding bromide can be obtained by adding phosphorus tribromide in tetrahydrofuran.

Each of the aforementioned reactions can be performed according to the methods described in the Examples of the present specification, Comprehensive Organic Transformation [R. C. Larock, VCH Publishers Inc. (1989)], 4th Edition Jikken Kagaku Kouza (Maruzen), Shinjikken Kagaku Koza (Courses in Experimental Chemistry) (Maruzen).

In addition, the starting material compounds to be used in the aforementioned production methods can be appropriately prepared by using a commercially available product or according to a method known to those of ordinary skill in the art.

Furthermore, when the compound of the present invention or a pharmaceutically acceptable salt thereof is prepared, a functional group such as a hydroxyl group, a carboxyl group, an amino group and the like can be protected or deprotected in any step where necessary. The kind of the protecting group and the method of protection and deprotection may be those well known to those of ordinary skill in the art. For example, "Protective Groups in Organic Synthesis (T. W. Greene et al., John Wiley & Sons, Inc. published in 1991)" and the like may be referred to.

When compound (1) has a group capable of forming a salt in the structure, it can be converted as necessary to an acid addition salt with inorganic acid or organic acid, or an alkali addition salt, which is acceptable as a medicament. Examples of the pharmaceutically acceptable acid addition salt include inorganic acid salts such as hydrochloride, hydrobromide, sulfate, phosphate and the like, salts with organic carboxylic acid such as formate, acetate, fumarate, maleate, oxalate, citrate, malate, tartrate, aspartate, glutamate and the like, salts with sulfonic acid such as methanesulfonate, benzenesulfonate, p-toluenesulfonate, hydroxybenzenesulfonate, dihydroxybenzenesulfonate and the like, and examples of the pharmaceutically acceptable alkali addition salt include ammonium salt, lithium salt, sodium salt, potassium salt, calcium salt, magnesium salt and the like.

In addition, the present invention also encompasses a hydrate, and a solvate such as ethanolate and the like, of compound (1) or a pharmaceutically acceptable salt thereof. Furthermore, the present invention encompasses any tautomer and stereoisomer such as optical isomer and the like, and any crystalline form, of compound (1). These can be appropriately purified by a method well known to those of ordinary skill in the art, such as silica gel column chromatography, HPLC, ion exchange chromatography, recrystallization and the like.

To obtain the aforementioned optical isomer in a pure form, an optical resolution method known to those of ordinary skill in the art may be used. To be specific, when the compound of the present invention or an intermediate thereof has a basic functional group, it can form a salt with an optically active acid (e.g., monocarboxylic acids such as mandelic acid, N-benzyloxyalanine, lactic acid and the like, dicarboxylic acids such as tartaric acid, o-diisopropylidenetartaric acid, malic acid and the like, sulfonic acids such as camphorsulfonic acid, bromocamphorsulfonic acid and the like) in an inert solvent. In addition, when the compound of the present invention or an intermediate thereof has an acidic functional group, it can also form a salt with optically active amine (e.g., organic amines such as α-phenethylamine, kinin, quinidine, cinchonidine, cinchonine, strychnine and the like). The temperature for the formation of the salt is from room temperature to the boiling point of the solvent.

The novel compound having a bicyclic heterocycle of the present invention or a pharmaceutically acceptable salt thereof has an SNS inhibitory activity and can be used as a therapeutic or prophylactic drug for neuropathic pain and nociceptive pain. Examples of the neuropathic pain here include neuralgia after lumbar operation, diabetic neuropathy, neuralgia after herpes zoster, reflex sympathetic dystrophy, phantom limb pain, spinal cord injury, late stage carcinomatous pain and prolonged postoperative pain. Examples of the nociceptive pain include lumbago, abdominal pain, rheumatoid arthritis, pain due to osteoarthritis and the like. In addition, the compound of the present invention or a pharmaceutically acceptable salt thereof can also be used as a therapeutic or prophylactic drug for dysuria. Examples of the dysuria here include frequent urination, cystalgia due to benign prostatic hyperplasia and the like. Furthermore, it can also be used as a therapeutic or prophylactic drug for suppressing abnormal nervous firing in the cerebellum in multiple sclerosis. As a medicament free of side effects derived from nonneural tissue or central nervous system, a compound having an SNS-selective inhibitory activity is more preferable.

The therapeutic or prophylactic drug of the present invention for neuropathic pain, nociceptive pain, dysuria or multiple sclerosis can contain various additional components for preparation such as conventional carrier, binder, stabilizer, excipient, diluent, pH buffering agent, disintegrant, solubilizer, dissolution aid, isotonic agent and the like, which are pharmaceutically acceptable. In addition, these therapeutic or prophylactic drugs can be orally or parenterally administered. That is, for oral administration, the drug can be orally administered in the form generally employed, for example, in dosage forms such as tablet, pill, powder, granule, capsule, syrup, emulsion, suspension and the like. For parenteral administration, the drug can be formulated as a preparation in the form of, for example, intravenous injection (drip infusion), intramuscular injection, subcutaneous injection, embrocation, eye drop, ophthalmic ointment and the like.

A solid preparation such as tablet is prepared by mixing the active ingredient with generally pharmacologically acceptable carrier or excipient such as lactose, sucrose, cornstarch and the like, binder such as crystalline cellulose, hydroxypropylcellulose, polyvinylpyrrolidone, hydroxypropylmethylcellulose and the like, disintegrant such as carboxymethylcellulose sodium, starch sodium glycolate and the like, lubricant such as stearic acid, magnesium stearate and the like, preservative and the like.

For parenteral administration, the active ingredient may be dissolved or suspended in physiologically acceptable carrier such as water, saline, oil, aqueous glucose solution and the like, and may be added with emulsifier, stabilizer, salt for adjusting osmotic pressure or buffering agent as aids, where necessary.

The preparation of the compound of the present invention can be prepared according to a conventional method. For example, a tablet can be prepared by mixing the compound of Example 1 (20 mg), lactose (100 mg), crystalline cellulose (25 mg) and magnesium stearate (1 mg), and tableting the obtained mixture.

While the dose and frequency of administration vary depending on the administration method, and age, body weight, the disease state and the like of patients, a method of topical administration to a disease-injury lesion part is preferable. It is also preferable to administer the drug once or twice or more per day. When administering twice or more, consecutive administration or repeat administration at suitable intervals is desirable.

The dose is 10 μg-2 g, preferably 1 mg-1 g, more preferably 10-100 mg, in the amount of the active ingredient for an adult patient per single administration, which can be administered at once or in several portions a day. For parenteral administration, the dose can be 0.1-100 mg/day, more preferably 0.3-50 mg/day, for an adult patient, which can be administered at once or in several portions a day. To reduce administration frequency, a sustained-release preparation can also be used.

In addition, the therapeutic or prophylactic drug of the present invention for neuropathic pain, nociceptive pain, dysuria or multiple sclerosis can also be utilized as an animal drug.

EXAMPLES

The present invention is explained in more detail in the following by referring to Reference Examples and Examples; however, the technical scope of the present invention is not limited to such Examples and the like. The compounds were identified by hydrogen nuclear magnetic resonance absorption spectrum ($^1$H-NMR) and the like.

In the following, abbreviations shown below may be used sometimes to simplify the description of the present specification.

Me: methyl, Et: ethyl, Pr: propyl, iPr: isopropyl, Ph: phenyl, Ac: acetyl, Boc: tert-butoxycarbonyl, Bn: benzyl, TBDMS: tert-butyldimethylsilyl, PyBOP: benzotriazol-1-yloxy-tris(pyrrolidino)phosphonium hexafluorophosphate, J: binding constant, s: singlet, d: doublet, dd: double doublet, ddd: 4 doublets, td: 3 doublets, t: triplet, dt: double triplet, q: quartet, quint: quintet, br: broad, m: multiplet.

Unless otherwise specified, the starting material compounds, reaction reagents and solvents used were commercially available products.

Reference Example 1

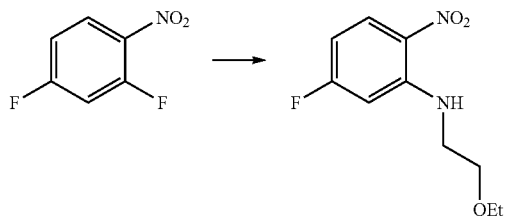 [SMILES: O=[N+]([O-])c1ccc(F)cc1F ; CCOCCNc1cc(F)ccc1[N+](=O)[O-]]

To a solution of 2,4-difluoronitrobenzene (15 g, 94 mmol) in dioxane (300 mL) were added potassium carbonate (14.4 g, 104 mmol) and 2-ethoxyethylamine (8.4 g, 104 mmol), and the mixture was stirred at room temperature overnight. Water was added to the reaction mixture, and the mixture was extracted with ethyl acetate. The organic layer was washed with water and saturated brine, dried over sodium sulfate, and concentrated under reduced pressure to give the object product (21 g, 98%).

$^1$H-NMR (CDCl$_3$) δ 1.25 (t, J=7.1 Hz, 3H), 3.43 (q, J=5.2 Hz, 2H), 3.58 (q, J=7.1 Hz, 2H), 3.72 (t, J=5.2 Hz, 2H), 6.37 (ddd, J=9.5, 7.3, 2.5 Hz, 1H), 6.51 (dd, J=11.5, 2.5 Hz, 1H), 8.22 (dd, J=9.5, 6.1 Hz, 1H), 8.38 (br, 1H).

Reference Example 2

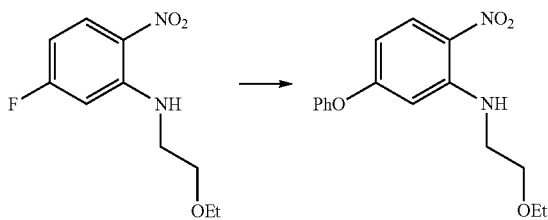 [SMILES: CCOCCNc1cc(F)ccc1[N+](=O)[O-] ; CCOCCNc1cc(Oc2ccccc2)ccc1[N+](=O)[O-]]

To a solution (60 mL) of the compound (3.0 g, 13.2 mmol) obtained in Reference Example 1 in dioxane were added cesium carbonate (6.4 g, 19.7 mmol) and phenol (1.5 g, 15.8 mmol), and the mixture was heated to 80° C. After stirring for 7 hr, water was added to the reaction mixture, and the mixture was extracted with ethyl acetate. The organic layer was washed with water and saturated brine, dried over sodium sulfate, and concentrated under reduced pressure to give the object product (4.1 g, 100%).

$^1$H-NMR (CDCl$_3$) δ 1.23 (t, J=7.0 Hz, 3H), 3.34 (q, J=5.2 Hz, 2H), 3.55 (q, J=7.0 Hz, 2H), 3.67 (t, J=5.2 Hz, 2H), 6.22 (dd, J=9.4, 2.5 Hz, 1H), 6.29 (d, J=2.5 Hz, 1H), 7.07-7.12 (m, 2H), 7.23 (m, 1H), 7.35-7.45 (m, 2H), 8.16 (d, J=9.4 Hz, 1H), 8.39 (br, 1H).

Reference Example 3-1

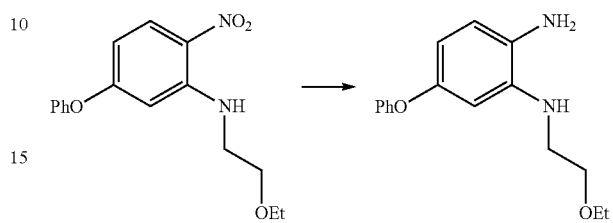

To a solution (50 mL) of the compound (1.8 g, 6.0 mmol) obtained in Reference Example 2 in ethanol was added 10% palladium-carbon (1 g), and the mixture was stirred at room temperature for 4 hr under a hydrogen atmosphere. The reaction mixture was filtered through celite, and the filtrate was concentrated and dried under reduced pressure to give the object product (1.4 g, 86%).

$^1$H-NMR (CDCl$_3$) δ 1.22 (t, J=7.0 Hz, 3H), 3.21 (t, J=5.2 Hz, 2H), 3.23 (br, 2H), 3.53 (q, J=7.0 Hz, 2H), 3.67 (t, J=5.2 Hz, 2H), 6.34 (dd, J=8.3, 2.6 Hz, 1H), 6.40 (d, J=2.6 Hz, 1H), 6.67 (d, J=8.3 Hz, 1H), 6.92-7.04 (m, 3H), 7.24-7.30 (m, 2H).

Reference Example 3-2

The above-mentioned object product can also be prepared by the following method.

To a suspension (3:2:1, 120 mL) of iron (13.9 g, 0.25 mol) and ammonium chloride (6.6 g, 0.12 mol) in tetrahydrofuran-methanol-water was added dropwise a solution (60 mL) of the compound (9.8 g, 32 mmol) obtained in Reference Example 2 in a mixed solvent (3:2:1) of tetrahydrofuran-methanol-water while refluxing under heating. After stirring for 2 hr, the reaction mixture was allowed to cool, and filtered through celite. Water was added to the filtrate, and the mixture was extracted with ethyl acetate. The organic layer was washed with water and saturated brine, dried over sodium sulfate, and concentrated under reduced pressure to give the object product (8.7 g, 100%).

Reference Example 4

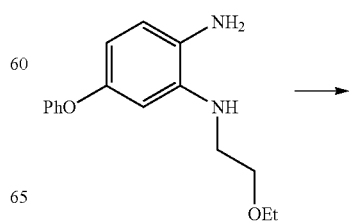

-continued

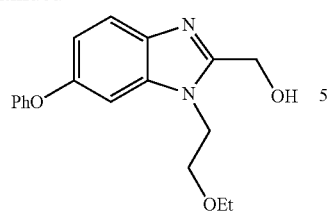

To the compound (5.0 g, 18.4 mmol) obtained in Reference Example 3 was added glycolic acid (8 g), and the mixture was stirred at 120° C. for 30 min. After cooling, water and chloroform were added to the reaction mixture, and the mixture was neutralized with 30% aqueous sodium hydroxide solution under ice-cooling. The organic layer was extracted, dried over sodium sulfate, and concentrated under reduced pressure. The residue was purified by silica gel column (chloroform:methanol=50:1-30:1) to give the object crude product (4.1 g).

Reference Example 5

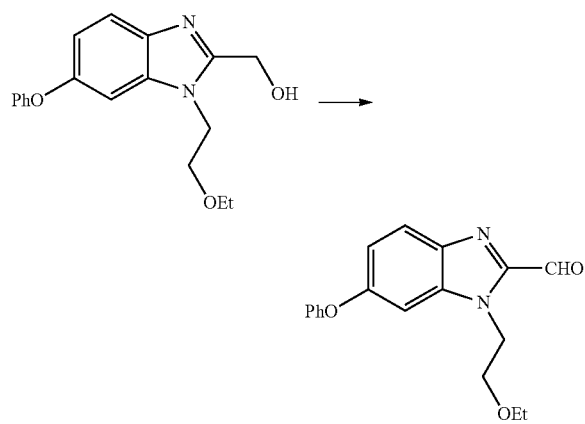

To a solution of the compound (4.1 g) obtained in Reference Example 4 in dichloromethane (100 mL) was added manganese dioxide (8 g), and the mixture was stirred at room temperature. After stirring for 2 hr, the reaction mixture was filtered through celite, and the filtrate was concentrated. The residue was purified by silica gel column (ethyl acetate:hexane=1:2) to give the object product (3.5 g, 61%, 2 steps).

$^1$H-NMR (CDCl$_3$) δ 1.03 (t, J=7.0 Hz, 3H), 3.37 (q, J=7.0 Hz, 2H), 3.73 (t, J=5.3 Hz, 2H), 4.66 (t, J=5.3 Hz, 2H), 7.04-7.20 (m, 5H), 7.34-7.41 (m, 2H), 7.86 (d, J=8.8 Hz, 1H), 10.05 (s, 1H).

Reference Example 6

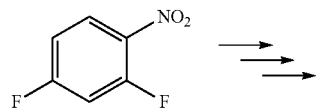

-continued

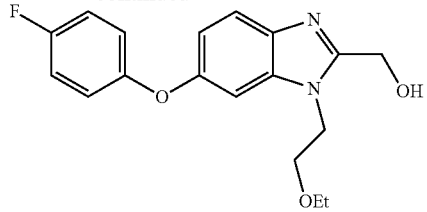

The object crude product obtained from 2,4-difluoronitrobenzene (20.0 g, 126 mmol) and 4-fluorophenol in the same manner as in Reference Examples 1-4 was recrystallized from chloroform/hexane and further recrystallized from acetonitrile to give the object product (23.3 g, 56%, 4 steps).

$^1$H-NMR (CDCl$_3$) δ 1.05 (t, J=7.0 Hz, 3H), 3.37 (q, J=7.0 Hz, 2H), 3.70 (t, J=5.1 Hz, 2H), 4.34 (t, J=5.1 Hz, 2H), 4.89 (s, 2H), 6.89-7.03 (m, 6H), 7.58 (m, 1H).

Reference Example 7

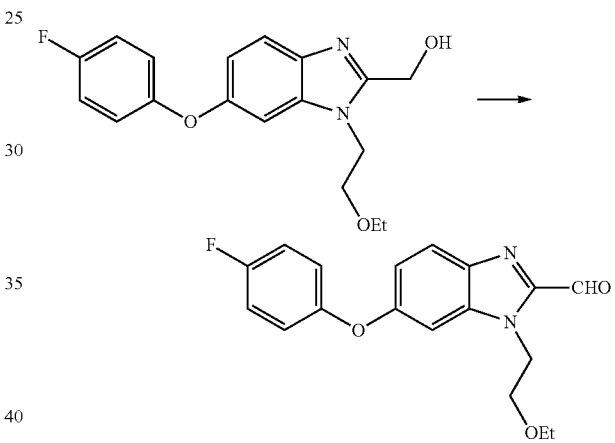

The object product was obtained in the same manner as in Reference Example 5 from the compound obtained in Reference Example 6.

$^1$H-NMR (CDCl$_3$) δ 0.99 (t, J=7.0 Hz, 3H), 3.33 (q, J=7.0 Hz, 2H), 3.69 (t, J=5.1 Hz, 2H), 4.62 (t, J=5.1 Hz, 2H), 6.92-7.09 (m, 6H), 7.81 (m, 1H), 10.00 (s, 1H).

Example 1

N$^2$-{[1-(2-ethoxyethyl)-6-phenoxy-1H-benzimidazol-2-yl]methyl}-L-alaninamide

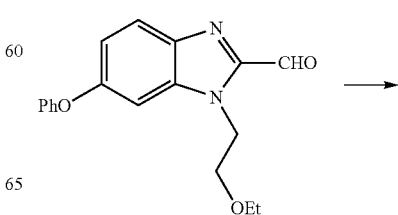

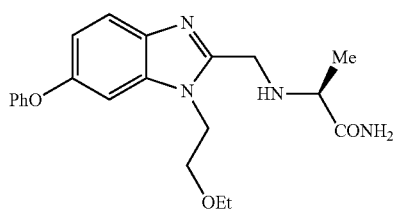

To a solution of the compound (2.0 g, 6.5 mmol) obtained in Reference Example 5 in dichloromethane (50 mL) was added (L)-alaninamide hydrochloride (0.96 g, 7.7 mmol), and the mixture was stirred at room temperature. After stirring for 1 hr, sodium triacetoxyborohydride (1.6 g, 7.7 mmol) was added thereto, and the mixture was stirred for 2 hr. The reaction mixture was poured into saturated aqueous sodium hydrogen carbonate solution, and the mixture was extracted with ethyl acetate. The organic layer was extracted, washed with water and saturated brine, dried over sodium sulfate, and concentrated under reduced pressure. The residue was purified by silica gel column (chloroform:methanol=50:1-10:1) to give the object product (0.59 g, 24%).

$^1$H-NMR (CDCl$_3$) δ 1.08 (t, J=7.1 Hz, 3H), 1.41 (d, J=7.0 Hz, 3H), 3.33 (q, J=7.0 Hz, 1H), 3.38 (q, J=7.1 Hz, 2H), 3.68 (t, J=5.1 Hz, 2H), 4.04 (d, J=14.7 Hz, 1H), 4.12 (d, J=14.7 Hz, 1H), 4.17-4.32 (m, 2H), 5.50 (brs, 1H), 6.98-7.02 (m, 4H), 7.09 (m, 1H), 7.28-7.36 (m, 3H), 7.68 (m, 1H).

The above-mentioned compound can also be prepared by the following method.

To a solution of the compound (0.15 g, 0.48 mmol) obtained in Reference Example 5 in tetrahydrofuran (10 mL) were added (L)-alaninamide hydrochloride (0.18 g, 1.45 mmol), sodium sulfate (3 g) and triethylamine (0.20 mL), and the mixture was stirred at room temperature. After stirring for 30 min, sodium cyanoborohydride (45 mg, 0.72 mmol) was added thereto, and the mixture was stirred for 2 hr. The reaction mixture was poured into saturated aqueous sodium hydrogen carbonate solution, and the mixture was extracted with chloroform. The organic layer was extracted, washed with saturated brine, dried over sodium sulfate, and concentrated under reduced pressure. The residue was purified by silica gel column (chloroform:methanol=50:1-10:1) to give the object product (0.09 g, 49%).

Example 2

N$^2$-{[1-(2-ethoxyethyl)-6-phenoxy-1H-benzimidazol-2-yl]methyl}glycinamide

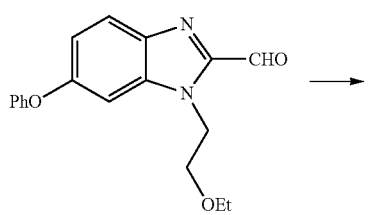

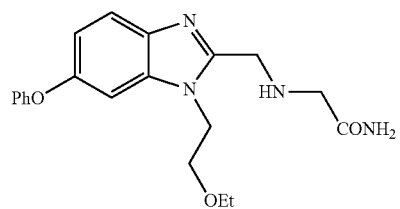

To a solution of the compound (44 mg, 0.14 mmol) obtained in Reference Example 5 in methanol (3 ml) was added glycinamide hydrochloride (31 mg, 0.28 mmol), and the mixture was stirred at room temperature. After stirring for 1 hr, sodium cyanoborohydride (18 mg, 0.28 mmol) was added thereto, and the mixture was stirred overnight. The reaction mixture was poured into saturated aqueous sodium hydrogen carbonate solution, and the mixture was extracted with ethyl acetate. The organic layer was extracted, washed with water and saturated brine, dried over sodium sulfate, and concentrated under reduced pressure. The residue was purified by silica gel column (chloroform:methanol=50:1-10:1) to give the object product (23 mg, 43%).

$^1$H-NMR (CDCl$_3$) δ 1.08 (t, J=7.0 Hz, 3H), 3.38 (q, J=7.0 Hz, 2H), 3.42 (s, 2H), 3.68 (t, J=5.1 Hz, 2H), 4.10 (s, 2H), 4.26 (t, J=5.1 Hz, 2H), 5.72 (brs, 1H), 6.96-7.02 (m, 4H), 7.08 (m, 1H), 7.21 (brs, 1H), 7.28-7.36 (m, 2H), 7.68 (m, 1H).

Example 3

N$^2$-{[1-(2-ethoxyethyl)-6-(4-fluorophenoxy)-1H-benzimidazol-2-yl]methyl}glycinamide

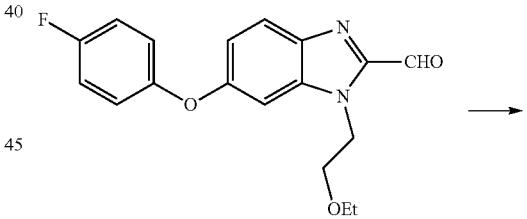

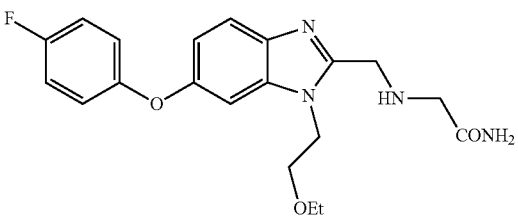

The object product was obtained in the same manner as in Example 2 from the compound obtained in Reference Example 7.

$^1$H-NMR (CDCl$_3$) δ 1.09 (t, J=7.0 Hz, 3H), 3.39 (q, J=7.0 Hz, 2H), 3.42 (s, 2H), 3.69 (t, J=5.0 Hz, 2H), 4.10 (s, 2H), 4.26 (t, J=5.0 Hz, 2H), 5.54 (brs, 1H), 6.93-7.05 (m, 6H), 7.18 (brs, 1H), 7.67 (m, 1H).

Example 4

N$^2$-{[1-(2-ethoxyethyl)-6-(4-fluorophenoxy)-1H-benzimidazol-2-yl]methyl}-L-valinamide

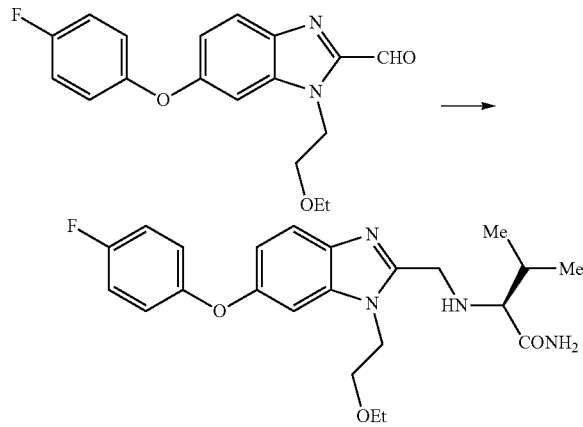

The object product was obtained in the same manner as in Example 1 from the compound obtained in Reference Example 7 and (L)-valinamide hydrochloride.

$^1$H-NMR (CDCl$_3$) δ 0.99 (d, J=7.0 Hz, 3H), 1.02 (d, J=7.0 Hz, 3H), 1.08 (t, J=7.0 Hz, 3H), 2.08 (m, 1H), 2.97 (d, J=5.5 Hz, 1H), 3.38 (q, J=7.0 Hz, 2H), 3.68 (t, J=5.1 Hz, 2H), 3.98 (d, J=14.5 Hz, 1H), 4.15 (d, J=14.5 Hz, 1H), 4.17-4.40 (m, 2H), 5.56 (brs, 1H), 6.93-7.01 (m, 7H), 7.67 (m, 1H).

Example 5

N$^2$-{[1-(2-ethoxyethyl)-6-(4-fluorophenoxy)-1H-benzimidazol-2-yl]methyl}-2-methylalaninamide

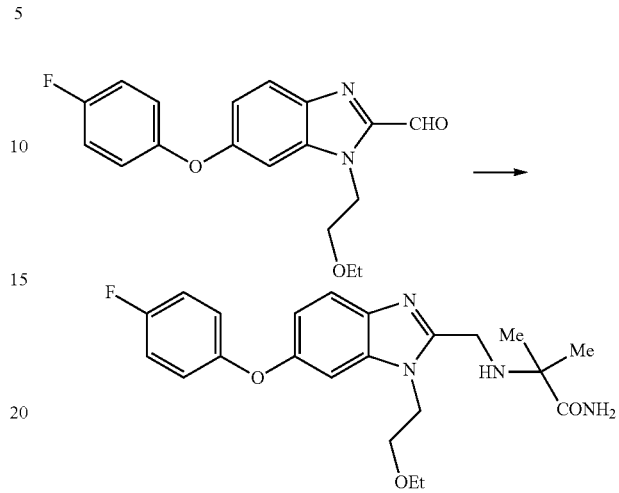

The object product was obtained in the same manner as in Example 1 from the compound obtained in Reference Example 7 and 2-methylalaninamide which is a known compound.

$^1$H-NMR (CDCl$_3$) δ 1.09 (t, J=7.0 Hz, 3H), 1.46 (s, 6H), 3.38 (q, J=7.0 Hz, 2H), 3.69 (t, J=5.1 Hz, 2H), 4.02 (s, 2H), 4.24 (t, J=5.1 Hz, 2H), 5.43 (brs, 1H), 6.93-7.05 (m, 6H), 7.48 (brs, 1H), 7.68 (m, 1H).

Examples 6-58

The compounds of Examples 6-58 shown in Table 1-Table 9 were prepared in the same manner as in Reference Examples 1-7, Example 1 or Example 2 from 2,4-difluoronitrobenzene and using commercially available or known compounds.

TABLE 1

| Example | structural formula | $^1$H-NMR(CDCl$_3$) δ |
|---|---|---|
| 6 | (structure: 4-fluorophenoxy-benzimidazole with N-tetrahydropyranyl and CH$_2$NH-CH(CH$_3$)-C(O)NH$_2$) | 1.40 (d, J = 7.0 Hz, 3H), 1.79-1.88 (m, 2H), 2.42-2.58 (m, 2H), 3.28 (q, J = 7.0 Hz, 1H), 3.51-3.58 (m, 2H), 4.03 (d, J = 14.8 Hz, 1H), 4.11 (d, J = 14.8 Hz, 1H), 4.13-4.19 (m, 2H), 4.48 (m, 1H), 5.45 (brs, 1H), 6.91-7.05 (m, 6H), 7.26 (brs, 1H), 7.67 (d, J = 8.8 Hz, 1H). |
| 7 | (structure: 4-fluorophenoxy-benzimidazole with N-cyclopropyl and CH$_2$NH-CH(CH$_3$)-C(O)NH$_2$) | 0.98-1.05 (m, 2H), 1.15-1.27 (m, 2H), 1.44 (d, J = 7.0 Hz, 3H), 3.18 (m, 1H), 3.35 (q, J = 7.0 Hz, 1H), 4.09 (d, J = 15.6 Hz, 1H), 4.17 (d, J = 15.6 Hz, 1H), 5.35 (brs, 1H), 6.91-7.05 (m, 5H), 7.14 (d, J = 2.4 Hz, 1H), 7.25 (brs, 1H), 7.63 (d, J = 8.8 Hz, 1H). |

TABLE 1-continued

| Example | structural formula | ¹H-NMR(CDCl₃) δ |
|---|---|---|
| 8 | (4-fluorophenoxy-benzimidazole with tetrahydropyran N-substituent, CH₂-NH-C(CH₃)₂-C(O)NH₂) | 1.47 (s, 6H), 1.80-1.86 (m, 2H), 2.44-2.58 (m, 2H), 3.50-3.59 (m, 2H), 4.01 (s, 2H), 4.14-4.19 (m, 2H), 4.43 (m, 1H), 5.84 (brs, 1H), 6.90-7.04 (m, 5H), 7.16 (brs, 1H), 7.26 (d, J = 2.0 Hz, 1H), 7.66 (d, J = 8.8 Hz, 1H). |
| 9 | (phenoxy-benzimidazole with isopropyl N-substituent, CH₂-NH-CH(CH₃)-C(O)NH₂) | 1.40 (d, J = 7.0 Hz, 3H), 1.58 (d, J = 7.0 Hz, 6H), 3.30 (q, J = 7.0 Hz, 1H), 4.01 (d, J = 14.7 Hz, 1H), 4.08 (d, J = 14.7 Hz, 1H), 4.69 (m, 1H), 6.10 (brs, 1H), 6.92-7.02 (m, 3H), 7.07 (m, 1H), 7.15 (brs, 1H), 7.21 (m, 1H), 7.27-7.37 (m, 2H), 7.65 (d, J = 8.6 Hz, 1H). |
| 10 | (phenoxy-benzimidazole with isopropyl N-substituent, CH₂-NH-CH₂-C(O)NH₂) | 1.58 (d, J = 7.0 Hz, 6H), 3.43 (s, 2H), 4.07 (s, 2H), 4.69 (m, 1H), 6.15 (brs, 1H), 6.91-7.01 (m, 4H), 7.04 (m, 1H), 7.11 (brs, 1H), 7.20 (d, J = 1.9 Hz, 1H), 7.29-7.36 (m, 2H), 7.64 (d, J = 8.8 Hz, 1H). |
| 11 | (phenoxy-benzimidazole with cyclobutyl N-substituent, CH₂-NH-CH(CH₃)-C(O)NH₂) | 1.42 (d, J = 7.0 Hz, 3H), 1.82-2.04 (m, 2H), 2.44-2.58 (m, 2H), 2.76-2.91 (m, 2H), 3.30 (q, J = 7.0 Hz, 1H), 3.99 (d, J = 14.1 Hz, 1H), 4.06 (d, J = 14.1 Hz, 1H), 4.87 (m, 1H), 5.52 (brs, 1H), 6.94-7.11 (m, 4H), 7.13 (brs, 1H), 7.30-7.37 (m, 3H), 7.66 (d, J = 8.8 Hz, 1H). |

TABLE 2

| Example | structural formula | ¹H-NMR(CDCl₃) δ |
|---|---|---|
| 12 | (phenoxy-benzimidazole with cyclobutyl N-substituent, CH₂-NH-CH₂-C(O)NH₂) | 1.88-2.04 (m, 2H), 2.46-2.59 (m, 2H), 2.76-2.92 (m, 2H), 3.44 (s, 2H), 4.05 (s, 2H), 4.88 (m, 1H), 5.50 (brs, 1H), 6.95-7.12 (m, 5H), 7.30-7.36 (m, 3H), 7.66 (d, J = 8.8 Hz, 1H). |
| 13 | (phenoxy-benzimidazole with tetrahydropyran-4-ylmethyl N-substituent, CH₂-NH-CH(CH₃)-C(O)NH₂) | 1.30-1.54 (m, 4H), 1.43 (d, J = 6.8 Hz, 3H), 2.06 (m, 1H), 3.22-3.37 (m, 3H), 3.86-4.10 (m, 6H), 5.51 (brs, 1H), 6.96-7.13 (m, 6H), 7.29-7.35 (m, 2H), 7.67 (m, 1H). |

TABLE 2-continued

| Example | structural formula | $^1$H-NMR(CDCl$_3$) δ |
|---|---|---|
| 14 | (benzimidazole with phenoxy at 6-position, N-CH2-(tetrahydropyran-4-yl), 2-CH2-NH-CH2-C(=O)NH2) | 1.32-1.54 (m, 4H), 2.06 (m, 1H), 3.30 (td, J = 11.5, 2.6 Hz, 2H), 3.45 (s, 2H), 3.92-4.00 (m, 4H), 4.06 (s, 2H), 5.57 (brs, 1H), 6.96-7.12 (m, 6H), 7.30-7.37 (m, 2H), 7.67 (m, 1H). |
| 15 | (benzimidazole with 4-fluorophenoxy at 6-position, N-CH2CH2-O-CH2CH3, 2-CH2-prolinamide) | 1.08 (t, J = 7.0 Hz, 3H), 1.78-2.05 (m, 3H), 2.29 (m, 1H), 2.60 (m, 1H), 3.16 (m, 1H), 3.28-3.42 (m, 3H), 3.70 (t, J = 5.2 Hz, 2H), 3.94 (d, J = 14.3 Hz, 1H), 4.21 (d, J = 14.3 Hz, 1H), 4.27-4.38 (m, 2H), 5.39 (brs, 1H), 6.93-7.06 (m, 6H), 7.64 (brs, 1H), 7.68 (d, J = 9.4 Hz, 1H). |
| 16 | (benzimidazole with phenoxy at 6-position, N-CH2-(tetrahydropyran-4-yl), 2-CH2-prolinamide) | 1.32-1.52 (m, 4H), 1.80-2.35 (m, 5H), 2.59 (q, J = 8.4 Hz, 1H), 3.20-3.36 (m, 4H), 3.88-4.18 (m, 6H), 5.50 (brs, 1H), 6.96-7.12 (m, 5H), 7.28-7.38 (m, 2H), 7.44 (brs, 1H), 7.68 (m, 1H). |
| 17 | (benzimidazole with 4-fluorophenoxy at 6-position, N-cyclobutyl, 2-CH2-NH-CH(CH3)-C(=O)NH2) | 1.42 (d, J = 6.8 Hz, 3H), 1.86-2.04 (m, 2H), 2.47-2.57 (m, 2H), 2.78-2.88 (m, 2H), 3.30 (q, J = 6.8 Hz, 1H), 3.99 (d, J = 15.0 Hz, 1H), 4.06 (d, J = 15.0 Hz, 1H), 4.87 (m, 1H), 5.45 (brs, 1H), 6.90-7.06 (m, 5H), 7.12 (brs, 1H), 7.27 (d, J = 2.2 Hz, 1H), 7.66 (d, J = 8.8 Hz, 1H). |

TABLE 3

| Example | structural formula | $^1$H-NMR(CDCl$_3$) δ |
|---|---|---|
| 18 | (benzimidazole with 4-fluorophenoxy at 6-position, N-cyclobutyl, 2-CH2-NH-CH2-C(=O)NH2) | 1.86-2.06 (m, 2H), 2.30-2.58 (m, 2H), 2.75-2.90 (m, 2H), 3.43 (s, 2H), 4.05 (s, 2H), 4.87 (m, 1H), 5.59 (brs, 1H), 6.90-7.10 (m, 6H), 7.27 (m, 1H), 7.65 (d, J = 8.8 Hz, 1H). |

TABLE 3-continued

| Example | structural formula | ¹H-NMR(CDCl₃) δ |
|---|---|---|
| 19 | | 1.56 (m, 1H), 1.80-2.06 (m, 6H), 2.29 (m, 1H), 2.58 (q, J = 8.5 Hz, 1H), 3.18 (m, 1H), 3.32 (dd, J = 9.8, 5.4 Hz, 1H), 3.67-3.82 (m, 2H), 3.95 (d, J = 14.4 Hz, 1H), 4.11-4.34 (m, 4H), 5.28 (brs, 1H), 6.96-7.10 (m, 5H), 7.29-7.35 (m, 2H), 7.67 (brs, 1H), 7.68 (d, J = 8.5 Hz, 1H). |
| 20 | | 1.41 (d, J = 7.1 Hz, 3H), 1.55 (m, 1H), 1.80-1.93 (m, 2H), 2.10 (m, 1H), 3.35 (q, J = 7.1 Hz, 1H), 3.67-3.83 (m, 2H), 4.00-4.30 (m, 5H), 5.41 (brs, 1H), 6.85-7.10 (m, 5H), 7.25-7.35 (m, 3H), 7.67 (d, J = 8.5 Hz, 1H). |
| 21 | | 1.55 (m, 1H), 1.80-2.08 (m, 6H), 2.28 (m, 1H), 2.61 (q, J = 8.6 Hz, 1H), 3.22 (m, 1H), 3.33 (dd, J = 9.7, 5.4 Hz, 1H), 3.67-3.81 (m, 2H), 3.98 (d, J = 14.6 Hz, 1H), 4.15-4.24 (m, 4H), 5.33 (brs, 1H), 6.96-7.10 (m, 5H), 7.29-7.35 (m, 2H), 7.55 (brs, 1H), 7.68 (d, J = 8.5 Hz, 1H). |
| 22 | | 1.41 (d, J = 6.8 Hz, 3H), 1.56 (m, 1H), 1.85-1.95 (m, 2H), 2.05 (m, 1H), 3.32 (q, J = 6.8 Hz, 1H), 3.67-3.84 (m, 2H), 4.03-4.22 (m, 5H), 5.36 (brs, 1H), 6.80-7.10 (m, 5H), 7.24-7.34 (m, 3H), 7.67 (d, J = 8.5 Hz, 1H). |
| 23 | | 2.02 (m, 2H), 3.27-3.34 (m, 5H), 3.45 (s, 2H), 4.07 (s, 2H), 4.21 (t, J = 6.8 Hz, 2H), 5.78 (brs, 1H), 6.98-7.10 (m, 5H), 7.21 (brs, 1H), 7.30-7.35 (m, 2H), 7.67 (m, 1H). |

TABLE 4

| Example | structural formula | $^1$H-NMR(CDCl$_3$) δ |
|---|---|---|
| 24 | | 1.42 (d, J = 6.8 Hz, 3H), 2.00-2.26 (m, 2H), 3.28 (s, 3H), 3.28-3.36 (m, 3H), 4.01 (d, J = 14.5 Hz, 1H), 4.07 (d, J = 14.5 Hz, 1H), 4.28 (t, J = 6.8 Hz, 2H), 5.47 (brs, 1H), 6.97-7.10 (m, 5H), 7.23 (brs, 1H), 7.29-7.34 (m, 2H), 7.67 (m, 1H). |
| 25 | | 1.74-2.38 (m, 8H), 3.44 (s, 2H), 4.09 (s, 2H), 4.78 (m, 1H), 5.93 (brs, 1H), 6.93-7.68 (m, 9H). |
| 26 | | 1.40-1.42 (m, 3H), 1.74-2.21 (m, 8H), 3.30 (q, J = 6.8 Hz, 1H), 4.00-4.11 (m, 2H), 4.72-4.77 (m, 1H), 5.76 (brs, 1H), 6.94-7.68 (m, 9H). |
| 27 | | 1.09 (t, J = 7.0 Hz, 3H), 1.41 (d, J = 7.0 Hz, 3H), 3.34 (q, J = 7.0 Hz, 1H), 3.38 (q, J = 7.0 Hz, 2H), 3.68 (t, J = 5.1 Hz, 2H), 4.04 (d, J = 14.8 Hz, 1H), 4.12 (d, J = 14.8 Hz, 1H), 4.19-4.26 (m, 2H), 5.40 (brs, 1H), 6.90-7.00 (m, 4H), 7.23 (brs, 1H), 7.24-7.30 (m, 2H), 7.69 (m, 1H). |
| 28 | | 1.09 (t, J = 7.0 Hz, 3H), 3.39 (q, J = 7.0 Hz, 1H), 3.42 (s, 2H), 3.69 (t, J = 5.0 Hz, 2H), 4.10 (s, 2H), 4.27 (t, J = 5.0 Hz, 2H), 6.90-7.00 (m, 4H), 7.18 (brs, 1H), 7.24-7.30 (m, 3H), 7.68 (m, 1H). |

TABLE 4-continued

| Example | structural formula | $^1$H-NMR(CDCl$_3$) δ |
|---|---|---|
| 29 | (structure) | 1.08 (t, J = 7.0 Hz, 3H), 1.41 (d, J = 6.8 Hz, 3H), 3.30-3.42 (m, 3H), 3.68-3.70 (m, 2H), 4.04 (d, J = 14.8 Hz, 1H), 4.13 (d, J = 14.8 Hz, 1H), 4.21-4.32 (m, 2H), 5.73 (brs, 1H), 6.86-7.05 (m, 5H), 7.20-7.27 (m, 2H), 7.71 (m, 1H). |

TABLE 5

| Example | structural formula | $^1$H-NMR(CDCl$_3$) δ |
|---|---|---|
| 30 | (structure) | 1.09 (t, J = 7.0 Hz, 3H), 1.47 (s, 6H), 3.39 (q, J = 7.0 Hz, 2H), 3.70 (t, J = 5.0 Hz, 2H), 4.04 (s, 2H), 4.27 (t, J = 5.0 Hz, 2H), 5.49 (brs, 1H), 6.85-7.06 (m, 5H), 7.23 (t, J = 8.1 Hz, 1H), 7.48 (brs, 1H), 7.71 (d, J = 8.4 Hz, 1H). |
| 31 | (structure) | 1.10 (t, J = 7.0 Hz, 3H), 1.41 (d, J = 7.0 Hz, 3H), 3.33 (q, J = 7.0 Hz, 1H), 3.38 (q, J = 7.0 Hz, 2H), 3.68 (t, J = 5.0 Hz, 2H), 4.03 (d, J = 14.8 Hz, 1H), 4.12 (d, J = 14.8 Hz, 1H), 4.22 (dt, J = 15.1, 5.0 Hz, 1H), 4.28 (dt, J = 15.1, 5.0 Hz, 1H), 5.63 (brs, 1H), 6.89-7.19 (m, 5H), 7.26 (brs, 1H), 7.47 (dd, J = 7.9, 1.6 Hz, 1H), 7.68 (dd, J = 8.4, 0.7 Hz, 1H). |
| 32 | (structure) | 1.09 (t, J = 7.0 Hz, 3H), 1.46 (s, 6H), 3.38 (q, J = 7.0 Hz, 2H), 3.69 (t, J = 5.1 Hz, 2H), 4.03 (s, 2H), 4.25 (t, J = 5.1 Hz, 2H), 5.55 (brs, 1H), 6.89-7.18 (m, 5H), 7.45-7.48 (m, 2H), 7.68 (d, J = 8.4 Hz, 1H). |

TABLE 5-continued

| Example | structural formula | $^1$H-NMR(CDCl$_3$) δ |
|---|---|---|
| 33 | (structure) | 1.47 (s, 6H), 1.86-2.04 (m, 2H), 2.45-2.57 (m, 2H), 2.77-2.92 (m, 2H), 3.96 (s, 2H), 4.85 (m, 1H), 5.46 (brs, 1H), 6.94-7.11 (m, 4H), 7.29-7.37 (m, 4H), 7.67 (d, J = 8.8 Hz, 1H). |
| 34 | (structure) | 1.42 (d, J = 7.0 Hz, 3H), 1.82-2.04 (m, 2H), 2.44-2.58 (m, 2H), 2.76-2.91 (m, 2H), 3.30 (q, J = 7.0 Hz, 1H), 3.99 (d, J = 14.1 Hz, 1H), 4.06 (d, J = 14.1 Hz, 1H), 4.87 (m, 1H), 5.52 (brs, 1H), 6.94-7.11 (m, 4H), 7.13 (brs, 1H), 7.30-7.37 (m, 3H), 7.66 (d, J = 8.8 Hz, 1H). |
| 35 | (structure) | 1.46 (s, 6H), 1.57 (m, 1H), 1.82-2.10 (m, 3H), 3.67-3.84 (m, 2H), 3.96-4.25 (m, 5H), 5.36 (brs, 1H), 6.96-7.11 (m, 5H), 7.28-7.35 (m, 2H), 7.48 (brs, 1H), 7.68 (d, J = 8.6 Hz, 1H). |

TABLE 6

| Example | structural formula | $^1$H-NMR(CDCl$_3$) δ |
|---|---|---|
| 36 | (structure) | 1.08 (t, J = 7.0 Hz, 3H), 1.40 (d, J = 7.0 Hz, 3H), 3.33 (q, J = 7.0 Hz, 1H), 3.38 (q, J = 7.0 Hz, 2H), 3.68 (t, J = 5.0 Hz, 2H), 4.03 (d, J = 14.7 Hz, 1H), 4.12 (d, J = 14.7 Hz, 1H), 4.17-4.32 (m, 2H), 5.95 (brs, 1H), 6.98-7.10 (m, 5H), 7.29-7.35 (m, 3H), 7.68 (m, 1H). |
| 37 | (structure) | 1.01 (t, J = 7.3 Hz, 3H), 1.08 (t, J = 7.0 Hz, 3H), 1.70-1.84 (m, 2H), 3.15 (t, J = 6.3 Hz, 1H), 3.37 (q, J = 7.3 Hz, 2H), 3.68 (t, J = 5.2 Hz, 2H), 4.01 (d, J = 14.6 Hz, 1H), 4.13 (d, J = 14.6 Hz, 1H), 4.21 (dt, J = 15.2, 5.2 Hz, 1H), 4.30 (dt, J = 15.2, 5.2 Hz, 1H), 5.56 (brs, 1H), 6.98-7.11 (m, 5H), 7.18 (brs, 1H), 7.27-7.35 (m, 2H), 7.68 (m, 1H). |

TABLE 6-continued

| Example | structural formula | ¹H-NMR(CDCl₃) δ |
|---|---|---|
| 38 | | 0.99 (d, J = 6.9 Hz, 3H), 1.02 (d, J = 6.9 Hz, 3H), 1.08 (t, J = 7.0 Hz, 3H), 2.08 (m, 1H), 2.97 (d, J = 5.3 Hz, 1H), 3.37 (q, J = 7.0 Hz, 2H), 3.68 (t, J = 5.2 Hz, 2H), 3.99 (d, J = 14.4 Hz, 1H), 4.14 (d, J = 14.4 Hz, 1H), 4.22 (dt, J = 15.2, 5.2 Hz, 1H), 4.35 (dt, J = 15.2, 5.2 Hz, 1H), 5.80 (brs, 1H), 6.97-7.11 (m, 6H), 7.27-7.35 (m, 2H), 7.68 (m, 1H). |
| 39 | | 1.09 (t, J = 7.0 Hz, 3H), 1.46 (s, 6H), 3.39 (q, J = 7.0 Hz, 2H), 3.68 (t, J = 5.0 Hz, 2H), 4.03 (s, 2H), 4.24 (t, J = 5.0 Hz, 2H), 5.76 (brs, 1H), 6.97-7.10 (m, 5H), 7.27-7.35 (m, 2H), 7.51 (brs, 1H), 7.69 (m, 1H). |
| 40 | | 1.08 (t, J = 7.0 Hz, 3H), 2.43 (s, 3H), 3.20 (s, 2H), 3.38 (q, J = 7.0 Hz, 2H), 3.71 (t, J = 5.2 Hz, 2H), 3.96 (s, 2H), 4.37 (t, J = 5.2 Hz, 2H), 5.84 (brs, 1H), 6.98-7.11 (m, 5H), 7.27-7.35 (m, 2H), 7.38 (brs, 1H), 7.69 (m, 1H). |
| 41 | | 1.01 (t, J = 7.4 Hz, 3H), 1.08 (t, J = 7.0 Hz, 3H), 1.69-1.86 (m, 2H), 3.15 (t, J = 6.3 Hz, 1H), 3.37 (q, J = 7.0 Hz, 2H), 3.68 (t, J = 5.0 Hz, 2H), 4.00 (d, J = 14.6 Hz, 1H), 4.12 (d, J = 14.6 Hz, 1H), 4.19-4.33 (m, 2H), 5.79 (brs, 1H), 6.94-7.05 (m, 6H), 7.18 (brs, 1H), 7.67 (m, 1H). |

TABLE 7

| Example | structural formula | ¹H-NMR(CDCl₃) δ |
|---|---|---|
| 42 | | 1.08 (t, J = 7.0 Hz, 3H), 1.41 (d, J = 6.9 Hz, 3H), 2.33 (s, 3H), 3.33 (q, J = 6.9 Hz, 1H), 3.37 (q, J = 7.0 Hz, 2H), 3.67 (t, J = 5.1 Hz, 2H), 4.03 (d, J = 14.7 Hz, 1H), 4.11 (d, J = 14.7 Hz, 1H), 4.18-4.32 (m, 2H), 5.62 (brs, 1H), 6.87-7.00 (m, 4H), 7.09-7.16 (m, 2H), 7.26 (brs, 1H), 7.65 (d, J = 9.4 Hz, 1H). |
| 43 | | 1.08 (t, J = 7.0 Hz, 3H), 1.41 (d, J = 6.9 Hz, 3H), 3.34 (q, J = 6.9 Hz, 1H), 3.38 (q, J = 7.0 Hz, 2H), 3.69 (t, J = 5.0 Hz, 2H), 4.04 (d, J = 14.7 Hz, 1H), 4.13 (d, J = 14.7 Hz, 1H), 4.19-4.36 (m, 2H), 5.75 (brs, 1H), 6.94-7.04 (m, 4H), 7.13-7.20 (m, 2H), 7.25 (brs, 1H), 7.69 (d, J = 8.6 Hz, 1H). |
| 44 | | 1.09 (t, J = 7.0 Hz, 3H), 1.41 (d, J = 7.0 Hz, 3H), 2.27 (brs, 1H), 3.34 (q, J = 7.0 Hz, 1H), 3.39 (q, J = 7.0 Hz, 2H), 3.70 (t, J = 5.0 Hz, 2H), 4.05 (d, J = 14.8 Hz, 1H), 4.14 (d, J = 14.8 Hz, 1H), 4.23-4.35 (m, 2H), 5.80 (brs, 1H), 6.51-6.64 (m, 2H), 6.92-7.08 (m, 2H), 7.21 (brs, 1H), 7.72 (d, J = 8.6 Hz, 1H). |
| 45 | | 1.08 (t, J = 7.0 Hz, 3H), 1.42 (d, J = 6.9 Hz, 3H), 1.94 (brs, 1H), 3.34 (q, J = 6.9 Hz, 1H), 3.39 (q, J = 7.0 Hz, 2H), 3.70 (t, J = 5.0 Hz, 2H), 4.05 (d, J = 14.8 Hz, 1H), 4.14 (d, J = 14.8 Hz, 1H), 4.20-4.37 (m, 2H), 5.63 (brs, 1H), 6.95-7.03 (m, 3H), 7.08 (d, J = 1.8 Hz, 1H), 7.19 (brs, 1H), 7.55-7.63 (m, 2H), 7.74 (d, J = 8.8 Hz, 1H). |
| 46 | | 1.08 (t, J = 7.0 Hz, 3H), 1.42 (d, J = 7.0 Hz, 3H), 2.32 (brs, 1H), 3.34 (q, J = 7.0 Hz, 1H), 3.39 (q, J = 7.0 Hz, 2H), 3.70 (t, J = 5.1 Hz, 2H), 4.05 (d, J = 14.7 Hz, 1H), 4.14 (d, J = 14.7 Hz, 1H), 4.20-4.37 (m, 2H), 5.64 (brs, 1H), 6.97-7.08 (m, 4H), 7.22 (brs, 1H), 7.56 (brd, J = 8.4 Hz, 2H), 7.72 (d, J = 8.6 Hz, 1H). |

TABLE 7-continued

| Example | structural formula | ¹H-NMR(CDCl₃) δ |
|---|---|---|
| 47 | (structure) | 1.14 (t, J = 7.0 Hz, 3H), 1.39 (d, J = 7.0 Hz, 3H), 1.99 (m, 2H), 3.28-3.41 (m, 5H), 3.99 (d, J = 14.6 Hz, 1H), 4.05 (d, J = 14.6 Hz, 1H), 4.18 (t, J = 7.0 Hz, 2H), 5.41 (brs, 1H), 6.71-7.02 (m, 6H), 7.16 (brs, 1H), 7.63 (d, J = 8.6 Hz, 1H). |

TABLE 8

| Example | structural formula | ¹H-NMR(CDCl₃) δ |
|---|---|---|
| 48 | (structure) | 1.09 (t, J = 7.0 Hz, 3H), 1.41 (d, J = 7.0 Hz, 3H), 3.33 (q, J = 7.0 Hz, 1H), 3.39 (q, J = 7.0 Hz, 2H), 3.69 (t, J = 5.1 Hz, 2H), 4.04 (d, J = 14.8 Hz, 1H), 4.12 (d, J = 14.8 Hz, 1H), 4.20-4.33 (m, 2H), 5.43 (br, 1H), 6.71 (m, 1H), 6.80 (m, 1H), 6.95-7.00 (m, 2H), 7.10 (q, J = 9.0 Hz, 1H), 7.22 (br, 1H), 7.69 (d, J = 8.3 Hz, 1H). |
| 49 | (structure) | 1.08 (t, J = 7.0 Hz, 3H), 1.41 (d, J = 7.0 Hz, 3H), 3.33 (q, J = 7.0 Hz, 1H), 3.38 (q, J = 7.0 Hz, 2H), 3.68 (t, J = 5.0 Hz, 2H), 4.03 (d, J = 14.8 Hz, 1H), 4.11 (d, J = 14.8 Hz, 1H), 4.18-4.32 (m, 2H), 5.41 (br, 1H), 6.83 (m, 1H), 6.91-7.05 (m, 4H), 7.22 (br, 1H), 7.65 (m, 1H). |
| 50 | (structure) | 1.21 (s, 3H), 1.29 (s, 3H), 1.33 (d, J = 6.9 Hz, 3H), 3.35 (q, J = 6.9 Hz, 1H), 4.04 (d, J = 13.9 Hz, 1H), 4.10 (s, 2H), 4.11 (d, J = 13.9 Hz, 1H), 5.87 (brs, 1H), 6.91-7.05 (m, 6H), 7.09 (brs, 1H), 7.63 (d, J = 9.3 Hz, 1H). |
| 51 | (structure) | 1.40 (d, J = 7.0 Hz, 3H), 1.55 (m, 1H), 1.77-1.94 (m, 2H), 1.97-2.12 (m, 2H), 3.34 (q, J = 7.0 Hz, 1H), 3.65-3.83 (m, 2H), 3.96-4.27 (m, 5H), 5.67 (brs, 1H), 6.91-7.06 (m, 6H), 7.24 (brs, 1H), 7.66 (dd, J = 8.4, 0.6 Hz, 1H). |

TABLE 8-continued

| Example | structural formula | ¹H-NMR(CDCl₃) δ |
|---|---|---|
| 52 | | 1.07 (t, J = 7.0 Hz, 3H), 1.41 (d, J = 7.0 Hz, 3H), 3.33 (q, J = 7.0 Hz, 1H), 3.38 (q, J = 7.0 Hz, 2H), 3.68 (t, J = 5.1 Hz, 2H), 4.03 (d, J = 14.7 Hz, 1H), 4.12 (d, J = 14.7 Hz, 1H), 4.18-4.32 (m, 2H), 5.43 (br, 1H), 6.95-7.23 (m, 6H), 7.25 (br, 1H), 7.66 (m, 1H). |
| 53 | | 1.09 (t, J = 7.0 Hz, 3H), 1.42 (d, J = 7.0 Hz, 3H), 3.34 (q, J = 7.0 Hz, 1H), 3.39 (q, J = 7.0 Hz, 2H), 3.69 (t, J = 5.0 Hz, 2H), 4.05 (d, J = 14.8 Hz, 1H), 4.13 (d, J = 14.8 Hz, 1H), 4.19-4.35 (m, 2H), 5.44 (br, 1H), 6.64-6.81 (m, 3H), 6.98-7.06 (m, 2H), 7.20-7.30 (m, 2H), 7.71 (d, J = 8.4 Hz, 1H). |

TABLE 9

| Example | structural formula | ¹H-NMR(CDCl₃) δ |
|---|---|---|
| 54 | | 1.09 (t, J = 7.0 Hz, 3H), 1.41 (d, J = 6.8 Hz, 3H), 3.33 (q, J = 6.8 Hz, 1H), 3.38 (q, J = 7.0 Hz, 2H), 3.68 (t, J = 5.2 Hz, 2H), 4.03 (d, J = 14.7 Hz, 1H), 4.12 (d, J = 14.7 Hz, 1H), 4.16-4.32 (m, 2H), 5.41 (brs, 1H), 6.93-7.05 (m, 6H), 7.23 (brs, 1H), 7.67 (m, 1H). |
| 55 | | 1.09 (t, J = 7.0 Hz, 3H), 1.41 (d, J = 7.0 Hz, 3H), 3.33 (q, J = 7.0 Hz, 1H), 3.39 (q, J = 7.0 Hz, 2H), 3.69 (t, J = 5.0 Hz, 2H), 4.04 (d, J = 14.8 Hz, 1H), 4.12 (d, J = 14.8 Hz, 1H), 4.19-4.34 (m, 2H), 5.35 (br, 1H), 6.79-7.13 (m, 4H), 7.20 (br, 1H), 7.69 (d, J = 8.6 Hz, 1H). |

TABLE 9-continued

| Example | structural formula | $^1$H-NMR(CDCl$_3$) δ |
|---|---|---|
| 56 | | 1.41 (d, J = 6.8 Hz, 3H), 1.50-2.10 (m, 4H), 3.32 (q, J = 6.8 Hz, 1H), 3.66-3.84 (m, 2H), 4.01-4.23 (m, 5H), 5.44 (br, 1H), 6.93-7.05 (m, 6H), 7.25 (m, 1H), 7.66 (d, J = 6.4 Hz, 1H). |
| 57 | | 1.08 (t, J = 7.0 Hz, 3H), 1.42 (d, J = 6.8 Hz, 3H), 3.34 (q, J = 6.8 Hz, 1H), 3.39 (q, J = 7.0 Hz, 2H), 3.70 (t, J = 5.1 Hz, 2H), 4.05 (d, J = 14.8 Hz, 1H), 4.13 (d, J = 14.8 Hz, 1H), 4.20-4.35 (m, 2H), 5.47 (br, 1H), 6.39 (m, 1H), 6.65 (m, 1H), 7.01 (dd, J = 8.8, 2.4 Hz, 1H), 7.08 (d, J = 2.4 Hz, 1H), 7.20 (br, 1H), 7.72 (d, J = 8.8 Hz, 1H). |
| 58 | | 1.08 (t, J = 7.0 Hz, 3H), 1.41 (d, J = 6.8 Hz, 3H), 3.33 (q, J = 6.8 Hz, 1H), 3.38 (q, J = 7.0 Hz, 2H), 3.69 (t, J = 5.0 Hz, 2H), 4.03 (d, J = 14.8 Hz, 1H), 4.12 (d, J = 14.8 Hz, 1H), 4.19-4.34 (m, 2H), 5.52 (br, 1H), 6.72 (m, 1H), 6.87-7.04 (m, 4H), 7.23 (br, 1H), 7.68 (d, J = 8.6 Hz, 1H). |

Reference Example 8

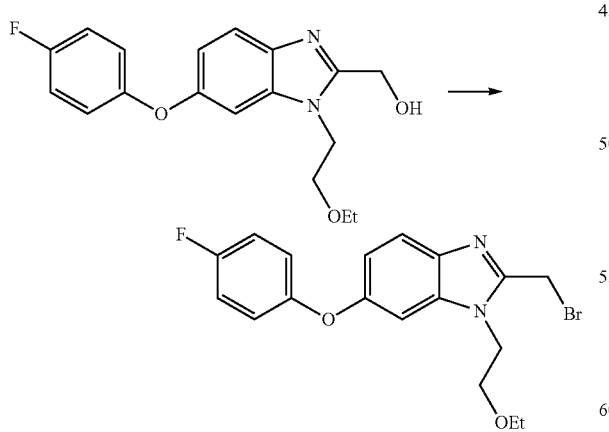

To a solution of the compound (0.22 g, 0.66 mmol) obtained in Reference Example 6 in tetrahydrofuran (3 ml) was added phosphorus tribromide (0.18 g, 0.66 mmol) under ice-cooling. After stirring for 1 hr, aqueous sodium hydrogen carbonate solution was added thereto, and the mixture was extracted with ethyl acetate, dried over magnesium sulfate, and concentrated under reduced pressure. The concentrate was directly used for the next reaction.

$^1$H-NMR (CDCl$_3$) δ 1.08 (t, J=7.0 Hz, 3H), 3.39 (q, J=7.0 Hz, 2H), 3.70 (t, J=5.1 Hz, 2H), 4.37 (t, J=5.1 Hz, 2H), 4.81 (s, 2H), 6.95-7.05 (m, 6H), 7.69 (m, 1H).

Example 59

N$^2$-{[1-(2-ethoxyethyl)-6-(4-fluorophenoxy)-1H-benzimidazol-2-yl]methyl}-L-alaninamide

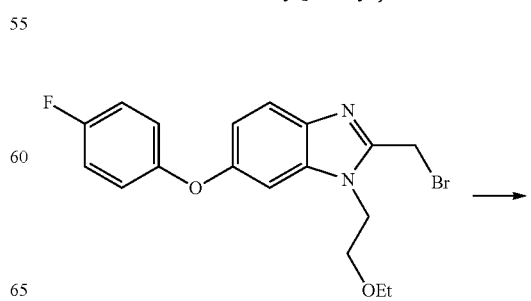

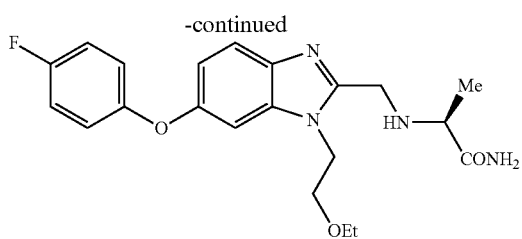

To a solution of the compound (107 mg, 0.27 mmol) obtained in Reference Example 8 in acetonitrile (3 ml) were added diisopropylethylamine (0.10 ml, 0.55 mmol) and N-(2,4-dimethoxybenzyl)alaninamide (97.7 mg, 0.41 mmol). After stirring at 50° C. for 5 hr, aqueous sodium hydrogen carbonate solution was added thereto, and the mixture was extracted with chloroform. The organic layer was dried over magnesium sulfate, and concentrated under reduced pressure. Trifluoroacetic acid (3 mL) was added thereto, and the mixture was further stirred at 50° C. for 2 hr, neutralized with aqueous sodium hydroxide solution, and extracted with ethyl acetate. The organic layer was dried over magnesium sulfate, and concentrated under reduced pressure. The obtained residue was recrystallized from chloroform/2-propanol to give the object product (75 mg, 70%).

$^1$H-NMR (CDCl$_3$) δ1.08 (t, J=7.0 Hz, 3H), 1.41 (d, J=6.8 Hz, 3H), 3.33-3.41 (m, 3H), 3.68 (t, J=5.1 Hz, 2H), 4.03 (d, J=14.6 Hz, 1H), 4.12 (d, J=14.6 Hz, 1H), 4.23-4.27 (m, 2H), 5.58 (brs, 1H), 6.94-7.05 (m, 6H), 7.24 (brs, 1H), 7.67 (m, 1H).

Examples 60-65

The compounds of Examples 60-65 shown in Table 10 were prepared in the same manner as in Reference Examples 1-4, 8 and Example 59 from 2,4-difluoronitrobenzene and using commercially available or known compounds.

TABLE 10

| Example | structural formula | $^1$H-NMR(CDCl$_3$) δ |
|---|---|---|
| 60 | (structure shown) | 1.41 (d, J = 7.0 Hz, 3H), 3.26 (s, 3H), 3.33 (q, J = 7.0 Hz, 1H), 3.65 (t, J = 4.9 Hz, 2H), 4.02 (d, J = 14.6 Hz, 1H), 4.10 (d, J = 14.6 Hz, 1H), 4.22-4.28 (m, 2H), 5.34 (brs, 1H), 6.94-7.05 (m, 6H), 7.25 (brs, 1H), 7.67 (m, 1H). |
| 61 | (structure shown) | 1.02 (d, J = 6.2 Hz, 6H), 3.40-3.48 (m, 3H), 3.68 (t, J = 5.1 Hz, 2H), 4.10 (s, 2H), 4.24 (t, J = 5.1 Hz, 2H), 5.45 (brs, 1H), 6.94-7.05 (m, 6H), 7.21 (brs, 1H), 7.67 (m, 1H). |
| 62 | (structure shown) | 1.01 (d, J = 6.0 Hz, 6H), 1.41 (d, J = 7.0 Hz, 3H), 3.33 (q, J = 7.0 Hz, 1H), 3.43 (m, 1H), 3.67 (t, J = 5.1 Hz, 2H), 4.04 (d, J = 14.8 Hz, 1H), 4.12 (d, J = 14.8 Hz, 1H), 4.22 (m, 2H), 5.33 (brs, 1H), 6.93-7.05 (m, 6H), 7.26 (brs, 1H), 7.67 (m, 1H). |
| 63 | (structure shown) | 3.25 (s, 3H), 3.40 (s, 2H), 3.64 (t, J = 5.0 Hz, 2H), 4.08 (s, 2H), 4.26 (t, J = 5.0 Hz, 2H), 6.34 (brs, 1H), 6.93-7.04 (m, 6H), 7.21 (brs, 1H), 7.65 (m, 1H). |

TABLE 10-continued

| Example | structural formula | ¹H-NMR(CDCl₃) δ |
|---|---|---|
| 64 | | 1.42 (d, J = 7.0 Hz, 3H), 2.02 (quint, J = 6.7 Hz, 2H), 3.28 (s, 3H), 3.27-3.37 (m, 3H), 4.01 (d, J = 14.6 Hz, 1H), 4.07 (d, J = 14.6 Hz, 1H), 4.19 (t, J = 6.7 Hz, 2H), 5.36 (brs, 1H), 6.93-7.05 (m, 6H), 7.21 (brs, 1H), 7.66 (d, J = 8.8 Hz, 1H). |
| 65 | | 1.82-1.87 (m, 2H), 2.43-2.57 (m, 2H), 3.43 (s, 2H), 3.51-3.59 (m, 2H), 4.11 (s, 2H), 4.14-4.19 (m, 2H), 4.49 (m, 1H), 5.46 (brs, 1H), 6.80 (brs, 1H), 6.91-7.05 (m, 5H), 7.25(d, J = 2.0 Hz, 1H), 7.67 (d, J = 8.8 Hz, 1H). |

Reference Example 9

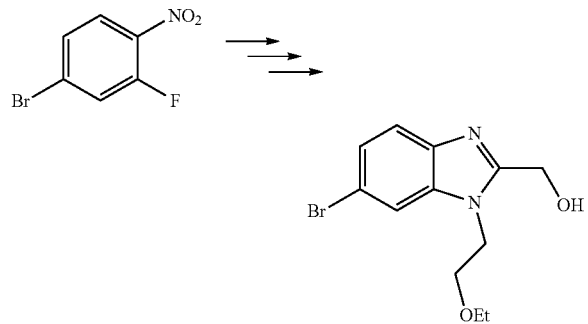

The object product was obtained in the same manner as in Reference Examples 1, 3 and 4 from 2-fluoro-4-bromonitrobenzene.

¹H-NMR (CDCl₃) δ 1.12 (t, J=7.0 Hz, 3H), 3.43 (q, J=7.0 Hz, 2H), 3.75 (t, J=5.1 Hz, 2H), 4.37 (t, J=5.1 Hz, 2H), 4.88 (s, 2H), 7.36 (dd, J=8.6, 1.8 Hz, 1H), 7.49 (d, J=1.8 Hz, 1H), 7.59 (d, J=8.6 Hz, 1H).

Reference Example 10

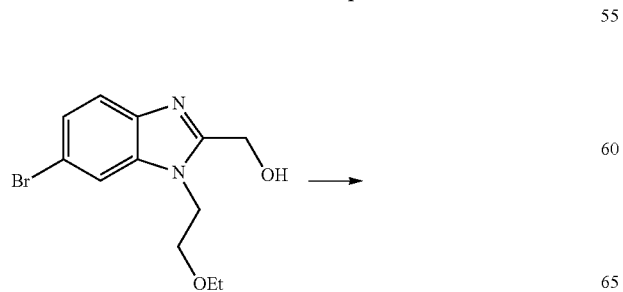

The object product was obtained in the same manner as in Reference Example 5 from the compound obtained in Reference Example 9.

¹H-NMR (CDCl₃) δ 1.02 (t, J=7.0 Hz, 3H), 3.35 (q, J=7.0 Hz, 2H), 3.71 (t, J=5.1 Hz, 2H), 4.64 (t, J=5.1 Hz, 2H), 7.41 (m, 1H), 7.68-7.73 (m, 2H), 10.05 (s, 1H).

Reference Example 11

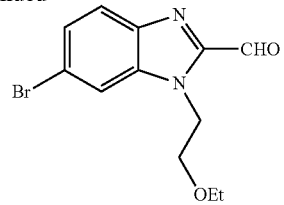

To a solution (4:1, 15 mL) of the compound (200 mg, 0.67 mmol) obtained in Reference Example 10 in a mixed solvent of dioxane-water were added potassium carbonate (280 mg, 2.02 mmol), phenylboronic acid (123 mg, 1.01 mmol) and tetrakis(triphenylphosphine)palladium (154 mg, 0.13 mmol), and the mixture was heated to 110° C. After refluxing for 2 hr, water was added thereto, and the mixture was extracted with ethyl acetate. The organic layer was washed with saturated brine, dried over magnesium sulfate, and concentrated under reduced pressure. The obtained residue was purified by silica gel column (hexane:ethyl acetate=90:10-75:25-50:50) to give the object product (115 mg, 58%).

$^1$H-NMR (CDCl$_3$) δ 1.07 (t, J=7.0 Hz, 3H), 3.42 (q, J=7.0 Hz, 2H), 3.81 (t, J=5.1 Hz, 2H), 4.81 (t, J=5.1 Hz, 2H), 7.39 (m, 1H), 7.48 (t, J=7.6 Hz, 2H), 7.63-7.67 (m, 3H), 7.76 (m, 1H), 7.96 (d, J=8.6 Hz, 1H), 10.11 (s, 1H).

Example 66

N$^2$-{[1-(2-ethoxyethyl)-6-phenyl-1H-benzimidazol-2-yl]methyl}glycinamide

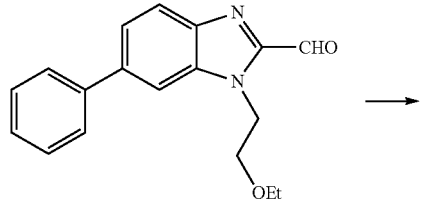 

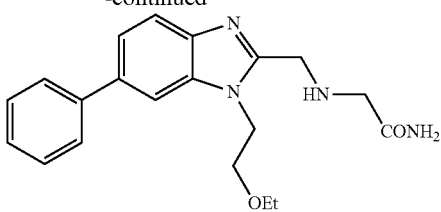

The object product (31 mg, 38%) was obtained in the same manner as in Example 2 from the compound obtained in Reference Example 11 (68 mg, 0.23 mmol).

$^1$H-NMR (CDCl$_3$) δ1.08 (t, J=7.1 Hz, 3H), 3.38 (q, J=7.1 Hz, 2H), 3.41 (s, 2H), 3.75 (t, J=5.1 Hz, 2H), 4.11 (s, 2H), 4.35 (t, J=5.1 Hz, 2H), 5.68 (brs, 1H), 7.22 (brs, 1H), 7.33 (m, 1H), 7.42-7.51 (m, 4H), 7.61-7.63 (m, 2H), 7.76 (m, 1H).

Examples 67-73

The compounds of Examples 67-73 shown in Table 11 and Table 12 were prepared in the same manner as in Reference Examples 9-11 and Example 66.

TABLE 11

| Example | structural formula | $^1$H-NMR (CDCl$_3$) δ |
|---|---|---|
| 67 | (4-F-phenyl)-benzimidazole-CH$_2$-NH-CH$_2$-CONH$_2$, N-CH$_2$CH$_2$OCH$_2$CH$_3$ | 1.03 (t, J = 7.1 Hz, 3H), 3.29 (q, J = 7.1 Hz, 2H), 3.36 (s, 2H), 3.70 (t, J = 5.1 Hz, 2H), 4.06 (s, 2H), 4.30 (t, J = 5.1 Hz, 2H), 5.68 (brs, 1H), 7.05-7.09 (m, 2H), 7.16 (brs, 1H), 7.37-7.39 (m, 2H), 7.49-7.53 (m, 2H), 7.70 (m, 1H). |
| 68 | (4-F-phenyl)-benzimidazole-CH$_2$-NH-CH(CH$_3$)-CONH$_2$, N-CH$_2$CH$_2$OCH$_2$CH$_3$ | 1.08 (t, J = 7.1 Hz, 3H), 1.39 (d, J = 6.8 Hz, 3H), 3.32 (q, J = 6.8 Hz, 1H), 3.37 (q, J = 7.1 Hz, 2H), 3.73 (t, J = 5.0 Hz, 2H), 4.04 (d, J = 14.8 Hz, 1H), 4.13 (d, J = 14.8 Hz, 1H), 4.31 (dt, J = 15.9, 5.0 Hz, 1H), 4.36 (dt, J = 15.9, 5.0 Hz, 1H), 5.61 (brs, 1H), 7.10-7.14 (m, 2H), 7.25 (brs, 1H), 7.41-7.43 (m, 2H), 7.54-7.57 (m, 2H), 7.74 (m, 1H). |
| 69 | phenyl-benzimidazole-CH$_2$-NH-CH(CH$_3$)-CONH$_2$, N-CH$_2$CH$_2$OCH$_2$CH$_3$ | 1.08 (t, J = 7.0 Hz, 3H), 1.39 (d, J = 6.9 Hz, 3H), 3.30 (q, J = 6.9 Hz, 1H), 3.37 (q, J = 7.0 Hz, 2H), 3.73 (t, J = 4.8 Hz, 2H), 4.04 (d, J = 14.8 Hz, 1H), 4.13 (d, J = 14.8 Hz, 1H), 4.28-4.38 (m, 2H), 5.73 (brs, 1H), 7.28 (brs, 1H), 7.33 (m, 1H), 7.41-7.50 (m, 4H), 7.60-7.63 (m, 2H), 7.75 (m, 1H). |

TABLE 11-continued

| Example | structural formula | ¹H-NMR (CDCl₃) δ |
|---|---|---|
| 70 | | 1.10 (t, J = 7.0 Hz, 3H), 3.40 (q, J = 7.0 Hz, 2H), 3.44 (s, 2H), 3.75 (t, J = 5.0 Hz, 2H), 4.14 (s, 2H), 4.36 (t, J = 5.0 Hz, 2H), 5.60 (brs, 1H), 7.27-7.36 (m, 4H), 7.40-7.43 (m, 2H), 7.50 (m, 1H), 7.78 (m, 1H). |

TABLE 12

| Example | structural formula | ¹H-NMR(CDCl₃) δ |
|---|---|---|
| 71 | | 1.10 (t, J = 7.0 Hz, 3H), 1.42 (d, J = 7.0 Hz, 3H), 3.35 (q, J = 7.0 Hz, 1H), 3.39 (q, J = 7.0 Hz, 2H), 3.74 (t, J =5.0 Hz, 2H), 4.07 (d, J = 14.7 Hz, 1H), 4.16 (d, J = 14.7 Hz, 1H), 4.30 (dt, J = 15.0, 5.0 Hz, 1H), 4.37 (dt, J = 15.0, 5.0 Hz, 1H), 5.81 (brs, 1H), 7.26-7.36 (m, 4H), 7.39-7.42 (m, 2H), 7.50 (m, 1H), 7.78 (m, 1H). |
| 72 | | 1.10 (t, J = 7.0 Hz, 3H), 3.40 (q, J = 7.0 Hz, 2H), 3.43 (s, 2H), 3.77 (t, J = 5.1 Hz, 2H), 4.13 (s, 2H), 4.38 (t, J = 5.1 Hz, 2H), 5.65 (brs, 1H), 7.21 (brs, 1H), 7.41-7.49 (m, 4H), 7.54-7.58 (m, 2H), 7.78 (m, 1H). |
| 73 | | 1.10 (t, J = 7.0 Hz, 3H), 1.41 (d, J = 7.0 Hz, 3H), 3.35 (q, J = 7.0 Hz, 1H), 3.40 (q, J = 7.0 Hz, 2H), 3.76 (t, J = 5.0 Hz, 2H), 4.06 (d, J = 14.7 Hz, 1H), 4.16 (d, J = 14.7 Hz, 1H), 4.31-4.44 (m, 2H), 5.81 (brs, 1H), 7.28 (brs, 1H), 7.40-7.47 (m, 4H), 7.53-7.57 (m, 2H), 7.78 (m, 1H). |

Reference Example 12

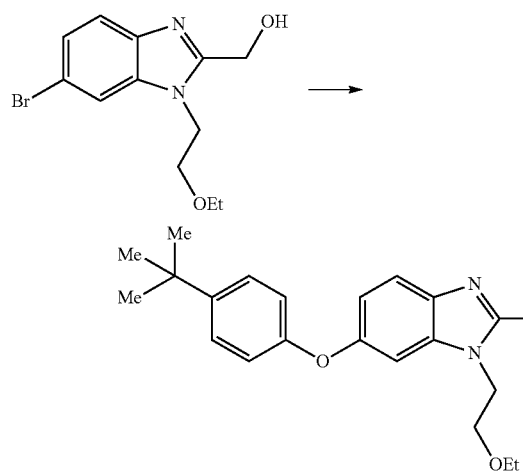

Under a nitrogen atmosphere, to a solution of the compound (150 mg, 0.5 mmol) obtained in Reference Example 9 in N-methylpyrrolidinone (5 mL) were added cesium carbonate (489 mg, 1.5 mmol), 4-tert-butylphenol (225 mg, 1.5 mmol), 2,2,6,6-tetramethylheptane-3,5-dione (52 μl, 0.25 mmol) and copper(I) chloride (50 mg, 0.5 mmol), and the mixture was heated to 120° C. After stirring for 6 hr, the reaction mixture was added to 2 mol/L hydrochloric acid under ice-cooling, and the mixture was extracted with ethyl acetate. The organic layer was washed with 0.5 mol/L hydrochloric acid, 2 mol/L aqueous sodium hydroxide solution, water and saturated brine, dried over sodium sulfate, and concentrated under reduced pressure. The obtained residue was purified by silica gel column (hexane:ethyl acetate=100:0-0:100) to give the object product (56 mg, 30%).

$^1$H-NMR (CDCl$_3$) δ 1.09 (t, J=7.0 Hz, 3H), 1.32 (s, 9H), 3.41 (q, J=7.0 Hz, 2H), 3.72 (t, J=5.1 Hz, 2H), 4.35 (t, J=5.1 Hz, 2H), 4.89 (s, 2H), 6.89-7.02 (m, 4H), 7.31-7.36 (m, 2H), 7.64 (d, J=8.5 Hz, 1H).

Example 74

N$^2$-{[6-(4-tert-butylphenoxy)-1-(2-ethoxyethyl)-1H-benzimidazol-2-yl]methyl}-L-alaninamide

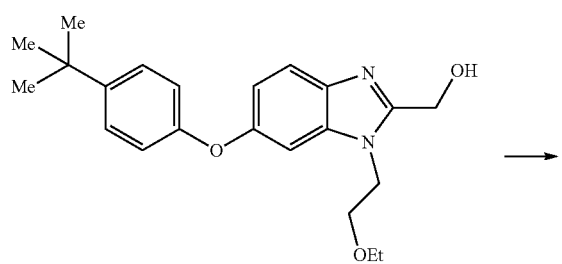

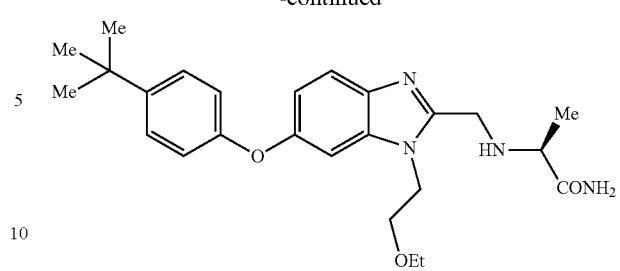

The object product was obtained in the same manner as in Reference Example 5 and Example 1 from the compound obtained in Reference Example 12.

$^1$H-NMR (CDCl$_3$) δ 1.09 (t, J=7.0 Hz, 3H), 1.32 (s, 9H), 1.41 (d, J=6.9 Hz, 3H), 3.34 (q, J=6.9 Hz, 1H), 3.38 (q, J=7.0 Hz, 2H), 3.68 (t, J=5.1 Hz, 2H), 4.04 (d, J=14.9 Hz, 1H), 4.12 (d, J=14.9 Hz, 1H), 4.18-4.34 (m, 2H), 5.47 (brs, 1H), 6.89-6.95 (m, 2H), 6.97-7.02 (m, 2H), 7.29 (brs, 1H), 7.31-7.36 (m, 2H), 7.67 (d, J=8.5 Hz, 1H).

Reference Example 13

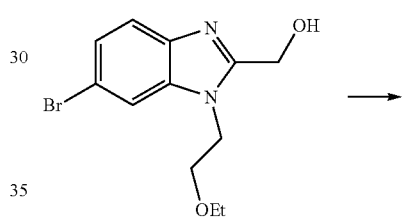

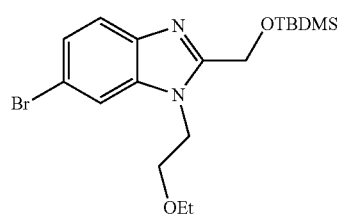

To a solution of the compound (1.20 g, 4 mmol) obtained in Reference Example 9 in N,N-dimethylformamide (15 ml) were added imidazole (1.36 g, 20 mmol) and tert-butyldimethylsilyl chloride (904 mg, 6 mmol). After stirring at room temperature for 2 hr, water was added thereto, and the mixture was extracted with ethyl acetate. The organic layer was washed with water and saturated brine, dried over sodium sulfate, and concentrated under reduced pressure. The obtained residue was purified by silica gel column (hexane:ethyl acetate=100:0-85:15) to give the object product (1.65 g, 100%).

$^1$H-NMR (CDCl$_3$) δ0.11 (s, 6H), 0.91 (s, 9H), 1.12 (t, J=7.0 Hz, 3H), 3.41 (q, J=7.0 Hz, 2H), 3.74 (t, J=5.5 Hz, 2H), 4.44 (t, J=5.5 Hz, 2H), 4.99 (s, 2H), 7.34 (dd, J=1.9, 8.5 Hz, 1H), 7.56-7.62 (m, 2H).

Reference Example 14

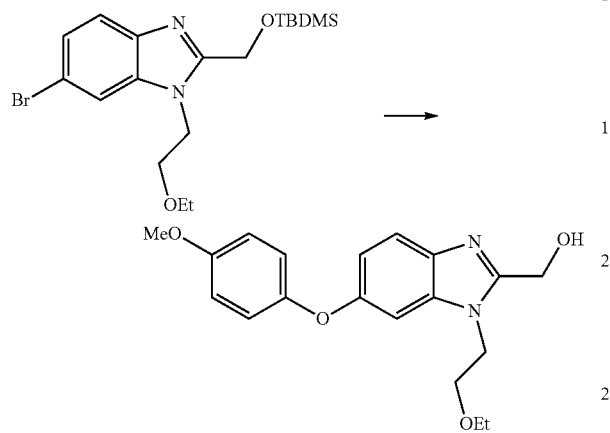

Under a nitrogen atmosphere, to a solution of the compound (207 mg, 0.5 mmol) obtained in Reference Example 13 in N-methylpyrrolidinone (5 mL) were added cesium carbonate (489 mg, 1.5 mmol), 4-methoxyphenol (186 mg, 1.5 mmol), 2,2,6,6-tetramethylheptane-3,5-dione (52 μl, 0.25 mmol) and copper(I) chloride (50 mg, 0.5 mmol), and the mixture was heated to 120° C. After stirring for 4 hr, the reaction mixture was added to 2 mol/L hydrochloric acid under ice-cooling, and the mixture was extracted with ethyl acetate. The organic layer was washed with 0.5 mol/L hydrochloric acid, 2 mol/L aqueous sodium hydroxide solution, water and saturated brine, dried over sodium sulfate, and concentrated under reduced pressure. The obtained residue was purified by silica gel column (hexane:ethyl acetate=100:0-0:100) to give the object product (36 mg, 21%).

$^1$H-NMR (CDCl$_3$) δ 1.10 (t, J=7.0 Hz, 3H), 3.41 (q, J=7.0 Hz, 2H), 3.70 (t, J=5.0 Hz, 2H), 3.81 (s, 3H), 4.32 (t, J=5.0 Hz, 2H), 4.88 (s, 2H), 6.84-7.01 (m, 6H), 7.63 (d, J=8.8 Hz, 1H).

Example 75

N$^2$-{[1-(2-ethoxyethyl)-6-(4-methoxyphenoxy)-1H-benzimidazol-2-yl]methyl}-L-alaninamide

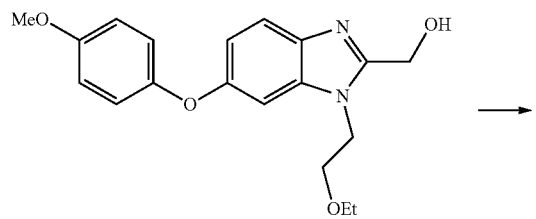

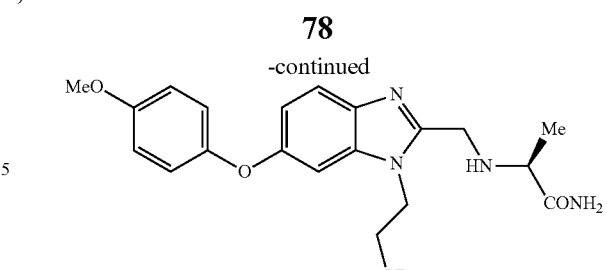

The object product was obtained in the same manner as in Reference Example 5 and Example 1 from the compound obtained in Reference Example 14.

$^1$H-NMR (CDCl$_3$) δ 1.09 (t, J=7.0 Hz, 3H), 1.41 (d, J=6.8 Hz, 3H), 3.33 (q, J=6.8 Hz, 1H), 3.37 (q, J=7.0 Hz, 2H), 3.67 (t, J=5.1 Hz, 2H), 3.81 (s, 3H), 4.03 (d, J=14.7 Hz, 1H), 4.10 (d, J=14.7 Hz, 1H), 4.17-4.30 (m, 2H), 5.32 (brs, 1H), 6.85-7.00 (m, 6H), 7.27 (brs, 1H), 7.64 (d, J=8.8 Hz, 1H).

Reference Example 15

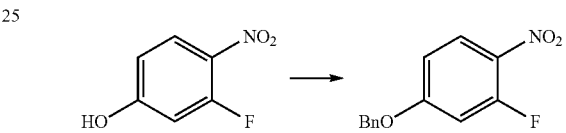

To a solution of 3-fluoro-4-nitrophenol (2.5 g, 16.0 mmol) in N,N-dimethylformamide (30 ml) were added potassium carbonate (3.3 g, 24.0 mmol) and benzyl bromide (2.1 ml, 17.6 mmol), and the mixture was heated at 70° C. After stirring for 1 hr, water was added thereto, and the mixture was extracted with ethyl acetate. The organic layer was washed with saturated brine, dried over magnesium sulfate, and concentrated under reduced pressure, and the obtained residue was directly used for the next reaction.

$^1$H-NMR (CDCl$_3$) δ5.14 (s, 2H), 6.79-6.86 (m, 2H), 7.38-7.43 (m, 5H), 8.10 (m, 1H).

Reference Example 16

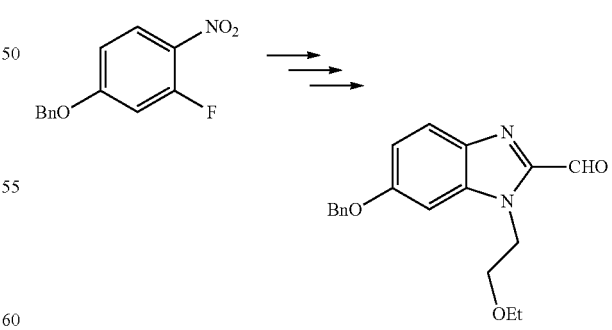

The object product was obtained in the same manner as in Reference Examples 1 and 3-5 from the compound obtained in Reference Example 15.

$^1$H-NMR (CDCl$_3$) δ 1.08 (t, J=7.0 Hz, 3H), 3.40 (q, J=7.0 Hz, 2H), 3.77 (t, J=5.1 Hz, 2H), 4.71 (t, J=5.1 Hz, 2H), 5.15

(s, 2H), 7.04 (d, J=2.4 Hz, 1H), 7.11 (dd, J=9.0, 2.4 Hz, 1H), 7.35-7.49 (m, 5H), 7.79 (d, J=9.0 Hz, 1H), 10.01 (s, 1H).

Example 76

N²-{[6-(benzyloxy)-1-(2-ethoxyethyl)-1H-benzimidazol-2-yl]methyl}-L-alaninamide

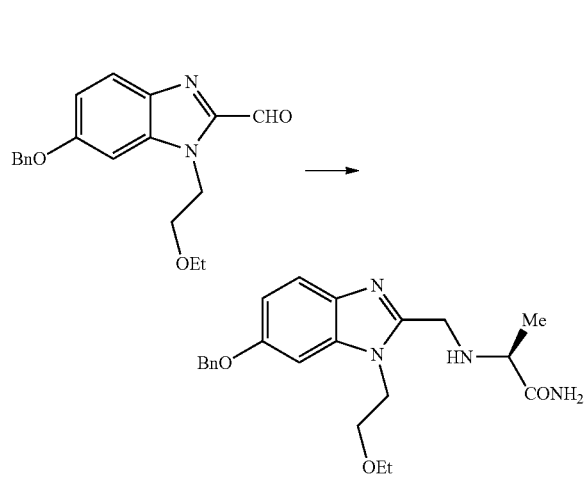

The object product was obtained in the same manner as in Example 2 from the compound obtained in Reference Example 16 and (L)-alaninamide hydrochloride.

¹H-NMR (CDCl₃) δ 1.09 (t, J=7.0 Hz, 3H), 1.39 (d, J=7.0 Hz, 3H), 3.32 (q, J=7.0 Hz, 1H), 3.37 (q, J=7.0 Hz, 2H), 3.68 (t, J=5.1 Hz, 2H), 4.00 (d, J=14.6 Hz, 1H), 4.09 (d, J=14.6 Hz, 1H), 4.16-4.32 (m, 2H), 5.11 (s, 2H), 5.75 (brs, 1H), 6.87 (d, J=2.2 Hz, 1H), 6.98 (dd, J=8.8, 2.2 Hz, 1H), 7.27-7.53 (m, 6H), 7.61 (d, J=8.8 Hz, 1H).

Example 77

N²-{[6-(benzyloxy)-1-(2-ethoxyethyl)-1H-benzimidazol-2-yl]methyl}-2-methylalaninamide

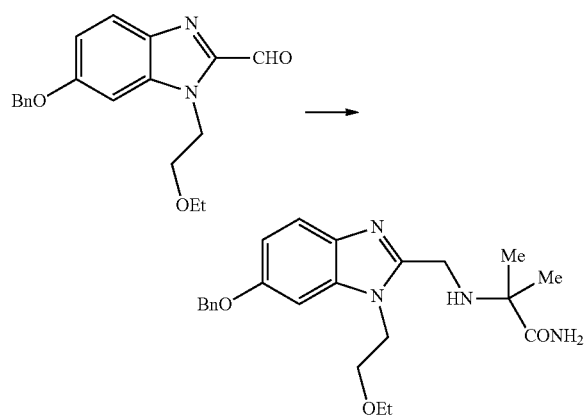

The object product was obtained in the same manner as in Example 2 from the compound obtained in Reference Example 16 and 2-methylalaninamide.

¹H-NMR (CDCl₃) δ 1.10 (t, J=7.0 Hz, 3H), 1.45 (s, 6H), 3.37 (q, J=7.0 Hz, 2H), 3.69 (t, J=5.1 Hz, 2H), 4.00 (s, 2H), 4.24 (t, J=5.1 Hz, 2H), 5.12 (s, 2H), 5.47 (brs, 1H), 6.86 (d, J=2.4 Hz, 1H), 6.98 (dd, J=8.8, 2.4 Hz, 1H), 7.31-7.48 (m, 5H), 7.51 (brs, 1H), 7.62 (d, J=8.8 Hz, 1H).

Reference Example 17

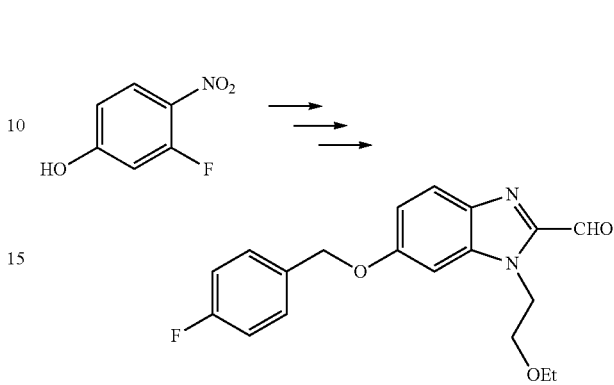

The object product was obtained in the same manner as in Reference Examples 15, 1 and 3-5 from 3-fluoro-4-nitrophenol.

¹H-NMR (CDCl₃) δ 1.07 (t, J=7.0 Hz, 3H), 3.40 (q, J=7.0 Hz, 2H), 3.78 (t, J=5.3 Hz, 2H), 4.71 (t, J=5.3 Hz, 2H), 5.10 (s, 2H), 7.03 (d, J=2.2 Hz, 1H), 7.07-7.13 (m, 3H), 7.42-7.47 (m, 2H), 7.79 (d, J=9.0 Hz, 1H), 10.01 (s, 1H).

Example 78

N²-({1-(2-ethoxyethyl)-6-[(4-fluorobenzyl)oxy]-1H-benzimidazol-2-yl}methyl)-L-alaninamide The object product was obtained in the same manner as in Example 2 from the compound obtained in Reference Example 17 and (L)-alaninamide hydrochloride.

¹H-NMR (CDCl₃) δ 1.10 (t, J=7.0 Hz, 3H), 1.40 (d, J=7.0 Hz, 3H), 3.32 (q, J=7.0 Hz, 1H), 3.38 (q, J=7.0 Hz, 2H), 3.70 (t, J=5.1 Hz, 2H), 4.01 (d, J=14.6 Hz, 1H), 4.09 (d, J=14.6 Hz, 1H), 4.20-4.32 (m, 2H), 5.08 (s, 2H), 5.39 (brs, 1H), 6.86 (d, J=2.2 Hz, 1H), 6.96 (dd, J=8.8, 2.2 Hz, 1H), 7.06-7.10 (m, 2H), 7.25 (brs, 1H), 7.42-7.45 (m, 2H), 7.62 (d, J=8.8 Hz, 1H).

Reference Example 18

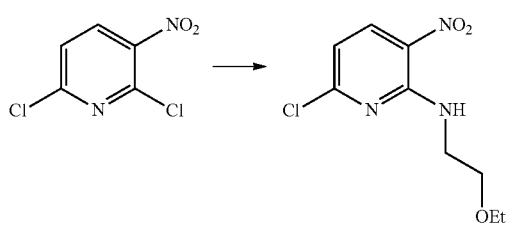 [SMILES: O=[N+]([O-])c1ccc(Cl)nc1Cl ; CCOCCNc1nc(Cl)ccc1[N+](=O)[O-]]

To a solution of 2,6-dichloro-3-nitropyridine (3.0 g, 15.5 mmol) in dioxane (50 mL) were added potassium carbonate (2.4 g, 17.0 mmol) and 2-ethoxyethylamine (1.4 g, 17.0 mmol), and the mixture was stirred at 50° C. After stirring for 3 hr, potassium carbonate (1.8 g, 13.0 mmol) and 2-ethoxyethylamine (0.9 g, 10.0 mmol) were added thereto, and the mixture was stirred at 50° C. for 3 hr. Water was added to the reaction mixture, and the mixture was extracted with ethyl acetate. The organic layer was washed with water and saturated brine, dried over sodium sulfate, and concentrated under reduced pressure. The residue was purified by silica gel column (ethyl acetate:hexane=1:5) to give the object product (3.4 g, 89%).

$^1$H-NMR (CDCl$_3$) δ 1.24 (t, J=7.0 Hz, 3H), 3.57 (q, J=7.0 Hz, 2H), 3.67 (t, J=5.2 Hz, 2H), 3.82 (q, J=5.2 Hz, 2H), 6.61 (d, J=8.5 Hz, 1H), 8.35 (d, J=8.5 Hz, 1H), 8.59 (br, 1H).

Reference Example 19

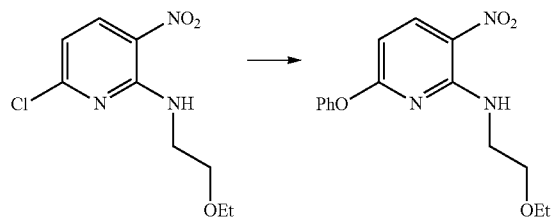 [SMILES: CCOCCNc1nc(Cl)ccc1[N+](=O)[O-] ; CCOCCNc1nc(Oc2ccccc2)ccc1[N+](=O)[O-]]

The object product was obtained in the same manner as in Reference Example 2 from the compound obtained in Reference Example 18.

$^1$H-NMR (CDCl$_3$) δ 1.18 (t, J=7.0 Hz, 3H), 3.39-3.50 (m, 6H), 6.20 (d, J=9.0 Hz, 1H), 7.12-7.17 (m, 2H), 7.25 (m, 1H), 7.37-7.44 (m, 2H), 8.42 (d, J=9.0 Hz, 1H), 8.66 (br, 1H).

Reference Example 20

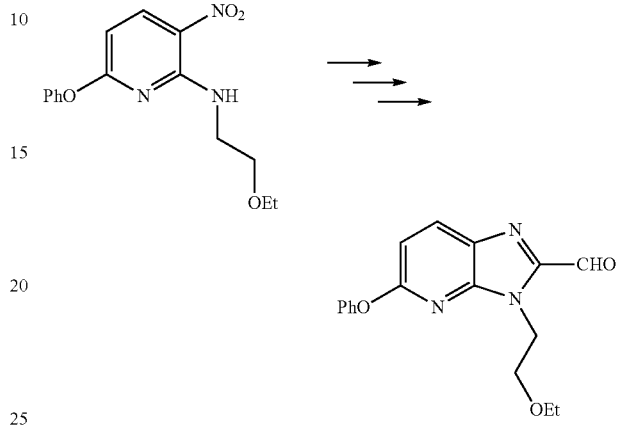

The object product was obtained in the same manner as in Reference Examples 3-5 from the compound obtained in Reference Example 19.

$^1$H-NMR (CDCl$_3$) δ 1.01 (t, J=7.0 Hz, 3H), 3.38 (q, J=7.0 Hz, 2H), 3.72 (t, J=5.6 Hz, 2H), 4.70 (t, J=5.6 Hz, 2H), 6.98 (d, J=8.8 Hz, 1H), 7.17-7.28 (m, 3H), 7.37-7.46 (m, 2H), 8.16 (d, J=8.8 Hz, 1H), 10.00 (s, 1H).

Example 79

N$^2$-{[3-(2-ethoxyethyl)-5-phenoxy-3H-imidazo[4,5-b]pyridin-2-yl]methyl}-L-alaninamide

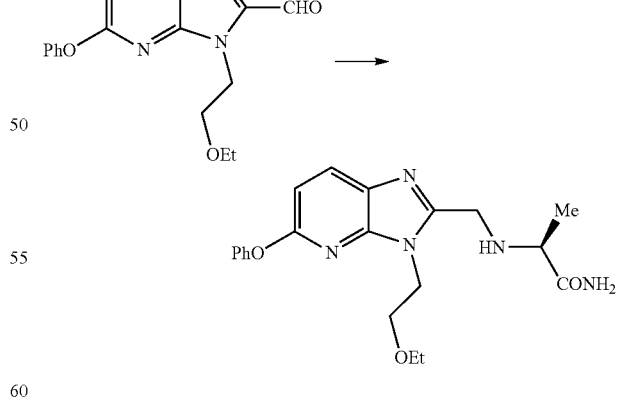

The object product was obtained in the same manner as in Example 1 from the compound obtained in Reference Example 20.

$^1$H-NMR (CDCl$_3$) δ 1.09 (t, J=7.0 Hz, 3H), 1.41 (d, J=7.0 Hz, 3H), 3.35 (q, J=7.0 Hz, 1H), 3.38 (q, J=7.0 Hz, 2H), 3.71 (t, J=5.1 Hz, 2H), 4.06 (d, J=15.0 Hz, 1H), 4.14 (d, J=15.0 Hz,

1H), 4.32 (t, J=5.1 Hz, 2H), 5.56 (brs, 1H), 6.67 (d, J=8.6 Hz, 1H), 7.11-7.21 (m, 3H), 7.26 (brs, 1H), 7.35-7.42 (m, 2H), 7.95 (d, J=8.6 Hz, 1H).

Example 80

N²-{[3-(2-ethoxyethyl)-5-phenoxy-3H-imidazo[4,5-b]pyridin-2-yl]methyl}glycinamide

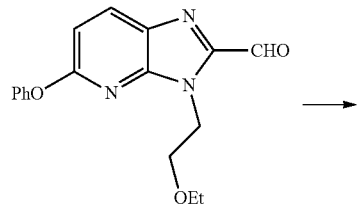

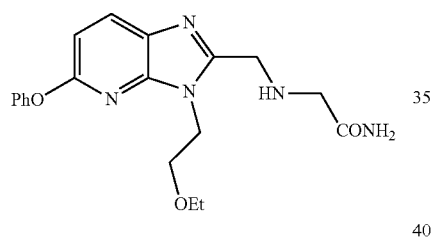

The object product was obtained in the same manner as in Example 2 from the compound obtained in Reference Example 20.

¹H-NMR (CDCl₃) δ 1.08 (t, J=7.0 Hz, 3H), 3.38 (q, J=7.0 Hz, 2H), 3.42 (s, 2H), 3.72 (t, J=4.9 Hz, 2H), 4.12 (s, 2H), 4.33 (t, J=4.9 Hz, 2H), 5.73 (brs, 1H), 6.76 (d, J=8.4 Hz, 1H), 7.11-7.22 (m, 3H), 7.26 (brs, 1H), 7.35-7.42 (m, 2H), 7.95 (d, J=8.4 Hz, 1H).

Reference Example 21

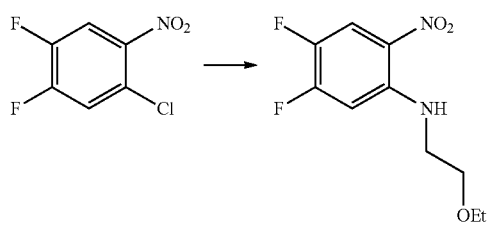 [SMILES: O=[N+]([O-])c1cc(F)c(F)cc1Cl ; CCOCCNc1cc(F)c(F)cc1[N+](=O)[O-]]

The object product was obtained in the same manner as in Reference Example 1 from 2,4,5-trifluoronitrobenzene.

¹H-NMR (CDCl₃) δ 1.25 (t, J=7.1 Hz, 3H), 3.43 (q, J=5.1 Hz, 2H), 3.57 (q, J=7.1 Hz, 2H), 3.72 (t, J=5.1 Hz, 2H), 6.66 (dd, J=12.4, 6.6 Hz, 1H), 8.05 (dd, J=10.2, 8.6 Hz, 1H), 8.29 (br, 1H).

Reference Example 22

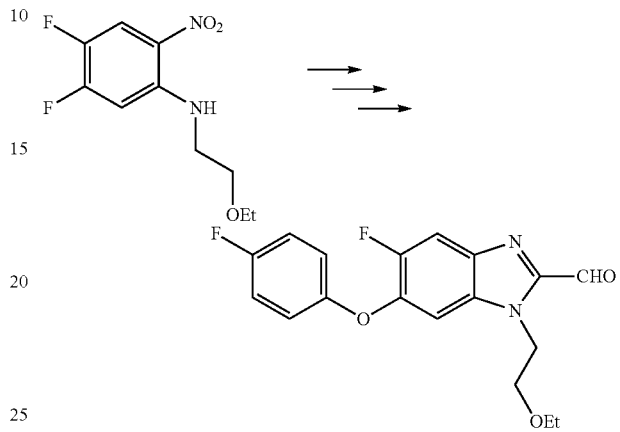

The object product was obtained in the same manner as in Reference Examples 2-5 from the compound obtained in Reference Example 21.

¹H-NMR (CDCl₃) δ 0.99 (t, J=7.0 Hz, 3H), 3.33 (q, J=7.0 Hz, 2H), 3.71 (t, J=5.1 Hz, 2H), 4.64 (t, J=5.1 Hz, 2H), 7.00-7.10 (m, 4H), 7.13 (d, J=7.1 Hz, 1H), 7.66 (d, J=10.3 Hz, 1H), 10.04 (s, 1H).

Example 81

N²-{[1-(2-ethoxyethyl)-5-fluoro-6-(4-fluorophenoxy)-1H-benzimidazol-2-yl]methyl}-L-alaninamide The object product was obtained in the same manner as in Example 1 from the compound obtained in Reference Example 22.

¹H-NMR (CDCl₃) δ 1.07 (t, J=7.0 Hz, 3H), 1.41 (d, J=7.0 Hz, 3H), 3.32 (q, J=7.0 Hz, 1H), 3.37 (q, J=7.0 Hz, 2H), 3.66 (t, J=5.1 Hz, 2H), 4.02 (d, J=14.7 Hz, 1H), 4.11 (d, J=14.7 Hz,

1H), 4.17-4.32 (m, 2H), 5.38 (brs, 1H), 6.90-7.05 (m, 5H), 7.16 (brs, 1H), 7.52 (d, J=12.1 Hz, 1H).

Reference Example 23

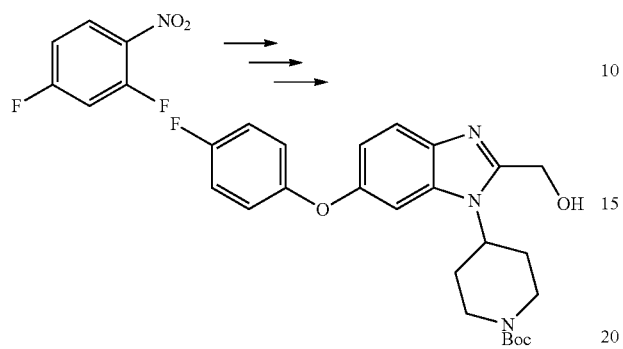

The object product was obtained in the same manner as in Reference Examples 1-4 from 2,4-difluoronitrobenzene, 4-amino-(1-tert-butoxycarbonyl)piperidine and 4-fluorophenol.

$^1$H-NMR (CDCl$_3$) δ 1.48 (s, 9H), 1.91-1.95 (m, 2H), 2.22-2.37 (m, 2H), 2.76-2.93 (m, 2H), 4.30 (br, 2H), 4.60 (m, 1H), 4.86 (s, 2H), 6.86-7.05 (m, 5H), 7.14 (d, J=2.0 Hz, 1H), 7.58 (d, J=8.8 Hz, 1H).

Reference Example 24

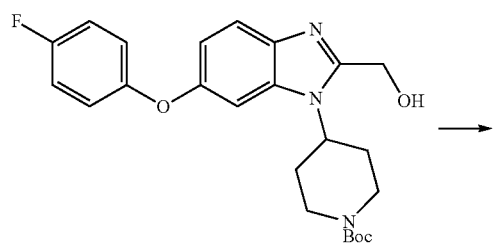

The object product was obtained in the same manner as in Reference Example 5 from the compound obtained in Reference Example 23.

$^1$H-NMR (CDCl$_3$) δ 1.48 (s, 9H), 1.89-1.93 (m, 2H), 2.23-2.38 (m, 2H), 2.85-2.94 (m, 2H), 4.33 (br, 2H), 5.63 (m, 1H), 6.99-7.10 (m, 5H), 7.18 (d, J=2.0 Hz, 1H), 7.86 (d, J=8.8 Hz, 1H), 10.04 (s, 1H).

Example 82 tert-butyl 4-[2-({[(2S)-1-amino-1-oxopropan-2-yl]amino}methyl)-6-(4-fluorophenoxy)-1H-benzimidazol-1-yl]piperidine-1-carboxylate

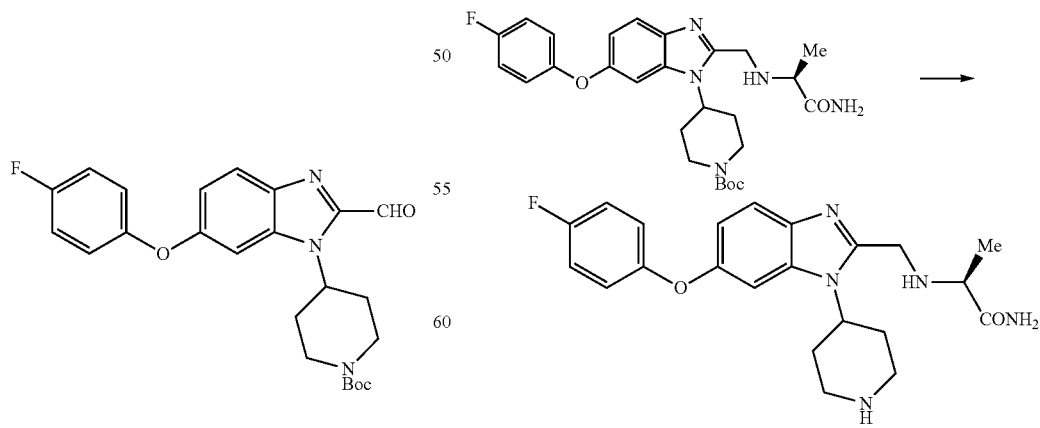

The object product was obtained in the same manner as in Example 1 from the compound obtained in Reference Example 24.

$^1$H-NMR (CDCl$_3$) δ 1.38 (d, J=7.0 Hz, 3H), 1.48 (s, 9H), 1.86-1.89 (m, 2H), 2.30-2.34 (m, 2H), 2.81-2.89 (m, 2H), 3.28 (q, J=7.0 Hz, 1H), 4.02 (d, J=14.7 Hz, 1H), 4.10 (d, J=14.7 Hz, 1H), 4.31-4.42 (m, 3H), 6.02 (brs, 1H), 6.87-7.04 (m, 6H), 7.15 (d, J=2.0 Hz, 1H), 7.64 (d, J=8.8 Hz, 1H).

Example 83

N$^2$-{[6-(4-fluorophenoxy)-1-(piperidin-4-yl)-1H-benzimidazol-2-yl]methyl}-L-alaninamide To a solution of the compound (68 mg, 0.13 mmol) obtained in Example 82 in dichloromethane (1.3 ml) was added trifluoroacetic acid (260 μL), and the mixture was stirred at room temperature for 1 hr. Aqueous sodium hydroxide solution was added to the reaction mixture, and the mixture was extracted with chloroform. The organic layer was washed with saturated brine, dried over magnesium sulfate, and concentrated under reduced pressure. The residue was purified by silica gel column (ethyl acetate:methanol=99:1-80:20) to give the object product (38 mg, 71%).

¹H-NMR (CDCl₃) δ 1.41 (d, J=7.0 Hz, 3H), 1.86-1.89 (m, 2H), 2.26-2.40 (m, 2H), 2.72-2.81 (m, 2H), 3.26-3.33 (m, 3H), 4.02 (d, J=14.7 Hz, 1H), 4.10 (d, J=14.7 Hz, 1H), 4.30 (m, 1H), 5.89 (brs, 1H), 6.89-7.07 (m, 6H), 7.33 (d, J=2.0 Hz, 1H), 7.65 (d, J=8.8 Hz, 1H).

Reference Example 25

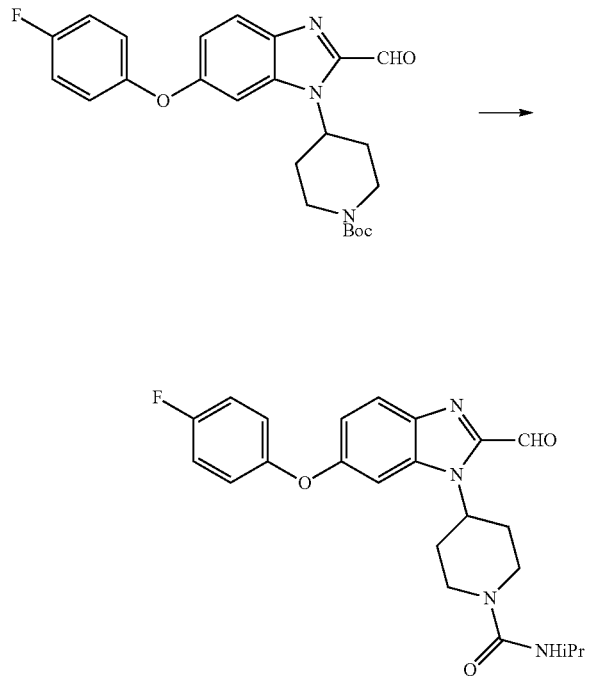

To a solution of the compound (300 mg, 0.68 mmol) obtained in Reference Example 24 in dichloromethane (6.8 ml) was added trifluoroacetic acid (1.4 ml), and the mixture was stirred at room temperature for 1 hr. Aqueous sodium hydroxide solution was added to the reaction mixture, and the mixture was extracted with chloroform. The organic layer was washed with saturated brine, dried over magnesium sulfate, and concentrated under reduced pressure. The obtained residue was dissolved in dichloromethane (6.8 mL), triethylamine (142 μL, 1.02 mmol) and isopropyl isocyanate (100 μL, 1.02 mmol) were added thereto, and the mixture was stirred at room temperature for 1 hr. Water was added to the reaction mixture, and the mixture was extracted with chloroform. The organic layer was washed with saturated brine, dried over magnesium sulfate, and concentrated under reduced pressure. The residue was purified by silica gel column (chloroform:methanol=99:1-85:15) to give the object product (280 mg, 97%).

¹H-NMR (CDCl₃) δ 1.18 (d, J=6.6 Hz, 6H), 1.92-1.97 (m, 2H), 2.28-2.42 (m, 2H), 2.91-3.01 (m, 2H), 4.01 (m, 1H), 4.12-4.17 (m, 2H), 4.33 (m, 1H), 5.65 (m, 1H), 6.97-7.10 (m, 5H), 7.20 (d, J=2.0 Hz, 1H), 7.86 (d, J=8.8 Hz, 1H), 10.04 (s, 1H).

Example 84

4-[2-({[(2S)-1-amino-1-oxopropan-2-yl]amino}methyl)-6-(4-fluorophenoxy)-1H-benzimidazol-1-yl]-N-(propan-2-yl)piperidine-1-carboxamide

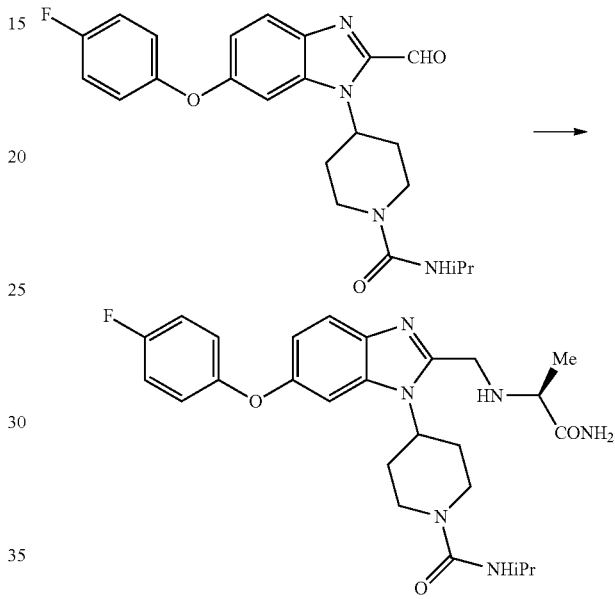

The object product was obtained in the same manner as in Example 1 from the compound obtained in Reference Example 25.

¹H-NMR (CDCl₃) δ 1.17 (d, J=6.6 Hz, 6H), 1.38 (d, J=7.0 Hz, 3H), 1.90-1.92 (m, 2H), 2.30-2.40 (m, 2H), 2.87-2.94 (m, 2H), 3.27 (q, J=7.0 Hz, 1H), 3.93-4.18 (m, 5H), 4.36-4.45 (m, 2H), 5.73 (brs, 1H), 6.89-7.03 (m, 6H), 7.16 (d, J=2.0 Hz, 1H), 7.65 (d, J=8.8 Hz, 1H).

Example 85

N²-{[1-(1-acetylpiperidin-4-yl)-6-(4-fluorophenoxy)-1H-benzimidazol-2-yl]methyl}-L-alaninamide

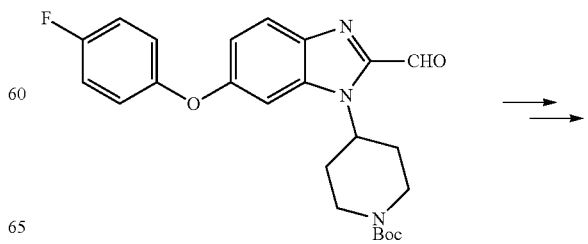

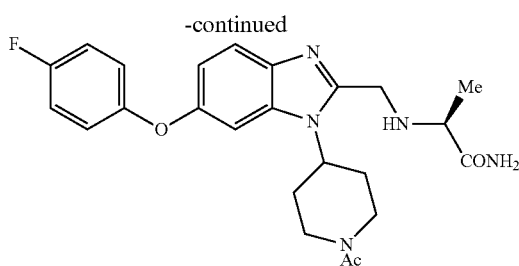

The object product was obtained in the same manner as in Reference Example 25 and Example 1 from the compound obtained in Reference Example 24 and acetyl chloride.

$^1$H-NMR (CDCl$_3$) δ 1.38 (d, J=7.0 Hz, 3H), 1.89-2.46 (m, 3H), 2.16 (s, 3H), 2.67 (m, 1H), 3.18-3.32 (m, 2H), 3.65 (m, 1H), 3.99-4.13 (m, 3H), 4.52 (m, 1H), 4.89 (m, 1H), 5.85 (brs, 1H), 6.88-7.05 (m, 6H), 7.11 (d, J=2.0 Hz, 1H), 7.65 (d, J=8.8 Hz, 1H).

Example 86

N$^2$-({6-(4-fluorophenoxy)-1-[1-(methylsulfonyl)piperidin-4-yl]-1H-benzimidazol-2-yl}methyl)-L-alaninamide

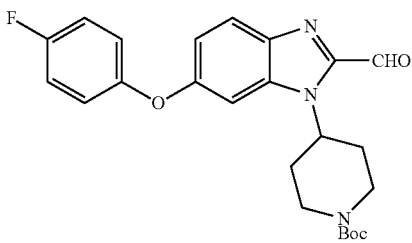

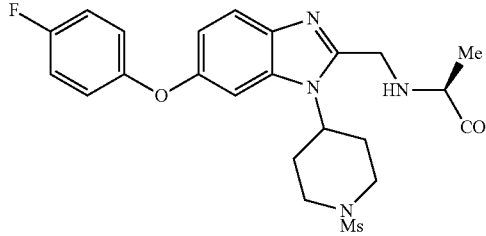

The object product was obtained in the same manner as in Reference Example 25 and Example 1 from the compound obtained in Reference Example 24 and methanesulfonyl chloride.

$^1$H-NMR (CDCl$_3$) δ 1.37 (d, J=6.8 Hz, 3H), 2.00-2.16 (m, 3H), 2.48-2.61 (m, 2H), 2.88 (m, 1H), 2.86 (s, 3H), 3.25 (q, J=6.8 Hz, 1H), 3.99-4.16 (m, 4H), 4.46 (m, 1H), 5.87 (brs, 1H), 6.81 (brs, 1H), 6.89-7.05 (m, 5H), 7.21 (d, J=2.0 Hz, 1H), 7.65 (d, J=8.8 Hz, 1H).

Reference Example 26

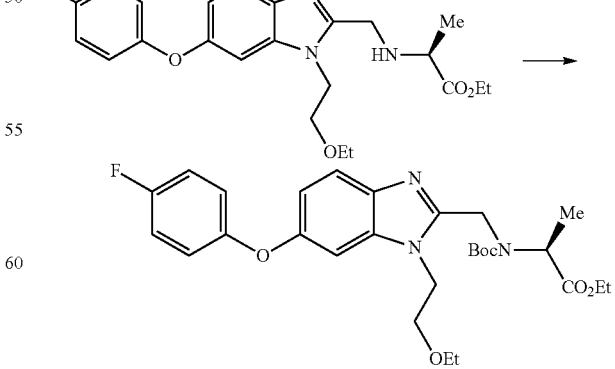

To a solution of the compound (2.28 g, 6.9 mmol) obtained in Reference Example 7 in tetrahydrofuran (70 mL) were added (L)-alanine ethyl ester hydrochloride (2.15 g, 14 mmol), triethylamine (1.95 ml, 14 mmol) and sodium sulfate (10 g), and the mixture was stirred at room temperature. After stirring for 1 hr, sodium cyanoborohydride (503 mg, 8 mmol) was added thereto, and the mixture was stirred for 4 hr. The reaction mixture was poured into saturated aqueous sodium hydrogen carbonate solution, and the mixture was extracted with ethyl acetate. The organic layer was extracted, washed with water and saturated brine, dried over sodium sulfate, and concentrated under reduced pressure. The residue was purified by silica gel column (chloroform:methanol=100:0-95:5) to give the object product (1.78 g, 60%).

$^1$H-NMR (CDCl$_3$) δ 1.08 (t, J=7.0 Hz, 3H), 1.28 (t, J=7.1 Hz, 3H), 1.35 (d, J=7.0 Hz, 3H), 3.38 (q, J=7.0 Hz, 2H), 3.48 (q, J=7.1 Hz, 1H), 3.70 (t, J=5.3 Hz, 2H), 4.02 (d, J=13.9 Hz, 1H), 4.10-4.23 (m, 3H), 4.31-4.42 (m, 2H), 6.90-7.05 (m, 6H), 7.66 (d, J=8.6 Hz, 1H).

Reference Example 27

To a solution of the compound (2.79 g, 6.5 mmol) obtained in Reference Example 26 in acetonitrile (65 mL) was added di-t-butyl dicarbonate (1.64 g, 7.5 mmol), and the mixture was stirred with heating at 60° C. for 3 hr and at 100° C. for 3 hr. After cooling to room temperature, the mixture was concentrated under reduced pressure, and the residue was purified by silica gel column (hexane:ethyl acetate=100:0-70: 30) to give the object product (2.24 g, 65%).

$^1$H-NMR (CDCl$_3$) δ 1.00-1.18 (m, 6H), 1.40 (d, J=7.1 Hz, 3H), 1.44 (s, 9H), 3.38 (q, J=7.0 Hz, 2H), 3.68 (t, J=5.9 Hz, 2H), 3.86-4.12 (m, 2H), 4.19-4.55 (m, 3H), 4.75 (d, J=15.4 Hz, 1H), 4.98 (d, J=15.4 Hz, 1H), 6.90-7.08 (m, 6H), 7.64 (d, J=8.8 Hz, 1H).

Reference Example 28

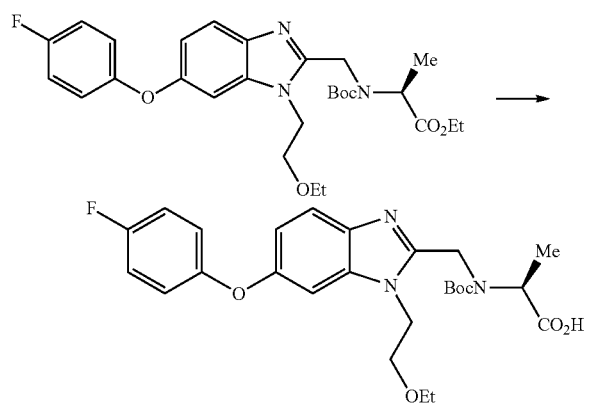

To a solution of the compound (2.24 g, 4.2 mmol) obtained in Reference Example 27 in ethanol (40 mL) was added 2 mol/L aqueous sodium hydroxide solution (4.2 ml, 8.4 mmol) in an ice bath. After stirring for 30 min under the same conditions, water was added to the reaction mixture, and the aqueous layer was washed with ether. The aqueous layer was adjusted to pH=4 with 2 mol/L hydrochloric acid, and the mixture was extracted with chloroform. The organic layer was extracted, washed with saturated brine and dried over sodium sulfate to give the object product (2.02 g, 96%).

$^1$H-NMR (CDCl$_3$) δ 1.11 (t, J=7.0 Hz, 3H), 1.49 (s, 9H), 1.55 (d, J=7.2 Hz, 3H), 3.30-3.50 (m, 2H), 3.63-3.75 (m, 2H), 3.90 (brs, 1H), 4.13-4.29 (m, 2H), 4.54 (brs, 1H), 5.27 (brs, 1H), 6.91-7.08 (m, 6H), 7.63 (d, J=8.6 Hz, 1H).

Example 87

N$^2$-{[1-(2-ethoxyethyl)-6-(4-fluorophenoxy)-1H-benzimidazol-2-yl]methyl}-N-(2-hydroxy-2-methyl-propyl)-L-alaninamide

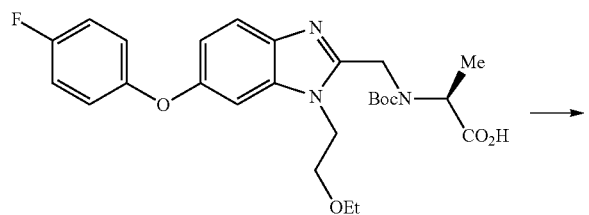

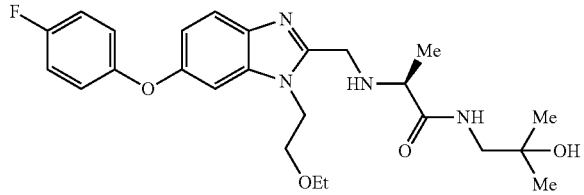

To a solution of the compound (53 mg, 0.1 mmol) obtained in Reference Example 28 in dichloromethane (2 mL) were added 1-amino-2-methylpropan-2-ol (18 mg, 0.2 mmol) and PyBOP [registered trade mark, benzotriazol-1-yl-oxy-tris (pyrrolidino)phosphonium hexafluorophosphate (benzotriazol-1-yl-oxy-tris(pyrrolidino)phosphonium hexafluorophosphate)] (52 mg, 0.1 mmol), and the mixture was stirred at room temperature. After 16 hr, 10% aqueous citric acid solution was added to the reaction mixture, and the mixture was extracted with ethyl acetate. The organic layer was extracted, washed with water and saturated brine, and dried over sodium sulfate. After concentration under reduced pressure, the residue was purified by silica gel column (chloroform:methanol=100:0-98:2) to give the object product (51 mg, 89%). The product was dissolved in ethyl acetate (1 mL), 4 mol/L hydrogen chloride-ethyl acetate solution (1 ml, 4 mmol) was added thereto, and the mixture was stirred at room temperature. After 14 hr, the mixture was concentrated under reduced pressure. To the obtained residue was added 2 mol/L aqueous sodium hydroxide solution, and the mixture was extracted with chloroform. The organic layer was extracted, washed with saturated brine, and dried over sodium sulfate. After concentration under reduced pressure, the residue was purified by silica gel column (chloroform:methanol=100:0-95:5) to give the object product (32 mg, 76%).

$^1$H-NMR (CDCl$_3$) δ 1.10 (t, J=7.0 Hz, 3H), 1.29 (s, 6H), 1.36 (d, J=6.8 Hz, 3H), 3.21 (dd, J=5.3, 3.6 Hz, 1H), 3.29-3.51 (m, 4H), 3.61-3.73 (m, 2H), 3.97 (d, J=14.3 Hz, 1H), 4.11 (d, J=14.3 Hz, 1H), 4.21 (dt, J=15.3, 4.2 Hz, 1H), 4.33 (m, 1H), 6.90-7.07 (m, 6H), 7.68 (dd, J=8.3, 0.9 Hz, 1H), 7.83 (brt, J=6.0 Hz, 1H).

Examples 88-90

The compounds of Examples 88-90 shown in Table 13 were prepared according to the methods described in the above-mentioned Reference Examples and Examples or methods analogous thereto.

TABLE 13

| Example | structural formula | $^1$H-NMR(CDCl$_3$) δ |
|---|---|---|
| 88 | 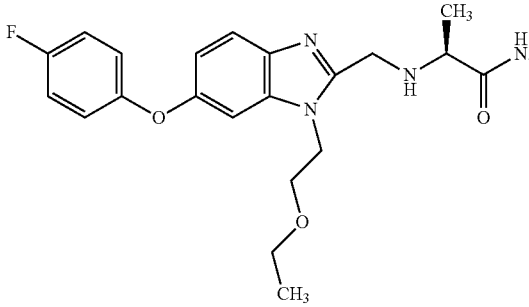 | 1.08 (t, J = 7.0 Hz, 3H), 1.37 (d, J = 7.0 Hz, 3H), 3.32 (q, J = 7.0 Hz, 1H), 3.35 (s, 3H), 3.38 (q, J = 7.0 Hz, 2H), 3.43-3.52 (m, 4H), 3.67 (t, J = 5.2 Hz, 2H), 3.99 (d, J = 14.7 Hz, 1H), 4.08 (d, J = 14.7 Hz, 1H), 4.26 (t, J = 5.2 Hz, 2H), 6.91-7.07 (m, 6H), 7.53 (brs, 1H), 7.64-7.69 (m, 1H). |
| 89 | 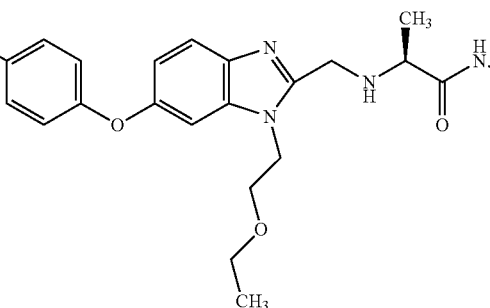 | 1.08 (t, J = 7.1 Hz, 3H), 1.37 (d, J = 6.8 Hz, 3H), 2.41-2.53 (m, 6H), 3.25-3.45 (m, 5H), 3.62-3.72 (m, 6H), 4.00 (d, J = 14.9 Hz, 1H), 4.08 (d, J = 14.9 Hz, 1H), 4.17-4.33 (m, 2H), 6.94-7.05 (m, 6H), 7.48 (brt, J = 5.2 Hz, 1H), 7.66 (m, 1H). |
| 90 | 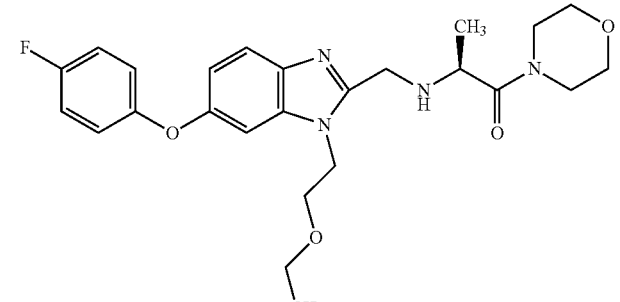 | 1.08 (t, J = 7.1 Hz, 3H), 1.19 (d, J = 7.0 Hz, 3H), 3.31-3.43 (m, 3H), 3.44-3.80 (m, 10H), 3.96 (d, J = 14.1 Hz, 1H), 4.11 (d, J = 14.1 Hz, 1H), 4.32 (m, 1H), 4.46 (m, 1H), 6.90-7.06 (m, 6H), 7.63 (d, J = 8.6 Hz, 1H). |

Reference Example 29

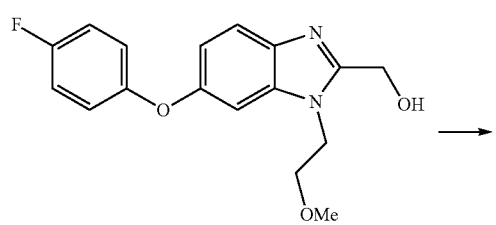

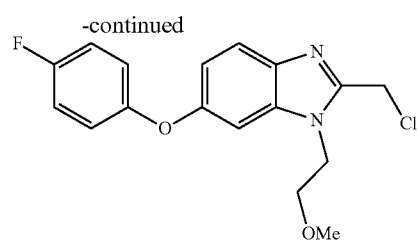

To a solution of alcohol (500 mg, 1.58 mmol) obtained in the same manner as in Reference Examples 1-4 in dichloromethane (16 mL) was added thionyl chloride (342 μL, 4.74 mmol), and the mixture was stirred at room temperature for 2 hr. The reaction mixture was concentrated, and the obtained residue was dissolved in chloroform, aqueous sodium hydroxide solution was added thereto. The mixture was extracted with chloroform, and the organic layer was washed with saturated brine, dried over magnesium sulfate, and concentrated under reduced pressure to give the object product (508 mg, 96%).

$^1$H-NMR (CDCl$_3$) δ 3.27 (s, 3H), 3.67 (t, J=5.1 Hz, 2H), 4.38 (t, J=5.1 Hz, 2H), 4.92 (s, 2H), 6.96-7.06 (m, 6H), 7.58 (d, J=8.4 Hz, 1H).

Example 91

N$^2$-{[6-(4-fluorophenoxy)-1-(2-methoxyethyl)-1H-benzimidazol-2-yl]methyl}-2-methylalaninamide

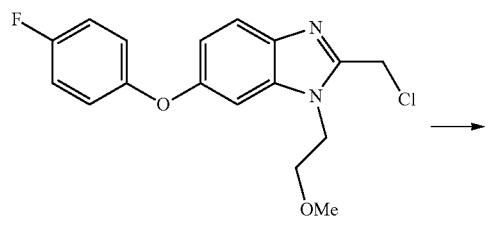

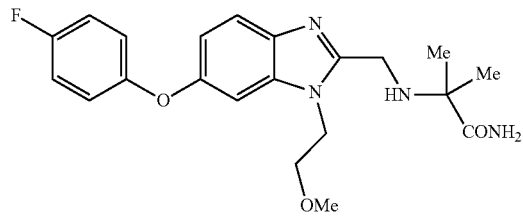

To a solution of the compound (300 mg, 0.90 mmol) obtained in Reference Example 29 in acetonitrile (4.5 ml) were added 2,2-dimethylglycine (138 mg, 1.35 mmol), diisopropylethylamine (321 µL, 1.80 mmol) and sodium iodide (135 mg, 0.90 mmol), and the mixture was heated to 50° C. and stirred overnight. Water was added thereto, the mixture was extracted with chloroform, and the organic layer was washed with saturated brine, dried over magnesium sulfate, and concentrated under reduced pressure. The residue was purified by silica gel column (ethyl acetate:methanol=99:1-80:20) to give the object product (169 mg, 47%).

$^1$H-NMR (CDCl$_3$) δ 1.45 (s, 6H), 3.26 (s, 3H), 3.66 (t, J=5.0 Hz, 2H), 4.00 (s, 2H), 4.25 (t, J=5.0 Hz, 2H), 5.57 (brs, 1H), 6.94-7.05 (m, 6H), 7.46 (brs, 1H), 7.67 (m, 1H).

Reference Example 30

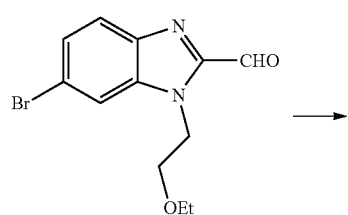

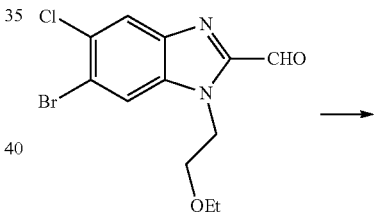

To a solution of the compound (0.84 g, 2.8 mmol) obtained in Reference Example 10 in N,N-dimethylformamide (30 ml) was added N-chlorosuccinimide (0.95 g, 7.1 mmol), and the mixture was heated to 40° C. After stirring overnight, water was added thereto, the mixture was extracted with ethyl acetate, and the organic layer was washed with saturated brine, dried over magnesium sulfate, concentrated under reduced pressure and directly used for the next reaction.

$^1$H-NMR (CDCl$_3$) δ 1.07 (t, J=7.0 Hz, 3H), 3.39 (q, J=7.0 Hz, 2H), 3.76 (t, J=5.1 Hz, 2H), 4.72 (t, J=5.1 Hz, 2H), 8.01-8.02 (m, 2H), 10.09 (s, 1H).

Reference Example 31

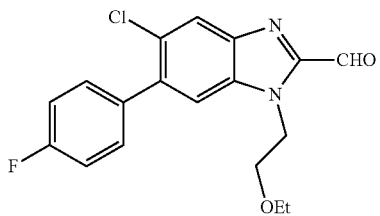

The object product was obtained in the same manner as in Reference Example 11 from the compound obtained in Reference Example 30.

$^1$H-NMR (CDCl$_3$) δ 1.05 (t, J=7.0 Hz, 3H), 3.38 (q, J=7.0 Hz, 2H), 3.77 (t, J=5.1 Hz, 2H), 4.76 (t, J=5.1 Hz, 2H), 7.12-7.20 (m, 3H), 7.40-7.46 (m, 2H), 8.02 (s, 1H), 10.12 (s, 1H).

Example 92

N$^2$-{[5-chloro-1-(2-ethoxyethyl)-6-(4-fluorophenyl)-1H-benzimidazol-2-yl]methyl}-L-alaninamide

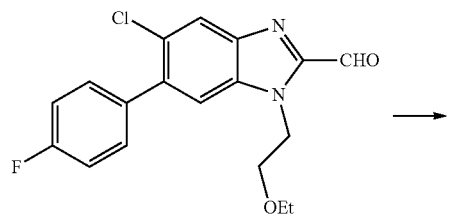

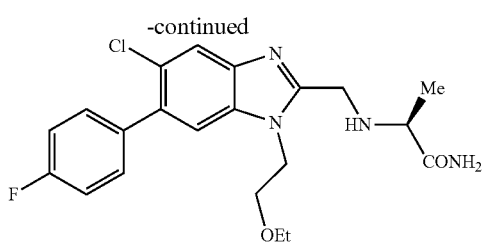

The object product was obtained in the same manner as in Example 1 from the compound obtained in Reference Example 31.

$^1$H-NMR (CDCl$_3$) δ 1.09 (t, J=7.0 Hz, 3H), 1.41 (t, J=7.0 Hz, 3H), 3.32-3.42 (m, 3H), 3.71 (t, J=5.1 Hz, 2H), 4.05 (d, J=14.6 Hz, 1H), 4.14 (d, J=14.6 Hz, 1H), 4.23-4.38 (m, 2H), 5.39 (brs, 1H), 7.11-7.17 (m, 3H), 7.21 (brs, 1H), 7.41-7.45 (m, 2H), 7.83 (s, 1H).

Examples 93-108

The compounds of Examples 93-108 shown in Tables 14-16 were prepared according to the methods described in the above-mentioned Reference Examples and Examples or methods analogous thereto.

TABLE 14

| Example | structural formula | $^1$H-NMR(CDCl$_3$) δ |
|---|---|---|
| 93 | | 1.11 (t, J = 7.0 Hz, 3H), 1.43 (d, J = 7.0 Hz, 3H), 3.32-3.45 (m, 3H), 3.82 (t, J = 5.1 Hz, 2H), 4.07 (d, J = 14.9 Hz, 1H), 4.17 (d, J = 14.9 Hz, 1H), 4.65-4.68 (m, 2H), 5.35 (brs, 1H), 6.87-7.04 (m, 6H), 7.58 (d, J = 8.8 Hz, 1H). |
| 94 | | 1.09 (t, J = 7.0 Hz, 3H), 1.24 (d, J = 7.0 Hz, 6H), 1.41 (d, J = 7.0 Hz, 3H), 2.90 (m, 1H), 3.31-3.40 (m, 3H), 3.68 (t, J = 5.1 Hz, 2H), 4.04 (d, J = 14.9 Hz, 1H), 4.11 (d, J = 14.9 Hz, 1H), 4.20-4.29 (m, 2H), 5.33 (brs, 1H), 6.90-6.99 (m, 4H), 7.16-7.19 (m, 2H), 7.26 (brs, 1H), 7.66(m, 1H). |
| 95 | | 1.09 (t, J = 7.0 Hz, 3H), 1.41 (d, J = 7.0 Hz, 3H), 2.06-2.13 (m, 2H), 2.85-2.90 (m, 4H), 3.31-3.40 (m, 3H), 3.68 (t, J = 5.1 Hz, 2H), 4.03 (d, J = 14.6 Hz, 1H), 4.11 (d, J = 14.6 Hz, 1H), 4.18-4.30 (m, 2H), 5.33 (brs, 1H), 6.79 (d, J = 8.1 Hz, 1H), 6.86 (m, 1H), 6.97-6.99 (m, 3H), 7.15 (d, J = 8.3 Hz, 1H), 7.65 (d, J = 9.3 Hz, 1H). |

TABLE 14-continued

| Example | structural formula | $^1$H-NMR(CDCl$_3$) δ |
|---|---|---|
| 96 | (structure) | 1.38 (t, J = 7.1 Hz, 3H), 1.42 (d, J = 7.0 Hz, 3H), 3.32 (q, J = 7.0 Hz, 1H), 3.99 (d, J = 14.8 Hz, 1H), 4.06 (d, J = 14.8 Hz, 1H), 4.06-4.16 (m, 2H), 5.50 (br, 1H), 6.88-7.00 (m, 4H), 7.09-7.16 (m, 3H), 7.65 (m, 1H). |
| 97 | (structure) | 1.40 (t, J = 7.3 Hz, 3H), 1.42 (d, J = 7.0 Hz, 3H), 3.32 (q, J = 7.0 Hz, 1H), 4.00 (d, J = 15.0 Hz, 1H), 4.08 (d, J = 15.0 Hz, 1H), 4.09-4.20 (m, 2H), 5.52 (br, 1H), 6.71 (m, 1H), 6.80 (m, 1H), 6.87-7.15 (m, 4H), 7.69 (d, J = 8.6 Hz, 1H). |

TABLE 15

| Example | structural formula | $^1$H-NMR(CDCl$_3$) δ |
|---|---|---|
| 98 | (structure) | 1.39 (t, J = 7.1 Hz, 3H), 1.42 (d, J = 6.8 Hz, 3H), 3.31 (q, J = 6.8 Hz, 1H), 3.99 (d, J = 14.8 Hz, 1H), 4.06 (d, J = 14.8 Hz, 1H), 4.07-4.17 (m, 2H), 5.48 (br, 1H), 6.80-7.12 (m, 6H), 7.65 (m, 1H). |
| 99 | (structure) | 0.95-1.05 (m, 2H), 1.13-1.23 (m, 2H), 1.43 (d, J = 7.0 Hz, 3H), 3.18 (m, 1H), 3.30 (q, J = 7.0 Hz, 1H), 4.08 (d, J = 14.4 Hz, 1H), 4.17 (d, J = 14.4 Hz, 1H), 5.52 (br, 1H), 6.80-7.06 (m, 4H), 7.13 (d, J = 2.4 Hz, 1H), 7.23 (br, 1H), 7.61 (d, J = 8.6 Hz, 1H). |
| 100 | (structure) | 0.98-1.08 (m, 2H), 1.15-1.25 (m, 2H), 1.44 (d, J = 6.8 Hz, 3H), 3.19 (m, 1H), 3.36 (q, J = 6.8 Hz, 1H), 4.10 (d, J = 15.4 Hz, 1H), 4.18 (d, J = 15.4 Hz, 1H), 5.44 (br, 1H), 6.93-7.00 (m, 3H), 7.14-7.26 (m, 4H), 7.66 (d, J = 8.6 Hz, 1H). |
| 101 | (structure) | 1.20 (s, 3H), 1.29 (s, 3H), 1.32 (d, J = 6.9 Hz, 3H), 2.33 (s, 3H), 3.34 (q, J = 6.9 Hz, 1H), 4.03 (d, J = 13.9 Hz, 1H), 4.07-4.1 (m, 3H), 5.91 (brs, 1H), 6.84-6.91 (m, 2H), 6.94-6.99 (m, 2H), 7.08-7.15 (m, 3H), 7.61 (m, 1H). |

TABLE 15-continued

| Example | structural formula | ¹H-NMR(CDCl₃) δ |
|---|---|---|
| 102 | 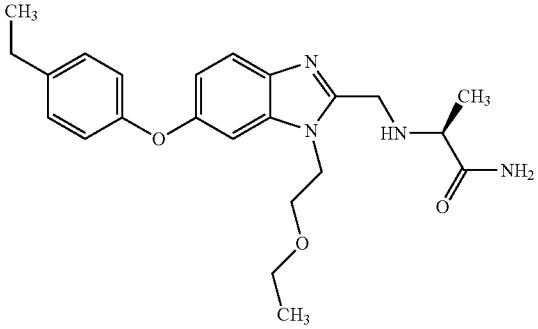 [SMILES: CCOCCn1c(CN[C@@H](C)C(N)=O)nc2ccc(Oc3ccc(CC)cc3)cc21] | 1.06 (t, J =7.0 Hz, 3H), 1.22 (t, J = 7.6 Hz, 3H), 1.38 (d, J = 6.8 Hz, 3H), 2.61 (q, J = 7.6 Hz, 2H), 3.30-3.38 (m, 3H), 3.65 (t, J = 5.1 Hz, 2H), 4.03 (d, J = 14.6 Hz, 1H), 4.09 (d, J = 14.6 Hz, 1H), 4.16-4.28 (m, 2H), 5.41 (brs, 1H), 6.89-6.96 (m, 4H), 7.11-7.13 (m, 2H), 7.21 (brs, 1H), 7.62 (m, 1H). |

TABLE 16

| Example | structural formula | ¹H-NMR(CDCl₃) δ |
|---|---|---|
| 103 | 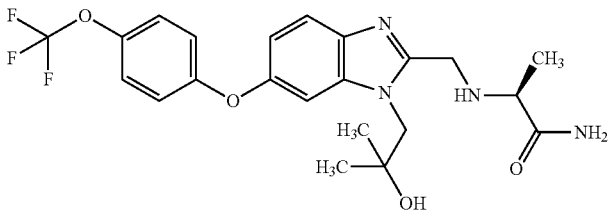 [SMILES: C[C@H](NCc1nc2ccc(Oc3ccc(OC(F)(F)F)cc3)cc2n1CC(C)(C)O)C(N)=O] | (CD₃OD) 1.24 (s, 3H), 1.25 (s, 3H), 1.61 (d, J = 7.1 Hz, 3H), 4.14 (q, J = 7.1 Hz, 1H), 4.27 (d, J = 15.3 Hz, 1H), 4.32 (d, J = 15.3 Hz, 1H), 4.62 (d, J = 15.1 Hz, 1H), 4.67 (d, J = 15.1 Hz, 1H), 7.00-7.10 (m, 3H), 7.22-7.28 (m, 2H), 7.37 (d, J = 2.0 Hz, 1H), 7.73 (d, J = 8.8 Hz, 1H). |
| 104 | 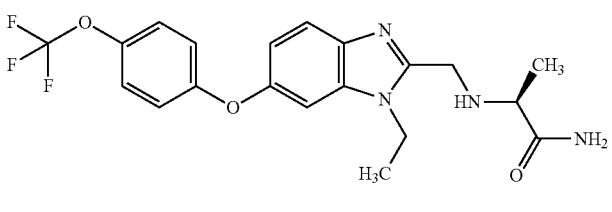 [SMILES: CCn1c(CN[C@@H](C)C(N)=O)nc2ccc(Oc3ccc(OC(F)(F)F)cc3)cc21] | 1.39 (t, J = 7.0 Hz, 3H), 1.43 (d, J = 7.0 Hz, 3H), 3.33 (q, J = 7.0 Hz, 1H), 4.00 (d, J = 14.9 Hz, 1H), 4.03 (d, J = 14.9 Hz, 1H), 4.14 (q, J = 7.0 Hz, 2H), 5.63 (brs, 1H), 6.94-7.03 (m, 4H), 7.09 (brs, 1H), 7.12-7.21 (m, 2H), 7.69 (d, J = 8.6 Hz, 1H). |
| 105 | 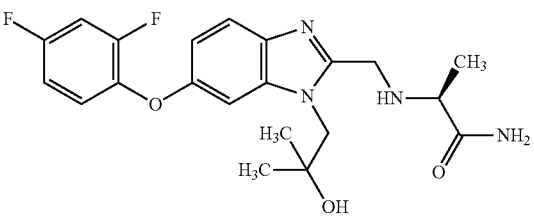 [SMILES: C[C@H](NCc1nc2ccc(Oc3ccc(F)cc3F)cc2n1CC(C)(C)O)C(N)=O] | (CD₃OD) 1.20 (s, 3H), 1.22 (s, 3H), 1.30 (d, J = 6.8 Hz, 3H), 3.25-3.36 (m, 1H), 4.03 (d, J = 14.3 Hz, 1H), 4.11 (d, J = 14.3 Hz, 1H), 4.18 (d, J = 15.0 Hz, 1H), 4.25 (d, J = 15.0 Hz, 1H), 6.87-6.96 (m, 2H), 7.03-7.18 (m, 3H), 7.57 (d, J = 8.8 Hz, 1H). |
| 106 | 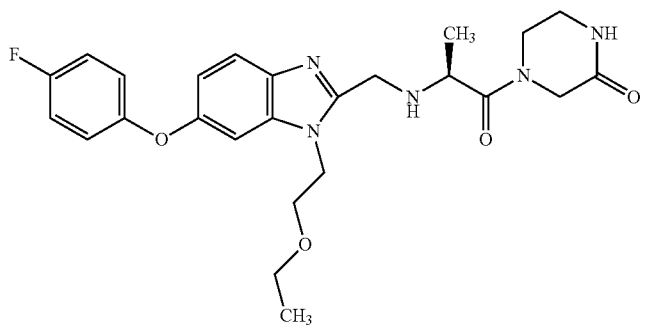 [SMILES: CCOCCn1c(CN[C@@H](C)C(=O)N2CCNC(=O)C2)nc2ccc(Oc3ccc(F)cc3)cc21] | 1.08 (t, J = 7.1 Hz, 3H), 1.21 (d, J = 7.0 Hz, 3H), 3.17-3.84 (m, 9H), 3.91-4.35 (m, 5H), 4.45 (m, 1H), 6.73-7.07 (m, 7H), 7.61 (t, J = 8.6 Hz, 1H). |

TABLE 16-continued

| Example | structural formula | ¹H-NMR(CDCl₃) δ |
|---|---|---|
| 107 | | 1.08 (t, J = 7.0 Hz, 3H), 1.23-1.32 (m, 3H), 2.82-4.54 (m, 16H), 6.88-7.08 (m, 6H), 7.63 (m, 1H). |
| 108 | | 1.08 (t, J = 7.0 Hz, 3H), 1.13-1.23 (m, 3H), 2.28 (m, 1H), 2.57-3.46 (m, 6H), 3.58-4.61 (m, 9H), 6.90-7.06 (m, 6H), 7.61 (m, 1H). |

Reference Example 32

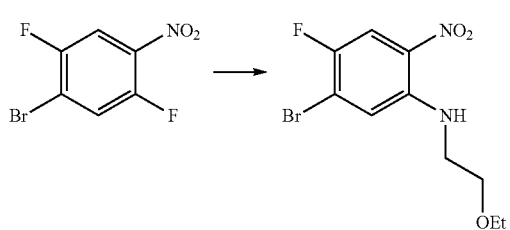 [SMILES: O=[N+]([O-])c1cc(F)c(Br)cc1F ; CCOCCNc1cc(Br)c(F)cc1[N+](=O)[O-]]

The object product was obtained in the same manner as in Reference Example 1 from 4-bromo-2,5-difluoronitrobenzene.

¹H-NMR (CDCl₃) δ 1.23 (t, J=7.0 Hz, 3H), 3.43 (q, J=5.2 Hz, 2H), 3.56 (q, J=7.0 Hz, 2H), 3.70 (t, J=5.2 Hz, 2H), 7.11 (d, J=5.9 Hz, 1H), 7.93 (d, J=8.6 Hz, 1H).

Reference Example 33

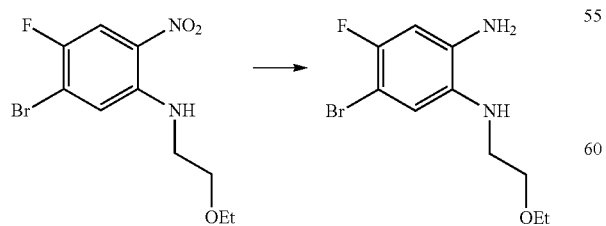

The object product was obtained in the same manner as in Reference Example 3-2 from the compound obtained in Reference Example 32.

¹H-NMR (CDCl₃) δ 1.21 (t, J=7.3 Hz, 3H), 3.51-3.58 (m, 4H), 3.65 (t, J=5.1 Hz, 2H), 6.49 (d, J=9.5 Hz, 1H), 6.72 (d, J=6.6 Hz, 1H).

Reference Example 34

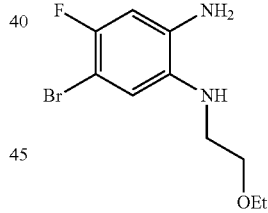

The object product was obtained in the same manner as in Reference Example 4 from the compound obtained in Reference Example 33.

¹H-NMR (CDCl₃) δ 1.12 (t, J=7.0 Hz, 3H), 3.43 (q, J=7.0 Hz, 2H), 3.75 (t, J=5.0 Hz, 2H), 4.38 (t, J=5.0 Hz, 2H), 4.88 (s, 2H), 7.45 (d, J=8.8 Hz, 1H), 7.53 (d, J=5.9 Hz, 1H).

Reference Example 35

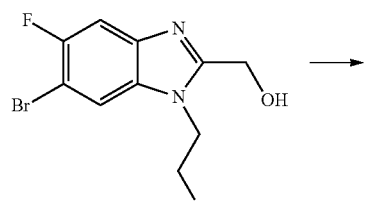

The object product was obtained in the same manner as in Reference Example 5 from the compound obtained in Reference Example 34.

¹H-NMR (CDCl₃) δ 1.07 (t, J=7.0 Hz, 3H), 3.40 (q, J=7.0 Hz, 2H), 3.76 (t, J=5.0 Hz, 2H), 4.73 (t, J=5.0 Hz, 2H), 7.63 (d, J=8.5 Hz, 1H), 7.87 (d, J=6.1 Hz, 1H), 10.09 (s, 1H).

Reference Example 36

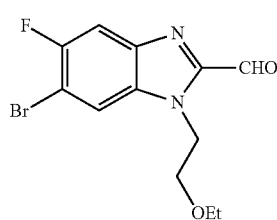

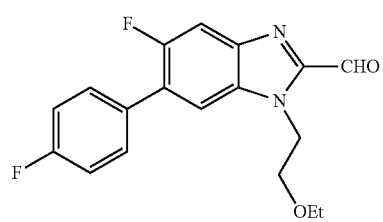

The object product was obtained in the same manner as in Reference Example 11 from the compound obtained in Reference Example 35.

¹H-NMR (CDCl₃) δ 1.06 (t, J=7.0 Hz, 3H), 3.40 (q, J=7.0 Hz, 2H), 3.78 (t, J=5.1 Hz, 2H), 4.78 (t, J=5.1 Hz, 2H), 7.15-7.27 (m, 2H), 7.54-7.66 (m, 4H), 10.11 (s, 1H).

Example 109

N²-{[1-(2-ethoxyethyl)-5-fluoro-6-(4-fluorophenyl)-1H-benzimidazol-2-yl]methyl}-L-alaninamide

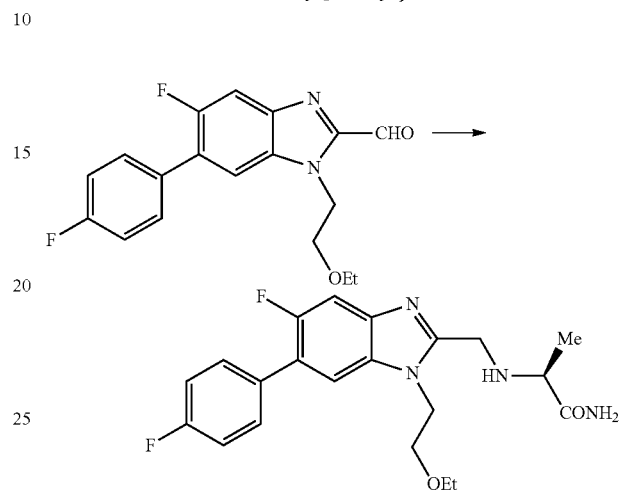

The object product was obtained in the same manner as in Example 2 from the compound obtained in Reference Example 36 and (L)-alaninamide hydrochloride.

¹H-NMR (CDCl₃) δ 1.09 (t, J=7.0 Hz, 3H), 1.40 (d, J=7.0 Hz, 3H), 3.31-3.41 (m, 3H), 3.72 (t, J=5.0 Hz, 2H), 4.04 (d, J=14.8 Hz, 1H), 4.12 (d, J=14.8 Hz, 1H), 4.26-4.38 (m, 2H), 5.82 (brs, 1H), 7.11-7.15 (m, 2H), 7.22 (brs, 1H), 7.27 (d, J=6.6 Hz, 1H), 7.47 (d, J=10.7 Hz, 1H), 7.49-7.53 (m, 2H).

Reference Example 37

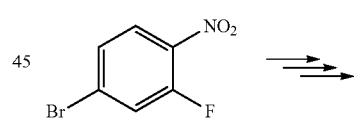

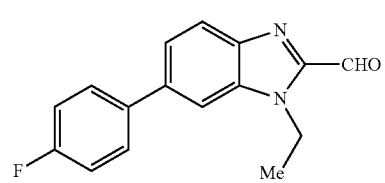

The object product was obtained in the same manner as in Reference Examples 9-11 from 4-bromo-2-fluoronitrobenzene, ethylamine and 4-fluorophenylboranic acid.

¹H-NMR (CDCl₃) δ 1.49 (t, J=7.2 Hz, 3H), 4.71 (q, J=7.2 Hz, 2H), 7.18 (t, J=8.5 Hz, 2H), 7.58-7.64 (m, 4H), 7.98 (d, J=9.3 Hz, 1H), 10.12 (s, 1H).

Example 110

N²-{[1-ethyl-6-(4-fluorophenyl)-1H-benzimidazol-2-yl]methyl}-L-alaninamide

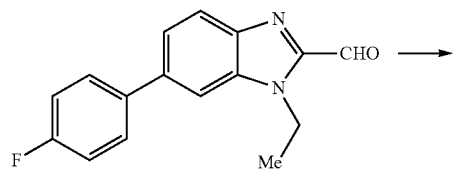

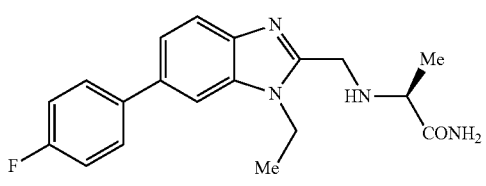

The object product was obtained in the same manner as in Example 2 from the compound obtained in Reference Example 37 and (L)-alaninamide hydrochloride.

¹H-NMR (CDCl₃) δ 1.42-1.48 (m, 6H), 3.32 (q, J=7.0 Hz, 1H), 4.03 (d, J=14.8 Hz, 1H), 4.11 (d, J=14.8 Hz, 1H), 4.24 (q, J=7.0 Hz, 2H), 5.60 (brs, 1H), 7.12-7.18 (m, 3H), 7.43-7.46 (m, 2H), 7.57-7.62 (m, 2H), 7.77 (m, 1H).

Reference Example 38

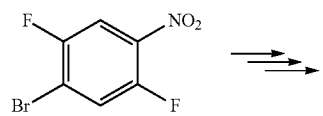

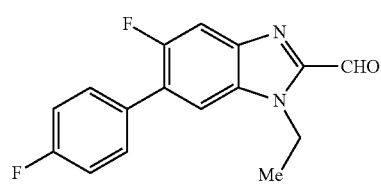

The object product was obtained in the same manner as in Reference Example 37 from 4-bromo-2,5-difluoronitrobenzene.

¹H-NMR (CDCl₃) δ 1.48 (t, J=7.2 Hz, 3H), 4.68 (q, J=7.2 Hz, 2H), 7.14-7.20 (m, 2H), 7.46 (d, J=6.6 Hz, 1H), 7.53-7.59 (m, 2H), 7.67 (d, J=10.5 Hz, 1H), 10.11 (s, 1H).

Example 111

N²-{[1-ethyl-5-fluoro-6-(4-fluorophenyl)-1H-benzimidazol-2-yl]methyl}-L-alaninamide

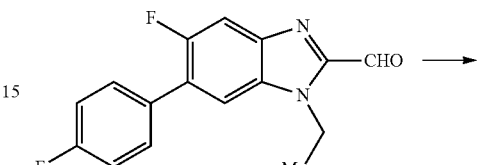

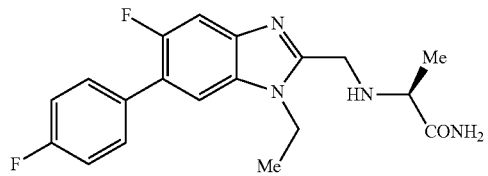

The object product was obtained in the same manner as in Example 2 from the compound obtained in Reference Example 38 and (L)-alaninamide hydrochloride.

¹H-NMR (CDCl₃) δ 1.42-1.46 (m, 6H), 3.31 (q, J=7.0 Hz, 1H), 4.01 (d, J=14.6 Hz, 1H), 4.08 (d, J=14.6 Hz, 1H), 4.20 (q, J=7.0 Hz, 2H), 5.41 (brs, 1H), 7.04 (brs, 1H), 7.13-7.18 (m, 2H), 7.28 (d, J=6.6 Hz, 1H), 7.49 (d, J=11.0 Hz, 1H), 7.52-7.55 (m, 2H).

Reference Example 39

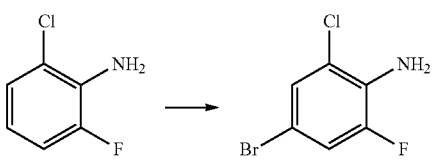 [SMILES: Nc1c(F)cccc1Cl ; Nc1c(F)cc(Br)cc1Cl]

To a solution of 2-chloro-6-fluoroaniline (2.5 g, 17.2 mmol) in chloroform (40 ml) was added bromine (2.75 g, 17.2 mmol), and the mixture was stirred at room temperature for 2 hr. The reaction mixture was poured into aqueous sodium thiosulfate solution, and the mixture was extracted with chloroform. The organic layer was washed with water and saturated brine, dried over sodium sulfate, and concentrated under reduced pressure. The residue was purified by silica gel column (hexane:ethyl acetate=9:1-3:1) to give the object product (3.21 g, 83%).

$^1$H-NMR (CDCl$_3$) δ 7.07 (dd, J=10.0, 2.0 Hz, 1H), 7.19 (t, J=2.0 Hz, 1H).

Reference Example 40

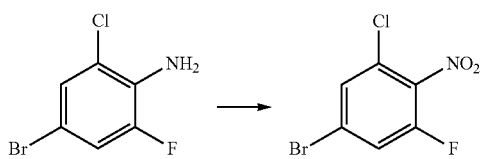 [SMILES: Nc1c(F)cc(Br)cc1Cl ; O=[N+]([O-])c1c(F)cc(Br)cc1Cl]

A solution of sodium peroxoborate tetrahydrate (11.0 g, 71.5 mmol) in acetic acid (50 ml) was heated to 55° C., and a solution of the compound (3.21 g, 14.3 mmol) obtained in Reference Example 39 in acetic acid (30 mL) was added dropwise over 1 hr. After stirring for 3 hr, the mixture was allowed to cool to room temperature and insoluble material was filtered off. The filtrate was poured into water, and the mixture was extracted with ethyl acetate. The organic layer was washed with water and saturated brine, dried over sodium sulfate, and concentrated under reduced pressure. The residue was purified by silica gel column (hexane:ethyl acetate=90:10-5:1) to give the object product (1.30 g, 36%).

$^1$H-NMR (CDCl$_3$) δ 7.39 (dd, J=8.3, 2.0 Hz, 1H), 7.50 (t, J=2.0 Hz, 1H).

Reference Example 41

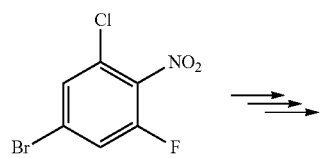

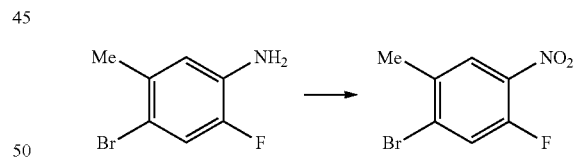

The object product was obtained in the same manner as in Reference Examples 9-11 from the compound obtained in Reference Example 40 and 4-fluorophenylboronic acid.

$^1$H-NMR (CDCl$_3$) δ 1.04 (t, J=7.0 Hz, 3H), 3.38 (q, J=7.0 Hz, 2H), 3.79 (t, J=5.1 Hz, 2H), 4.79 (t, J=5.1 Hz, 2H), 7.12-7.18 (m, 2H), 7.51-7.62 (m, 4H), 10.12 (s, 1H).

Example 112

N$^2$-{[4-chloro-1-(2-ethoxyethyl)-6-(4-fluorophenyl)-1H-benzimidazol-2-yl]methyl}-L-alaninamide

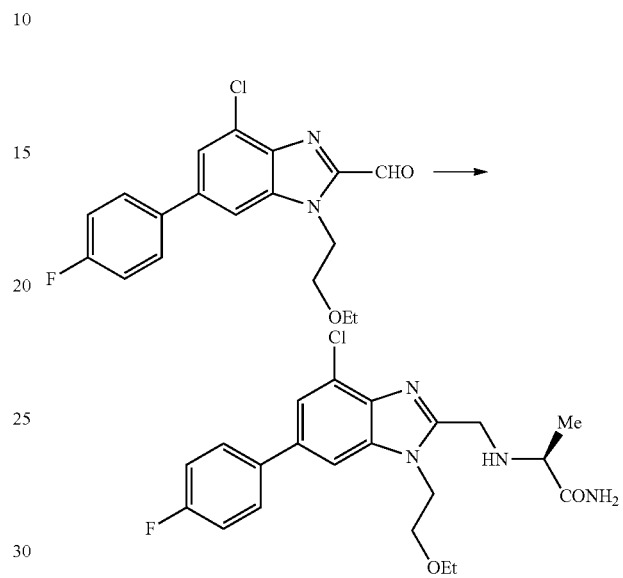

The object product was obtained in the same manner as in Example 2 from the compound obtained in Reference Example 41 and (L)-alaninamide hydrochloride.

$^1$H-NMR (CDCl$_3$) δ 1.09 (t, J=7.0 Hz, 3H), 1.40 (d, J=7.0 Hz, 3H), 3.30-3.41 (m, 3H), 3.74 (t, J=5.0 Hz, 2H), 4.07 (d, J=14.8 Hz, 1H), 4.15 (d, J=14.8 Hz, 1H), 4.30-4.44 (m, 2H), 5.65 (brs, 1H), 7.11-7.16 (m, 2H), 7.27 (brs, 1H), 7.35 (d, J=1.4 Hz, 1H), 7.46 (d, J=1.4 Hz, 1H), 7.53-7.57 (m, 2H).

Reference Example 42

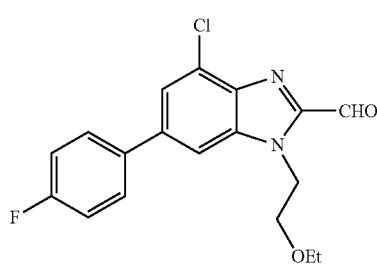

The object product was obtained in the same manner as in Reference Example 40 from 4-bromo-2-fluoro-5-methylaniline.

$^1$H-NMR (CDCl$_3$) δ 2.43 (s, 3H), 7.48 (d, J=10.0 Hz, 1H), 7.93 (d, J=7.8 Hz, 1H).

Reference Example 43

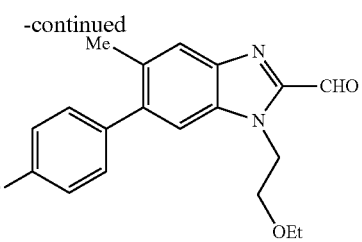

The object product was obtained in the same manner as in Reference Example 41 from the compound obtained in Reference Example 42.

$^1$H-NMR (CDCl$_3$) δ 1.05 (t, J=7.0 Hz, 3H), 2.34 (s, 3H), 3.40 (q, J=7.0 Hz, 2H), 3.77 (t, J=5.4 Hz, 2H), 4.75 (t, J=5.4 Hz, 2H), 7.11-7.16 (m, 2H), 7.29-7.33 (m, 2H), 7.40 (s, 1H), 7.70 (s, 1H), 10.10 (s, 1H).

Example 113

N$^2$-{[1-(2-ethoxyethyl)-6-(4-fluorophenyl)-5-methyl-1H-benzimidazol-2-yl]methyl}-L-alaninamide

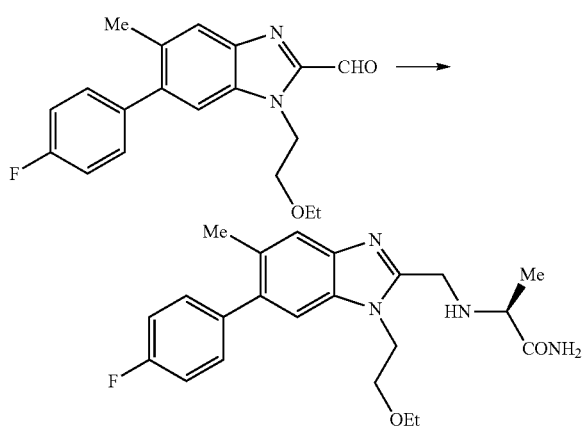

The object product was obtained in the same manner as in Example 2 from the compound obtained in Reference Example 43 and (L)-alaninamide hydrochloride.

$^1$H-NMR (CDCl$_3$) δ 1.09 (t, J=7.0 Hz, 3H), 1.41 (d, J=6.8 Hz, 3H), 2.33 (s, 3H), 3.30-3.42 (m, 3H), 3.71 (t, J=5.0 Hz, 2H), 4.05 (d, J=14.8 Hz, 1H), 4.13 (d, J=14.8 Hz, 1H), 4.22-4.38 (m, 2H), 5.43 (brs, 1H), 7.09-7.14 (m, 3H), 7.29-7.34 (m, 3H), 7.61 (s, 1H).

Reference Example 44

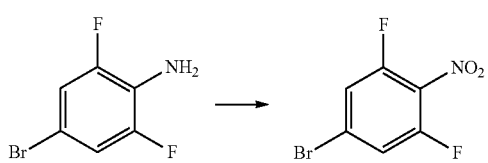 [SMILES: Nc1c(F)cc(Br)cc1F ; O=[N+]([O-])c1c(F)cc(Br)cc1F]

The object product was obtained in the same manner as in Reference Example 40 from 4-bromo-2,6-difluoroaniline.

$^1$H-NMR (CDCl$_3$) δ 7.28-7.32 (m, 2H).

Reference Example 45

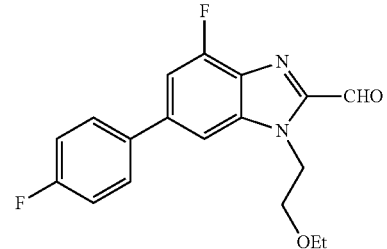

The object product was obtained in the same manner as in Reference Example 41 from the compound obtained in Reference Example 44.

$^1$H-NMR (CDCl$_3$) δ 1.06 (t, J=7.0 Hz, 3H), 3.41 (q, J=7.0 Hz, 2H), 3.81 (t, J=5.3 Hz, 2H), 4.81 (t, J=5.3 Hz, 2H), 7.15-7.19 (m, 2H), 7.27 (dd, J=11.0, 1.6 Hz, 1H), 7.51 (d, J=1.6 Hz, 1H), 7.57-7.61 (m, 2H), 10.16 (s, 1H).

Example 114

N$^2$-{[1-(2-ethoxyethyl)-4-fluoro-6-(4-fluorophenyl)-1H-benzimidazol-2-yl]methyl}-L-alaninamide

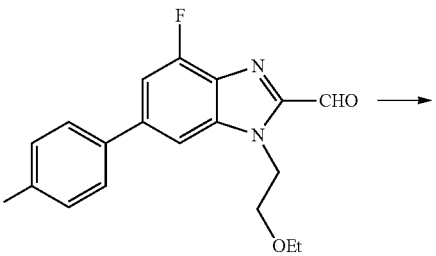

The object product was obtained in the same manner as in Example 2 from the compound obtained in Reference Example 45 and (L)-alaninamide hydrochloride.

$^1$H-NMR (CDCl$_3$) δ 1.11 (t, J=7.0 Hz, 3H), 1.42 (d, J=6.8 Hz, 3H), 3.32-3.45 (m, 3H), 3.77 (t, J=5.0 Hz, 2H), 4.08 (d,

J=14.6 Hz, 1H), 4.18 (d, J=14.6 Hz, 1H), 4.31-4.46 (m, 2H), 6.00 (brs, 1H), 7.12-7.29 (m, 5H), 7.52-7.59 (m, 2H).

Reference Example 46

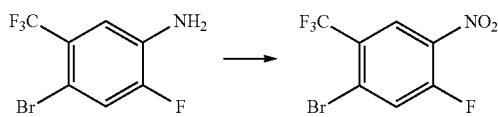

The object product was obtained in the same manner as in Reference Example 40 from 4-bromo-6-fluoro-3-trifluoromethylaniline.

Reference Example 47

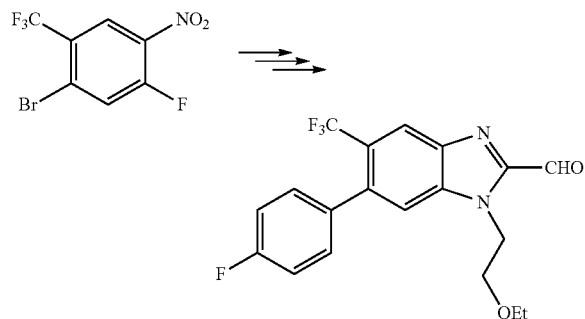

The object product was obtained in the same manner as in Reference Example 41 from the compound obtained in Reference Example 46.
$^1$H-NMR (CDCl$_3$) δ 1.03 (t, J=7.0 Hz, 3H), 3.38 (q, J=7.0 Hz, 2H), 3.77 (t, J=5.1 Hz, 2H), 4.78 (t, J=5.1 Hz, 2H), 7.09-7.13 (m, 2H), 7.31-7.35 (m, 2H), 7.53 (s, 1H), 8.32 (s, 1H), 10.16 (s, 1H).

Example 115

N$^2$-{[1-(2-ethoxyethyl)-6-(4-fluorophenyl)-5-(trifluoromethyl)-1H-benzimidazol-2-yl]methyl}-L-alaninamide

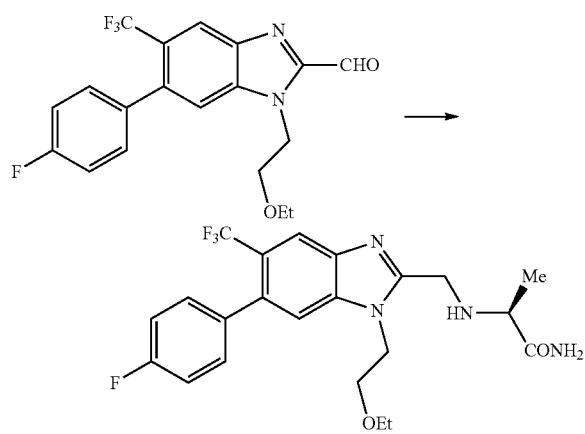

The object product was obtained in the same manner as in Example 2 from the compound obtained in Reference Example 47 and (L)-alaninamide hydrochloride.
$^1$H-NMR (CDCl$_3$) δ 1.09 (t, J=7.0 Hz, 3H), 1.43 (d, J=7.0 Hz, 3H), 3.31-3.42 (m, 3H), 3.71 (t, J=5.0 Hz, 2H), 4.09 (d, J=15.0 Hz, 1H), 4.18 (d, J=15.0 Hz, 1H), 4.27-4.38 (m, 2H), 5.34 (brs, 1H), 7.10 (t, J=8.7 Hz, 2H), 7.13 (brs, 1H), 7.25 (s, 1H), 7.31-7.36 (m, 2H), 8.13 (s, 1H).

Reference Example 48

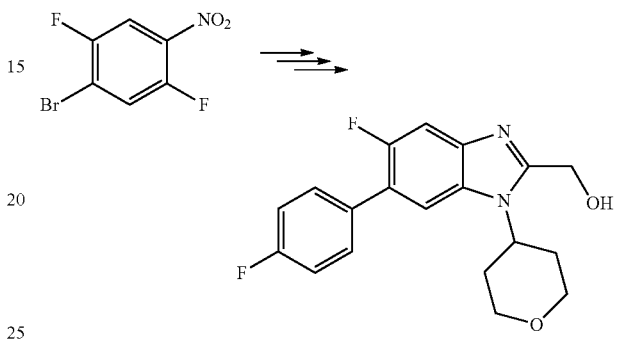

The object product was obtained in the same manner as in Reference Examples 1, 3, 4 and 11 from 2,5-difluoro-4-bromonitrobenzene, 4-aminotetrahydropyran hydrochloride and 4-fluorophenylboronic acid.
$^1$H-NMR (CDCl$_3$) δ 1.94 (m, 2H), 2.58 (m, 2H), 3.62 (m, 2H), 4.20 (m, 2H), 4.69 (m, 1H), 4.92 (s, 2H), 7.12-7.21 (m, 2H), 7.45 (d, 1H, J=10.6 Hz), 7.48-7.57 (m, 3H).

Reference Example 49

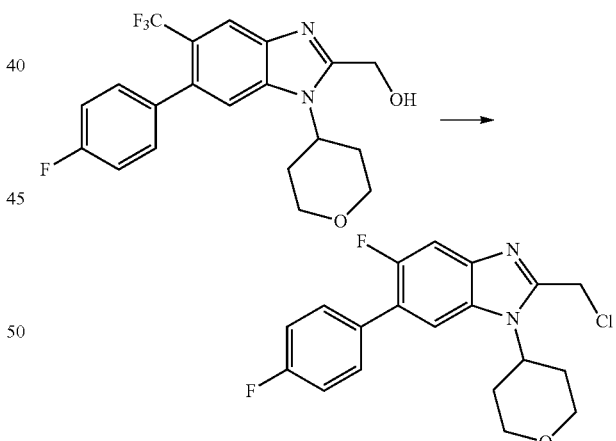

To a solution of the compound (0.82 g, 2.38 mmol) obtained in Reference Example 48 in dichloromethane (20 mL) were added diisopropylethylamine (2.12 ml, 11.9 mmol) and thionyl chloride (1 mol/L dichloromethane solution, 11.9 ml, 11.9 mmol). After heating under reflux for 1 hr, the mixture was cooled to 0° C. and water was added thereto. The mixture was neutralized with 2 mol/L aqueous sodium hydroxide solution, and extracted with chloroform. The organic layer was washed with water and saturated brine, dried over sodium sulfate, concentrated under reduced pressure, and the obtained residue was directly used for the next reaction.

¹H-NMR (CDCl₃) δ 1.96-2.05 (m, 2H), 2.55-2.70 (m, 2H), 3.58-3.66 (m, 2H), 4.19-4.24 (m, 2H), 4.61 (m, 1H), 4.88 (s, 2H), 7.15-7.22 (m, 2H), 7.50-7.57 (m, 4H).

Example 116

N²-{[5-fluoro-6-(4-fluorophenyl)-1-(tetrahydro-2H-pyran-4-yl)-1H-benzimidazol-2-yl]methyl}-L-alaninamide

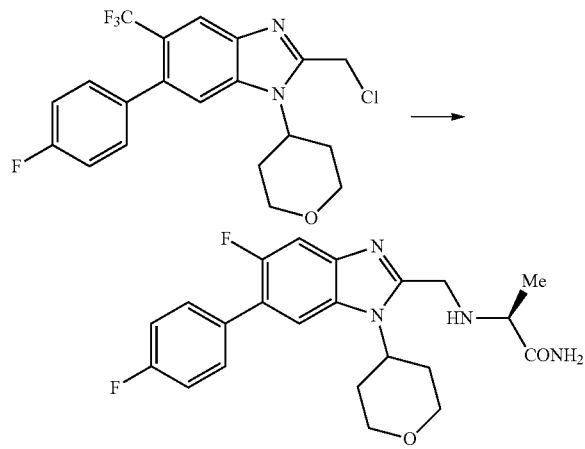

To a solution of the compound (0.16 g, 0.44 mmol) obtained in Reference Example 49 in tetrahydrofuran (5 ml) were added N-(2,4-dimethoxybenzyl)alaninamide (0.12 g, 0.49 mmol), diisopropylethylamine (0.12 ml, 0.66 mmol) and sodium iodide (0.07 g, 0.44 mmol). After heating under reflux for 2 hr, the mixture was allowed to cool to room temperature and water was added thereto. The mixture was extracted with chloroform, and the organic layer was washed with saturated brine, dried over sodium sulfate, and concentrated under reduced pressure. To the residue was added trifluoroacetic acid (2 mL) and the mixture was heated to 50° C. After stirring for 1 hr, the mixture was cooled to 0° C., chloroform was added thereto, and the mixture was neutralized with 2 mol/L aqueous sodium hydroxide solution, and extracted with chloroform. The organic layer was washed with saturated brine, dried over sodium sulfate, and concentrated under reduced pressure. The obtained residue was purified by silica gel column (chloroform:methanol=99:1-85:15) and recrystallized from ethyl acetate-hexane to give the object product (0.09 mg, 50%).

¹H-NMR (CDCl₃) δ 1.40 (d, J=7.0 Hz, 3H), 1.86-1.89 (m, 2H), 2.49-2.64 (m, 2H), 3.32 (m, 1H), 3.53-3.61 (m, 2H), 4.11-4.20 (m, 4H), 4.53 (m, 1H), 5.43 (brs, 1H), 7.08 (brs, 1H), 7.12-7.18 (m, 2H), 7.43-7.52 (m, 4H).

Reference Example 50

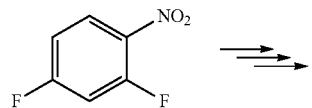

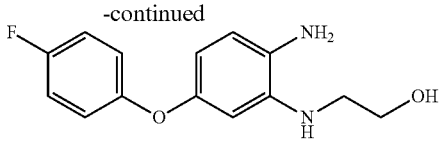

The object product was obtained in the same manner as in Reference Examples 1-3 from 2,4-difluoronitrobenzene, 2-aminoethanol and 4-fluorophenol.

¹H-NMR (CDCl₃) δ 3.23 (t, J=4.8 Hz, 2H), 3.84 (t, J=4.8 Hz, 2H), 6.28 (d, J=7.8 Hz, 1H), 6.37 (d, J=2.4 Hz, 1H), 6.66 (d, J=7.8 Hz, 1H), 6.27-6.98 (m, 4H).

Reference Example 51

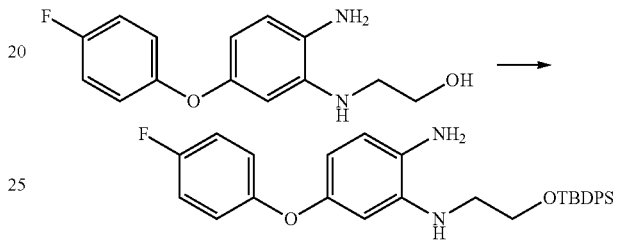

To a solution of the compound (2.7 g, 10.5 mmol) obtained in Reference Example 50 in N,N-dimethylformamide (50 mL) were added t-butyl-diphenylsilyl chloride (3.6 ml, 12.6 mmol) and imidazole (1.1 g, 15.8 mmol), and the mixture was stirred at room temperature. After stirring for 1 hr, water was added thereto, and the mixture was extracted with ethyl acetate. The organic layer was washed with saturated brine, dried over magnesium sulfate, and concentrated under reduced pressure, and the obtained residue was directly used for the next reaction.

¹H-NMR (CDCl₃) δ 1.05 (s, 9H), 3.16 (t, J=5.1 Hz, 2H), 3.87 (t, J=5.1 Hz, 2H), 6.24-6.28 (m, 2H), 6.65 (d, J=8.1 Hz, 1H), 6.82-6.94 (m, 4H), 7.31-7.43 (m, 6H), 7.62-7.72 (m, 4H).

Reference Example 52

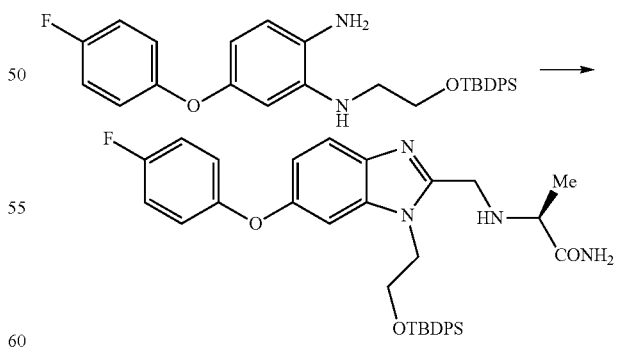

The object product was obtained in the same manner as in Reference Examples 4 and 5 and Example 2 from the compound obtained in Reference Example 51 and (L)-alaninamide hydrochloride.

¹H-NMR (CDCl₃) δ 1.02 (s, 9H), 1.45 (d, J=6.8 Hz, 3H), 3.34 (q, J=6.8 Hz, 1H), 3.95 (t, J=5.4 Hz, 2H), 4.09 (d, J=14.9

Hz, 1H), 4.14 (d, J=14.9 Hz, 1H), 4.23-4.36 (m, 2H), 6.08 (brs, 1H), 6.87-6.93 (m, 3H), 7.00-7.05 (m, 3H), 7.18 (brs, 1H), 7.30-7.36 (m, 4H), 7.41-7.47 (m, 6H), 7.79 (d, J=8.8 Hz, 1H).

Example 117

N$^2$-{[6-(4-fluorophenoxy)-1-(2-hydroxyethyl)-1H-benzimidazol-2-yl]methyl}-L-alaninamide

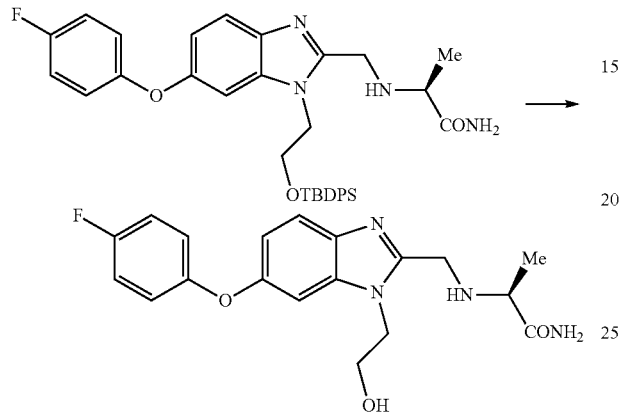

To a solution (4 mL) of the compound (1.2 g, 2.0 mmol) obtained in Reference Example 52 in THF was added tetrabutylammonium fluoride (1 mol/L tetrahydrofuran solution, 3.0 ml, 3.0 mmol), and the mixture was stirred at room temperature. After stirring for 1 hr, water was added thereto, and the mixture was extracted with chloroform. The organic layer was washed with saturated brine, dried over magnesium sulfate, and concentrated under reduced pressure. The obtained residue was purified by silica gel column (chloroform:methanol=99:1-85:15) and recrystallized from chloroform-hexane to give the object product (300 mg, 40%).

$^1$H-NMR (CDCl$_3$) δ 1.32 (d, J=7.0 Hz, 3H), 3.33 (q, J=7.0 Hz, 1H), 3.92-3.98 (m, 2H), 4.03 (d, J=13.6 Hz, 1H), 4.08 (d, J=13.6 Hz, 1H), 4.30 (t, J=4.6 Hz, 2H), 5.50 (brs, 1H), 6.78 (brs, 1H), 6.92-7.03 (m, 6H), 7.64 (d, J=8.8 Hz, 1H).

Reference Example 53

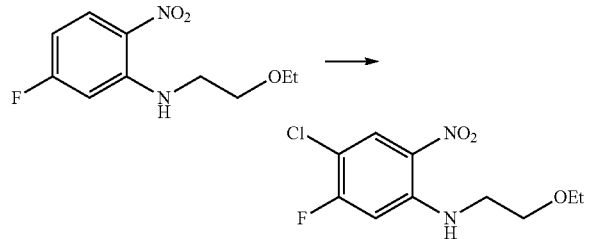

To a solution of the compound (1.0 g, 4.4 mmol) obtained in Reference Example 1 in N,N-dimethylformamide (44 mL) was added N-chlorosuccinimide (0.64 g, 4.8 mmol), and the mixture was heated to 40° C. After stirring overnight, the mixture was allowed to cool to room temperature. Water was added thereto, and the mixture was extracted with ethyl acetate. The organic layer was washed with saturated brine, dried over magnesium sulfate, and concentrated under reduced pressure. The obtained residue was purified by silica gel column (hexane:ethyl acetate=95:5-90:10-75:25-50:50) to give the object product (0.82 g, 72%).

$^1$H-NMR (CDCl$_3$) δ 1.22 (t, J=7.0 Hz, 3H), 3.41 (q, J=5.2 Hz, 2H), 3.55 (q, J=7.0 Hz, 2H), 3.69 (t, J=5.2 Hz, 2H), 6.62 (d, J=11.5 Hz, 1H), 8.27 (d, J=7.8 Hz, 1H), 8.31 (brs, 1H).

Reference Example 54

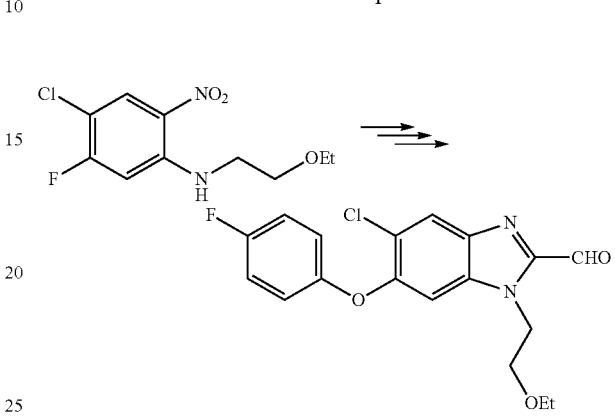

The object product was obtained in the same manner as in Reference Examples 2-5 from the compound obtained in Reference Example 53.

$^1$H-NMR (CDCl$_3$) δ 0.95 (t, J=7.0 Hz, 3H), 3.29 (q, J=7.0 Hz, 2H), 3.67 (t, J=5.0 Hz, 2H), 4.59 (t, J=5.0 Hz, 2H), 6.96-7.10 (m, 5H), 7.98 (s, 1H), 10.02 (s, 1H).

Example 118

N$^2$-{[5-chloro-1-(2-ethoxyethyl)-6-(4-fluorophenoxy)-1H-benzimidazol-2-yl]methyl}-L-alaninamide

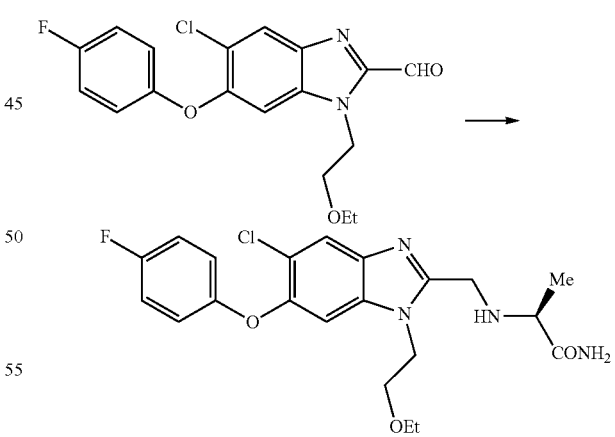

The object product was obtained in the same manner as in Example 2 from the compound obtained in Reference Example 54 and (L)-alaninamide hydrochloride.

$^1$H-NMR (CDCl$_3$) δ 1.05 (t, J=7.0 Hz, 3H), 1.40 (d, J=6.8 Hz, 3H), 3.29-3.38 (m, 3H), 3.63 (t, J=5.0 Hz, 2H), 4.01 (d, J=14.8 Hz, 1H), 4.10 (d, J=14.8 Hz, 1H), 4.15-4.28 (m, 2H), 5.68 (brs, 1H), 6.87-6.91 (m, 2H), 6.97-7.02 (m, 3H), 7.16 (brs, 1H), 7.80 (s, 1H).

Examples 119-190

The compounds of Examples 119-190 shown in Tables 17-31 were prepared according to the methods described in the above-mentioned Reference Examples and Examples or methods analogous thereto.

TABLE 17

| Example | structural formula | $^1$H-NMR(CDCl$_3$) δ |
|---|---|---|
| 119 | | 1.40 (d, J = 7.0 Hz, 3H), 1.55 (m, 1H), 1.80-1.95 (m, 2H), 2.03 (m, 1H), 2.33 (s, 3H), 3.32 (q, J = 7.0 Hz, 1H), 3.70 (m, 1H), 3.80 (m, 1H), 4.01-4.21 (m, 5H), 5.57 (brs, 1H), 6.87-7.01 (m, 4H), 7.12 (d, J = 8.3 Hz, 2H), 7.27 (brs, 1H), 7.65 (d, J = 8.3 Hz, 1H). |
| 120 | | 1.41 (d, J =7.0 Hz, 3H), 1.57 (m, 1H), 1.84-1.95 (m, 2H), 2.05 (m, 1H), 3.32 (q, J = 7.0 Hz, 1H), 3.71 (m, 1H), 3.80 (m, 1H), 4.03-4.25 (m, 5H), 5.61 (brs, 1H), 6.94-7.00 (m, 3H), 7.03 (d, J = 2.4 Hz, 1H), 7.16 (d, J = 8.4 Hz, 2H), 7.23 (brs, 1H), 7.69 (d, J = 8.4 Hz, 1H). |
| 121 | | 1.41 (d, J = 7.0 Hz, 3H), 1.57 (m, 1H), 1.80-2.10 (m, 3H), 3.31 (q, J = 7.0 Hz, 1H), 3.66-3.84 (m, 2H), 4.00-4.24 (m, 5H), 5.40 (br, 1H), 6.78-7.05 (m, 5H), 7.24 (br, 1H), 7.65 (d, J = 8.6 Hz, 1H). |
| 122 | | 1.43 (d, J = 7.0 Hz, 3H), 2.03 (m, 2H), 3.28-3.38 (m, 6H), 4.02 (d, J = 14.7 Hz, 1H), 4.08 (d, J = 14.7 Hz, 1H), 4.21 (t, J = 6.8 Hz, 2H), 5.47 (br, 1H), 6.66-6.84 (m, 2H), 6.96 (dd, J = 8.6, 2.2 Hz, 1H), 7.04 (d, J = 2.2 Hz, 1H), 7.10 (m, 1H), 7.20 (br, 1H), 7.69 (d, J = 8.8 Hz, 1H). |
| 123 | | 1.42 (d, J = 7.0 Hz, 3H), 2.02 (m, 2H), 3.25-3.36 (m, 6H), 4.00 (d, J = 14.7 Hz, 1H), 4.06 (d, J = 14.7 Hz, 1H), 4.19 (t, J = 6.8 Hz, 2H), 5.55 (br, 1H), 6.79-7.06 (m, 5H), 7.21 (br, 1H), 7.64 (d, J = 8.6 Hz, 1H). |

TABLE 18

| Example | structural formula | ¹H-NMR(CDCl₃) δ |
|---|---|---|
| 124 | (structure) | 1.41 (d, J = 6.8 Hz, 3H), 1.55 (m, 1H), 1.75-2.10 (m, 3H), 3.35 (q, J = 6.8 Hz, 1H), 3.66-3.84 (m, 2H), 4.00-4.30 (m, 5H), 5.45 (br, 1H), 6.70 (m, 1H), 6.80 (m, 1H), 6.95 (dd, J = 8.6, 2.2 Hz, 1H), 7.01 (d, J = 2.2 Hz, 1H), 7.09 (m, 1H), 7.21 (br, 1H), 7.68 (d, J = 8.6 Hz, 1H). |
| 125 | (structure) | 1.40 (d, J = 7.0 Hz, 3H), 1.55 (m, 1H), 1.80-2.10 (m, 3H), 3.34 (q, J = 7.0 Hz, 1H), 3.66-3.83 (m, 2H), 3.98-4.28 (m, 5H), 5.44 (br, 1H), 6.79-7.05 (m, 5H), 7.22 (br, 1H), 7.64 (d, J = 8.6 Hz, 1H). |
| 126 | (structure) | 1.42 (d, J = 7.0 Hz, 3H), 2.01 (m, 2H), 2.33 (s, 3H), 3.28 (s, 3H), 3.28 (m, 2H), 3.33 (q, J = 7.0 Hz, 1H), 4.00 (d, J = 14.7 Hz, 1H), 4.07 (d, J = 14.7 Hz, 1H), 4.18 (t, J = 6.8 Hz, 2H), 5.50 (br, 1H), 6.87-7.02 (m, 4H), 7.12 (m, 2H), 7.23 (br, 1H), 7.64 (d, J = 8.6 Hz, 1H). |
| 127 | (structure) | 1.42 (d, J = 6.8 Hz, 3H), 2.03 (m, 2H), 3.28 (s, 3H), 3.28-3.38 (m, 3H), 4.02 (d, J = 14.8 Hz, 1H), 4.08 (d, J = 14.8 Hz, 1H), 4.21 (t, J = 6.9 Hz, 2H), 5.56 (br, 1H), 6.95-7.00 (m, 3H), 7.05 (d, J = 2.2 Hz, 1H), 7.14-7.25 (m, 3H), 7.69 (d, J = 8.8 Hz, 1H). |
| 128 | (structure) | 1.40 (d, J = 7.0 Hz, 3H), 1.80-1.95 (m, 2H), 2.50 (m, 2H), 3.28 (q, J = 7.0 Hz, 1H), 3.56 (m, 2H), 4.00-4.22 (m, 4H), 4.50 (m, 1H), 5.59 (br, 1H), 6.65-6.83 (m, 2H), 6.90 (br, 1H), 6.95 (dd, J = 8.8, 2.2 Hz, 1H), 7.10 (m, 1H), 7.28 (d, J = 2.2 Hz, 1H), 7.69 (d, J = 8.8 Hz, 1H). |

TABLE 19
| Example | structural formula | $^1$H-NMR(CDCl$_3$) δ |
|---|---|---|
| 129 | 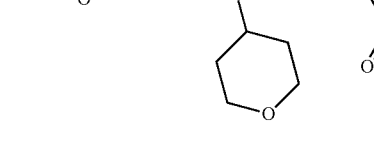 | 1.40 (d, J = 6.9 Hz, 3H), 1.78-1.86 (m, 2H), 2.33 (s, 3H), 2.43-2.58 (m, 2H), 3.28 (q, J = 6.9 Hz, 1H), 3.50-3.59 (m, 2H), 4.00-4.19 (m, 4H), 4.47 (m, 1H), 5.72 (brs, 1H), 6.87-7.00 (m, 4H), 7.10-7.14 (m, 2H), 7.27 (d, J = 2.2 Hz, 1H), 7.65 (d, J = 8.8 Hz, 1H). |
| 130 | 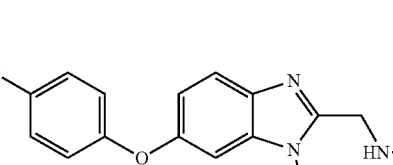 | 1.40 (d, J = 6.9 Hz, 3H), 1.80-1.91 (m, 2H), 2.44-2.59 (m, 2H), 3.29 (q, J = 6.9 Hz, 1H), 3.50-3.60 (m, 2H), 4.01-4.21 (m, 4H), 4.50 (m, 1H), 5.86 (brs, 1H), 6.92-7.00 (m, 4H), 7.14-7.20 (m, 2H), 7.31 (d, J = 2.0 Hz, 1H), 7.69 (d, J = 8.8 Hz, 1H). |
| 131 |  | 1.40 (d, J = 6.9 Hz, 3H), 1.55 (m, 1H), 1.78-1.89 (m, 2H), 2.01 (m, 1H), 2.33 (s, 3H), 3.34 (q, J = 6.9 Hz, 1H), 3.71 (m, 1H), 3.79 (m, 1H), 3.98-4.27 (m, 5H), 5.57 (brs, 1H), 6.86-6.91 (m, 2H), 6.93-7.01 (m, 2H), 7.12 (d, J = 8.3 Hz, 2H), 7.27 (brs, 1H), 7.65 (d, J = 8.3 Hz, 1H). |
| 132 | 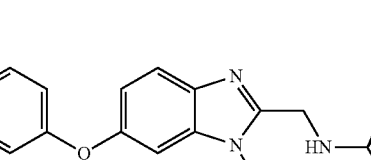 | 1.41 (d, J = 6.9 Hz, 3H), 1.56 (m, 1H), 1.79-1.95 (m, 2H), 2.05 (m, 1H), 3.35 (q, J = 6.9 Hz, 1H), 3.70 (m, 1H), 3.80 (m, 1H), 3.99-4.21 (m, 4H), 4.25 (dd, J = 14.8, 2.8 Hz, 1H), 5.68 (brs, 1H), 6.94-7.00 (m, 3H), 7.03 (d, J = 2.2 Hz, 1H), 7.13-7.19 (m, 2H), 7.22 (brs, 1H), 7.69 (d, J = 8.5 Hz, 1H). |
| 133 | 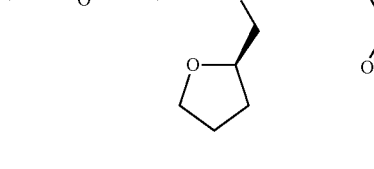 | 1.38 (d, J = 6.8 Hz, 3H), 2.03-2.09 (m, 2H), 3.36-3.55 (m, 3H), 4.06 (d, J = 14.3 Hz, 1H), 4.13 (d, J = 14.3 Hz, 1H), 4.22-4.41 (m, 2H), 5.72 (brs, 1H), 6.95-7.18 (m, 7H), 7.68 (d, J = 8.6 Hz, 1H). |

TABLE 20

| Example | structural formula | ¹H-NMR(CDCl₃) δ |
|---|---|---|
| 134 | (4-trifluoromethoxyphenoxy-benzimidazole with N-(2-hydroxyethyl) and CH(CH₃)C(O)NH₂ side chain) | 1.32 (d, J = 7.0 Hz, 3H), 3.35 (q, J = 7.0 Hz, 1H), 3.96 (t, J = 4.8 Hz, 2H), 4.04 (d, J = 14.0 Hz, 1H), 4.10 (d, J = 14.0 Hz, 1H), 4.32 (t, J = 4.8 Hz, 2H), 5.65 (brs, 1H), 6.85 (brs, 1H), 6.95-7.00 (m, 4H), 7.15-7.18 (m, 2H), 7.65 (d, J = 9.4 Hz, 1H). |
| 135 | (4-methylphenoxy-benzimidazole with N-ethyl and C(Me)₂C(O)NH₂ side chain) | 1.38 (t, J = 7.2 Hz, 3H), 1.47 (s, 6H), 2.34 (s, 3H), 3.97 (s, 2H), 4.10 (q, J = 7.2 Hz, 2H), 5.45 (br, 1H), 6.85-7.00 (m, 4H), 7.13 (m, 2H), 7.32 (br, 1H), 7.65 (d, J = 8.8 Hz, 1H). |
| 136 | (4-fluorophenoxy-benzimidazole with N-cyclopropyl and C(CH₃)₂C(O)NH₂ side chain) | 1.00-1.28 (m, 4H), 1.48 (s, 6H), 3.18 (m, 1H), 4.08 (s, 2H), 5.58 (br, 1H), 6.90-7.05 (m, 5H), 7.15 (d, J = 2.4 Hz, 1H), 7.42 (br, 1H), 7.64 (d, J = 8.8 Hz, 1H). |
| 137 | (2,4-difluorophenoxy-benzimidazole with N-(tetrahydrofuran-2-ylmethyl) and C(CH₃)₂C(O)NH₂ side chain) | 1.46 (s, 6H), 1.57 (m, 1H), 1.80-2.10 (m, 3H), 3.67-3.84 (m, 2H), 3.96-4.25 (m, 5H), 5.33 (br, 1H), 6.82 (m, 1H), 6.89-7.04 (m, 4H), 7.45 (br, 1H), 7.65 (d, J = 8.6 Hz, 1H). |
| 138 | (4-fluorophenoxy-benzimidazole with N-ethyl and C(CH₃)₂C(O)NH₂ side chain) | 1.31 (t, J = 7.3 Hz, 3H), 1.47 (s, 6H), 3.97 (s, 2H), 4.11 (q, J = 7.3 Hz, 2H), 5.59 (br, 1H), 6.92-7.06 (m, 6H), 7.30 (br, 1H), 7.67 (m, 1H). |

TABLE 21

| Example | structural formula | ¹H-NMR(CDCl₃) δ |
|---|---|---|
| 139 | (4-fluorophenoxy-benzimidazole with N-ethyl and CH(Me)C(O)NH₂ side chain) | 1.39 (t, J = 7.1 Hz, 3H), 1.42 (d, J = 6.8 Hz, 3H), 3.32 (q, J = 6.8 Hz, 1H), 3.39 (d, J = 14.8 Hz, 1H), 4.06 (d, J = 14.8 Hz, 1H), 4.12 (m, 2H), 5.50 (br, 1H), 6.92-7.14 (m, 7H), 7.67 (m, 1H). |

TABLE 21-continued

| Example | structural formula | ¹H-NMR(CDCl₃) δ |
|---|---|---|
| 140 | | 1.47 (s, 6H), 1.78-1.86 (m, 2H), 2.33 (s, 3H), 2.44-2.58 (m, 2H), 3.48-3.58 (m, 2H), 4.00 (s, 2H), 4.12-4.20 (m, 2H), 4.41 (m, 1H), 5.65 (brs, 1H), 6.86-6.91 (m, 2H), 6.94 (dd, J = 8.8, 2.2 Hz, 1H), 7.10-7.14 (m, 2H), 7.17 (brs, 1H), 7.26 (d, J = 2.2 Hz, 1H), 7.65 (d, J = 8.8 Hz, 1H). |
| 141 | | 1.09 (t, J = 7.0 Hz, 3H), 1.47 (s, 6H), 3.39 (q, J =7.0 Hz, 2H), 3.70 (t, J = 5.0 Hz, 2H), 4.03 (s, 2H), 4.26 (t, J = 5.0 Hz, 2H), 5.41 (br, 1H), 6.70 (m, 1H), 6.80 (m, 1H), 6.94-7.15 (m, 3H), 7.46 (br, 1H), 7.70 (d, J = 8.4 Hz, 1H). |
| 142 | | 1.47 (s, 6H), 2.02 (m, 2H), 2.33 (s, 3H), 3.28 (s, 3H), 3.28 (m, 2H), 3.98 (s, 2H), 4.18 (t, J = 6.9 Hz, 2H), 5.48 (br, 1H), 6.87-7.02 (m, 4H), 7.10 (d, J = 8.2 Hz, 2H), 7.44 (br, 1H), 7.65 (d, J = 8.6 Hz, 1H). |
| 143 | | 1.45 (s, 6H), 3.96 (t, J = 4.8 Hz, 2H), 4.01 (s, 2H), 4.30 (t, J = 4.8 Hz, 2H), 5.39 (brs, 1H), 6.92-7.05 (m, 7H), 7.65 (d, J = 8.6 Hz, 1H). |

TABLE 22

| Example | structural formula | ¹H-NMR(CDCl₃) δ |
|---|---|---|
| 144 | | 1.10 (t, J = 7.0 Hz, 3H), 1.41 (d, J = 6.8 Hz, 3H), 2.38 (s, 3H), 3.33-3.43 (m, 3H), 3.74 (t, J = 5.1 Hz, 2H), 4.05 (d, J = 14.8 Hz, 1H), 4.15 (d, J = 14.8 Hz, 1H), 4.31-4.43 (m, 2H), 5.89 (brs, 1H), 7.26-7.32 (m, 4H), 7.48-7.55 (m, 3H), 7.76 (d, J = 8.3 Hz, 1H). |

TABLE 22-continued

| Example | structural formula | ¹H-NMR(CDCl₃) δ |
|---|---|---|
| 145 | (structure: 6-(4-trifluoromethoxyphenyl)benzimidazole with N-CH₂CH₂OCH₂CH₃ and 2-CH₂-NH-CH(Me)-C(O)NH₂) | 1.10 (t, J = 7.0 Hz, 3H), 1.41 (d, J = 7.0 Hz, 3H), 3.32-3.42 (m, 3H), 3.76 (t, J = 5.1 Hz, 2H), 4.07 (d, J = 14.8 Hz, 1H), 4.15 (d, J = 14.8 Hz, 1H), 4.30-4.41 (m, 2H), 5.75 (brs, 1H), 7.25-7.32 (m, 3H), 7.45-7.47 (m, 2H), 7.63-7.65 (m, 2H), 7.78 (d, J = 9.0 Hz, 1H). |
| 146 | (structure: 6-(4-trifluoromethylphenyl)benzimidazole with N-CH₂CH₂OCH₂CH₃ and 2-CH₂-NH-CH(Me)-C(O)NH₂) | 1.10 (t, J = 7.0 Hz, 3H), 1.41 (d, J = 6.8 Hz, 3H), 3.32-3.42 (m, 3H), 3.76 (t, J = 5.0 Hz, 2H), 4.07 (d, J = 14.6 Hz, 1H), 4.16 (d, J = 14.6 Hz, 1H), 4.31-4.43 (m, 2H), 5.70 (brs, 1H), 7.25 (brs, 1H), 7.49-7.52 (m, 2H), 7.68-7.74 (m, 4H), 7.80 (d, J = 8.3 Hz, 1H). |
| 147 | (structure: 6-(2,4-difluorophenyl)benzimidazole with N-CH₂CH₂OEt and 2-CH₂-NH-CH(Me)-C(O)NH₂) | 1.10 (t, J = 7.0 Hz, 3H), 1.41 (d, J = 7.0 Hz, 3H), 3.31-3.43 (m, 3H), 3.75 (t, J = 5.0 Hz, 2H), 4.08 (d, J = 14.7 Hz, 1H), 4.17 (d, J = 14.7 Hz, 1H), 4.30-4.43 (m, 2H), 5.73 (brs, 1H), 6.90-7.00 (m, 2H), 7.28-7.50 (m, 4H), 7.79 (d, J = 8.4 Hz, 1H). |
| 148 | (structure: 6-(3,4-difluorophenyl)benzimidazole with N-CH₂CH₂OCH₂CH₃ and 2-CH₂-NH-CH(CH₃)-C(O)NH₂) | 1.10 (t, J = 7.0 Hz, 3H), 1.41 (d, J = 7.0 Hz, 3H), 3.34-3.43 (m, 3H), 3.76 (t, J = 5.0 Hz, 2H), 4.08 (d, J = 14.8 Hz, 1H), 4.15 (d, J = 14.8 Hz, 1H), 4.29-4.43 (m, 2H), 5.98 (brs, 1H), 7.18-7.44 (m, 6H), 7.77 (d, J = 8.4 Hz, 1H). |

TABLE 23

| Example | structural formula | ¹H-NMR(CDCl₃) δ |
|---|---|---|
| 149 | (structure: 6-(4-fluorophenyl)benzimidazole with N-CH₂CH₂OCH₂CH₃ and 2-CH₂-NH-C(CH₃)₂-C(O)NH₂) | 1.11 (t, J = 7.0 Hz, 3H), 1.47 (s, 6H), 3.40 (q, J = 7.0 Hz, 2H), 3.77 (t, J = 5.0 Hz, 2H), 4.06 (s, 2H), 4.36 (t, J = 5.0 Hz, 2H), 5.47 (brs, 1H), 7.12-7.17 (m, 2H), 7.44-7.46 (m, 2H), 7.51 (brs, 1H), 7.57-7.60 (m, 2H), 7.78 (m, 1H). |

TABLE 23-continued

| Example | structural formula | $^1$H-NMR(CDCl$_3$) δ |
|---|---|---|
| 150 | | 1.01 (t, J = 7.4 Hz, 3H), 1.10 (t, J = 7.0 Hz, 3H), 1.69-1.87 (m, 2H), 3.16 (t, J = 6.3 Hz, 1H), 3.39 (q, J = 7.0 Hz, 2H), 3.76 (t, J = 5.0 Hz, 2H), 4.04 (d, J = 14.6 Hz, 1H), 4.16 (d, J = 14.6 Hz, 1H), 4.30-4.45 (m, 2H), 5.96 (brs, 1H), 7.11-7.16 (m, 2H), 7.21 (brs, 1H), 7.43-7.46 (m, 2H), 7.56-7.60 (m, 2H), 7.77 (m, 1H). |
| 151 | | 1.00 (d, J = 7.0 Hz, 3H), 1.02 (d, J = 7.0 Hz, 3H), 1.10 (t, J = 7.0 Hz, 3H), 2.08 (m, 1H), 2.98 (d, J = 5.6 Hz, 1H), 3.40 (q, J = 7.0 Hz, 2H), 3.76 (q, J = 5.2 Hz, 2H), 4.02 (d, J = 14.4 Hz, 1H), 4.18 (d, J = 14.4 Hz, 1H), 4.31-4.49 (m, 2H), 5.66 (brs, 1H), 7.09 (brs, 1H), 7.12-7.17 (m, 2H), 7.44-7.46 (m, 2H), 7.57-7.60 (m, 2H), 7.76 (m, 1H). |
| 152 | | 1.10 (t, J = 7.0 Hz, 3H), 1.41 (d, J = 6.8 Hz, 3H), 2.45 (s, 3H), 3.32-3.42 (m, 3H), 3.76 (t, J = 5.1 Hz, 2H), 4.06 (d, J = 14.8 Hz, 1H), 4.15 (d, J = 14.8 Hz, 1H), 4.30-4.42 (m, 2H), 5.68 (brs, 1H), 7.16-7.52 (m, 7H), 7.77 (m, 1H). |
| 153 | | 1.10 (t, J = 7.0 Hz, 3H), 1.42 (d, J = 7.0 Hz, 3H), 2.29 (s, 3H), 3.33-3.42 (m, 3H), 3.73 (t, J = 5.1 Hz, 2H), 4.08 (d, J = 14.8 Hz, 1H), 4.16 (d, J = 14.8 Hz, 1H), 4.26-4.38 (m, 2H), 5.66 (brs, 1H), 7.22-7.30 (m, 7H), 7.75 (m, 1H). |

TABLE 24

| Example | structural formula | $^1$H-NMR(CDCl$_3$) δ |
|---|---|---|
| 154 | 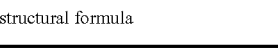 | 1.45 (t, J = 7.0 Hz, 3H), 1.48 (s, 6H), 4.01 (s, 2H), 4.22 (q, J = 7.0 Hz, 2H), 5.82 (brs, 1H), 7.11-7.17 (m, 2H), 7.34 (brs, 1H), 7.42-7.45 (m, 2H), 7.56-7.61 (m, 2H), 7.77 (m, 1H) |

TABLE 24-continued

| Example | structural formula | $^1$H-NMR(CDCl$_3$) δ |
|---|---|---|
| 155 | | 1.10 (t, J = 7.0 Hz, 3H), 1.42 (d, J = 6.8 Hz, 3H), 3.32-3.42 (m, 3H), 3.74 (t, J = 5.1 Hz, 2H), 4.08 (d, J = 14.6 Hz, 1H), 4.16 (d, J = 14.6 Hz, 1H), 4.29-4.41 (m, 2H), 5.41 (brs, 1H), 7.06 (m, 1H), 7.24-7.30 (m, 3H), 7.35-7.39 (m, 2H), 7.77 (d, J = 8.3 Hz, 1H). |
| 156 | | 1.10 (t, J = 7.0 Hz, 3H), 1.47 (s, 6H), 3.40 (q, J = 7.0 Hz, 2H), 3.75 (t, J = 5.1 Hz, 2H), 4.07 (s, 2H), 4.34 (t, J = 5.1 Hz, 2H), 5.37 (brs, 1H), 7.06 (m, 1H), 7.24-7.39 (m, 5H), 7.77 (d, J = 8.3 Hz, 1H). |
| 157 | | 1.10 (t, J = 7.0 Hz, 3H), 1.42 (d, J = 7.0 Hz, 3H), 2.27 (s, 3H), 3.33-3.42 (m, 3H), 3.73 (t, J = 5.4 Hz, 2H), 4.08 (d, J = 15.4 Hz, 1H), 4.15 (d, J = 15.4 Hz, 1H), 4.27-4.40 (m, 2H), 5.35 (brs, 1H), 6.92-7.01 (m, 2H), 7.17-7.25 (m, 3H), 7.29 (brs, 1H), 7.34 (d, J = 8.3 Hz, 1H). |
| 158 | | 1.11 (t, J = 7.0 Hz, 3H), 1.47 (s, 6H), 2.26 (s, 3H), 3.40 (q, J = 7.0 Hz, 2H), 3.74 (t, J = 5.0 Hz, 2H), 4.07 (s, 2H), 4.33 (t, J = 5.0 Hz, 2H), 5.47 (brs, 1H), 6.92-7.01 (m, 2H), 7.17-7.27 (m, 3H), 7.54 (brs, 1H), 7.75 (d, J = 8.3 Hz, 1H). |

TABLE 25

| Example | structural formula | $^1$H-NMR(CDCl$_3$) δ |
|---|---|---|
| 159 | 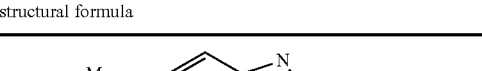 | 1.10 (t, J = 7.0 Hz, 3H), 1.41 (d, J = 7.0 Hz, 3H), 2.26 (s, 3H), 2.38 (s, 3H), 3.32-3.42 (m, 3H), 3.72 (t, J = 5.1 Hz, 2H), 4.07 (d, J = 14.6 Hz, 1H), 4.15 (d, J = 14.6 Hz, 1H), 4.26-4.38 (m, 2H), 5.81 (brs, 1H), 7.07-7.27 (m, 5H), 7.33 (brs, 1H), 7.73 (d, J = 8.3 Hz, 1H). |

TABLE 25-continued

| Example | structural formula | $^1$H-NMR(CDCl$_3$) δ |
|---|---|---|
| 160 | 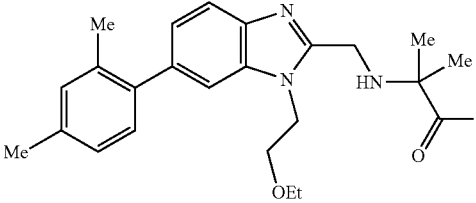 | 1.10 (t, J = 7.0 Hz, 3H), 1.47 (s, 6H), 2.26 (s, 3H), 2.38 (s, 3H), 3.39 (q, J = 7.0 Hz, 2H), 3.73 (t, J = 5.1 Hz, 2H), 4.06 (s, 2H), 4.32 (t, J = 5.1 Hz, 2H), 5.49 (brs, 1H), 7.06-7.26 (m, 5H), 7.55 (brs, 1H), 7.75 (d, J = 8.3 Hz, 1H). |
| 161 | 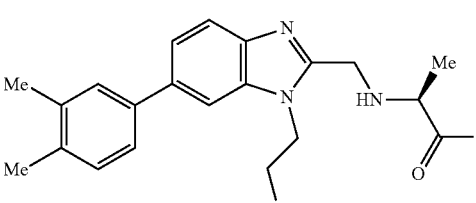 | 1.11 (t, J = 7.0 Hz, 3H), 1.42 (d, J = 6.8 Hz, 3H), 2.32 (s, 3H), 2.36 (s, 3H), 3.31-3.43 (m, 3H), 3.76 (t, J = 5.0 Hz, 2H), 4.07 (d, J = 14.9 Hz, 1H), 4.16 (d, J = 14.9 Hz, 1H), 4.29-4.44 (m, 2H), 5.36 (brs, 1H), 7.23 (m, 1H), 7.36 (brs, 1H), 7.30-7.51 (m, 4H), 7.76 (d, J = 9.0 Hz, 1H). |
| 162 | 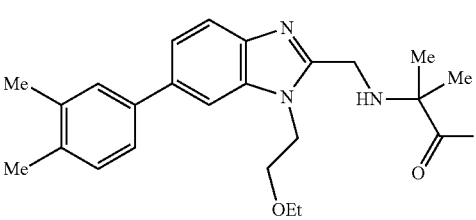 | 1.10 (t, J = 7.0 Hz, 3H), 1.47 (s, 6H), 2.32 (s, 3H), 2.36 (s, 3H), 3.39 (q, J = 7.0 Hz, 2H), 3.77 (t, J = 5.0 Hz, 2H), 4.06 (s, 2H), 4.36 (t, J = 5.0 Hz, 2H), 5.28 (brs, 1H), 7.22 (m, 1H), 7.37-7.51 (m, 4H), 7.55 (brs, 1H), 7.77 (d, J = 8.6 Hz, 1H). |
| 163 | 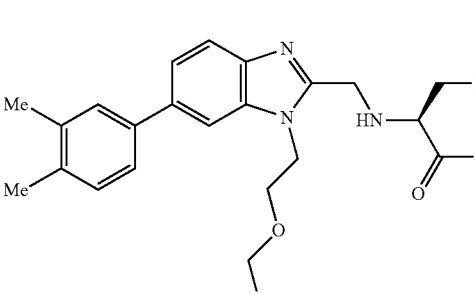 | 1.01 (t, J = 7.5 Hz, 3H), 1.10 (t, J = 7.0 Hz, 3H), 1.65-1.85 (m, 2H), 2.32 (s, 3H), 2.36 (s, 3H), 3.16 (t, J = 6.3 Hz, 1H), 3.39 (q, J = 7.0 Hz, 2H), 3.76 (t, J = 5.2 Hz, 2H), 4.05 (d, J = 14.7 Hz, 1H), 4.16 (d, J = 14.7 Hz, 1H), 4.29-4.46 (m, 2H), 5.42 (brs, 1H), 7.22 (m, 2H), 7.36-7.52 (m, 4H), 7.76 (d, J = 9.0 Hz, 1H). |

TABLE 26

| Example | structural formula | $^1$H-NMR(CDCl$_3$) δ |
|---|---|---|
| 164 | 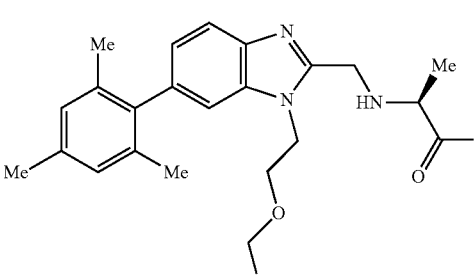 | 1.09 (t, J = 7.0 Hz, 3H), 1.43 (d, J = 7.1 Hz, 3H), 2.01 (s, 6H), 2.35 (s, 3H), 3.33-3.41 (m, 3H), 3.76 (t, J = 5.0 Hz, 2H), 4.07 (d, J = 14.8 Hz, 1H), 4.14 (d, J = 14.8 Hz, 1H), 4.24-4.36 (m, 2H), 5.37 (brs, 1H), 6.97 (s, 2H), 7.04 (dd, J = 8.0, 1.6 Hz, 1H), 7.10 (d, J = 1.6 Hz, 1H), 7.32 (brs, 1H), 7.76 (d, J = 8.0 Hz, 1H). |

TABLE 26-continued

| Example | structural formula | $^1$H-NMR(CDCl$_3$) δ |
|---|---|---|
| 165 | | 1.10 (t, J = 7.0 Hz, 3H), 1.42 (d, J = 7.0 Hz, 3H), 2.41 (s, 3H), 3.31-3.43 (m, 3H), 3.75 (t, J = 5.1 Hz, 2H), 4.07 (d, J = 14.7 Hz, 1H), 4.16 (d, J = 14.7 Hz, 1H), 4.28-4.42 (m, 2H), 5.33 (brs, 1H), 6.98-7.06 (m, 2H), 7.27 (brs, 1H), 7.35-7.49 (m, 3H), 7.78 (d, J = 8.4 Hz, 1H). |
| 166 | | 1.10 (t, J = 7.0 Hz, 3H), 1.47 (s, 6H), 2.41 (s, 3H), 3.39 (q, J = 7.0 Hz, 2H), 3.76 (t, J = 5.1 Hz, 2H), 4.07 (s, 2H), 4.35 (t, J = 5.1 Hz, 2H), 5.31 (brs, 1H), 6.96-7.05 (m, 2H), 7.35-7.49 (m, 2H), 7.52 (brs, 1H), 7.78 (d, J = 8.4 Hz, 1H). |
| 167 | | 1.11 (t, J = 7.0 Hz, 3H), 1.42 (d, J = 7.0 Hz, 3H), 2.36 (s, 3H), 3.31-3.44 (m, 3H), 3.76 (t, J = 5.2 Hz, 2H), 4.07 (d, J = 14.8 Hz, 1H), 4.16 (d, J = 14.8 Hz, 1H), 4.28-4.44 (m, 2H), 5.37 (brs, 1H), 7.08 (t, J = 8.9 Hz, 1H), 7.37-7.46 (m, 5H), 7.77 (d, J = 9.0 Hz, 1H). |
| 168 | | 1.11 (t, J = 7.0 Hz, 3H), 1.47 (s, 6H), 2.36 (s, 3H), 3.40 (q, J = 7.0 Hz, 2H), 3.77 (t, J = 5.0 Hz, 2H), 4.06 (s, 2H), 4.36 (t, J = 5.0 Hz, 2H), 5.30 (brs, 1H), 7.08 (t, J = 8.8 Hz, 1H), 7.36-7.46 (m, 4H), 7.51 (brs, 1H), 7.77 (d, J = 8.1 Hz, 1H). |

TABLE 27

| Example | structural formula | $^1$H-NMR(CDCl$_3$) δ |
|---|---|---|
| 169 | | 1.11 (t, J = 7.0 Hz, 3H), 1.42 (d, J = 7.0 Hz, 3H), 2.33 (s, 3H), 3.31-3.44 (m, 3H), 3.76 (t, J = 5.0 Hz, 2H), 4.07 (d, J = 14.8 Hz, 1H), 4.16 (d, J = 14.8 Hz, 1H), 4.29-4.44 (m, 2H), 5.42 (brs, 1H), 7.23-7.33 (m, 4H), 7.42-7.49 (m, 2H), 7.77 (d, J = 8.8 Hz, 1H). |

TABLE 27-continued

| Example | structural formula | $^1$H-NMR(CDCl$_3$) δ |
|---|---|---|
| 170 | | 1.11 (t, J = 7.0 Hz, 3H), 1.47 (s, 6H), 2.33 (s, 3H), 3.40 (q, J = 7.0 Hz, 2H), 3.77 (t, J = 5.0 Hz, 2H), 4.07 (s, 2H), 4.36 (t, J = 5.0 Hz, 2H), 5.35 (brs, 1H), 7.22-7.33 (m, 4H), 7.46-7.49 (m, 2H), 7.78 (d, J = 9.0 Hz, 1H). |
| 171 | | 1.09 (t, J = 7.0 Hz, 3H), 1.42 (d, J = 6.8 Hz, 3H), 3.34-3.42 (m, 3H), 3.75 (t, J = 5.1 Hz, 2H), 4.09 (d, J = 14.8 Hz, 1H), 4.16 (d, J = 14.8 Hz, 1H), 4.29-4.41 (m, 2H), 5.67 (brs, 1H), 7.14-7.16 (m, 2H), 7.23-7.30 (m, 2H), 7.41-7.52 (m, 2H), 7.80 (d, J = 8.5 Hz, 1H). |
| 172 | | 1.10 (t, J = 7.0 Hz, 3H), 1.41 (d, J = 7.0 Hz, 3H), 3.31-3.42 (m, 3H), 3.74 (t, J = 5.1 Hz, 2H), 3.81 (s, 3H), 4.07 (d, J = 14.8 Hz, 1H), 4.15 (d, J = 14.8 Hz, 1H), 4.28-4.40 (m, 2H), 5.37 (brs, 1H), 6.73-6.78 (m, 2H), 7.28-7.41 (m, 4H), 7.75 (d, J = 8.3 Hz, 1H). |
| 173 | | 1.11 (t, J = 7.0 Hz, 3H), 1.42 (d, J = 7.0 Hz, 3H), 3.32-3.43 (m, 3H), 3.76 (t, J = 5.0 Hz, 2H), 3.98 (s, 3H), 4.08 (d, J = 14.8 Hz, 1H), 4.16 (d, J = 14.8 Hz, 1H), 4.31-4.43 (m, 2H), 5.40 (brs, 1H), 7.13-7.20 (m, 4H), 7.44-7.46 (m, 2H), 7.78 (d, J = 9.0 Hz, 1H). |

TABLE 28

| Example | structural formula | $^1$H-NMR(CDCl$_3$) δ |
|---|---|---|
| 174 | | 1.11 (t, J = 7.0 Hz, 3H), 1.47 (s, 6H), 3.39 (q, J = 7.0 Hz, 2H), 3.75 (t, J = 5.1 Hz, 2H), 3.81 (s, 3H), 4.06 (s, 2H), 4.33 (t, J = 5.1 Hz, 2H), 5.36 (brs, 1H), 6.72-6.78 (m, 2H), 7.28-7.40 (m, 3H), 7.53 (brs, 1H), 7.75 (d, J = 8.3 Hz, 1H). |

TABLE 28-continued

| Example | structural formula | $^1$H-NMR(CDCl$_3$) δ |
|---|---|---|
| 175 | (structure: 6-(4-fluoro-3-methoxyphenyl)-1-(2-ethoxyethyl)benzimidazole with 2-CH$_2$NH-C(Me)$_2$-C(O)NH$_2$) | 1.11 (t, J = 7.0 Hz, 3H), 1.48 (s, 6H), 3.39 (q, J = 7.0 Hz, 2H), 3.77 (t, J = 5.1 Hz, 2H), 3.98 (s, 3H), 4.07 (s, 2H), 4.37 (t, J = 5.1 Hz, 2H), 5.29 (brs, 1H), 7.14-7.20 (m, 4H), 7.44-7.51 (m, 2H), 7.78 (d, J = 8.0 Hz, 1H). |
| 176 | (structure: 5-chloro-6-(4-fluorophenyl)-1-(2-ethoxyethyl)benzimidazole with 2-CH$_2$NH-CH(Me)-C(O)NH$_2$) | 1.09 (t, J = 7.0 Hz, 3H), 1.41 (t, J = 7.0 Hz, 3H), 3.32-3.42 (m, 3H), 3.71 (t, J = 5.1 Hz, 2H), 4.05 (d, J = 14.6 Hz, 1H), 4.14 (d, J = 14.6 Hz, 1H), 4.23-4.38 (m, 2H) 5.39 (brs, 1H), 7.11-7.17 (m, 3H), 7.21 (brs, 1H) 7.41-7.45 (m, 2H), 7.83 (s, 1H). |
| 177 | (structure: 5-chloro-6-phenyl-1-(2-ethoxyethyl)benzimidazole with 2-CH$_2$NH-CH(Me)-C(O)NH$_2$) | 1.10 (t, J = 7.0 Hz, 3H), 1.42 (d, J = 7.0 Hz, 3H), 3.31-3.43 (m, 3H), 3.71 (t, J = 5.0 Hz, 2H), 4.07 (d, J = 14.8 Hz, 1H), 4.17 (d, J = 14.8 Hz, 1H), 4.24-4.39 (m, 2H) 5.60 (brs, 1H), 7.24-7.47 (m, 7H), 7.84 (s, 1H). |
| 178 | (structure: 5-chloro-6-(4-methylphenyl)-1-(2-ethoxyethyl)benzimidazole with 2-CH$_2$NH-CH(Me)-C(O)NH$_2$) | 1.10 (t, J = 7.0 Hz, 3H), 1.43 (d, J = 7.0 Hz, 3H), 2.44 (s, 3H), 3.32-3.42 (m, 3H), 3.71 (t, J = 5.0 Hz, 2H), 4.07 (d, J = 14.8 Hz, 1H), 4.15 (d, J = 14.8 Hz, 1H), 4.25-4.38 (m, 2H) 5.61 (brs, 1H), 7.26-7.39 (m, 6H), 7.83 (s, 1H). |

TABLE 29

| Example | structural formula | $^1$H-NMR(CDCl$_3$) δ |
|---|---|---|
| 179 | (structure: 5-chloro-6-(2,4-difluorophenyl)-1-(2-ethoxyethyl)benzimidazole with 2-CH$_2$NH-CH(Me)-C(O)NH$_2$) | 1.08 (t, J = 7.0 Hz, 3H), 1.41 (d, J = 7.0 Hz, 3H), 3.30-3.41 (m, 3H), 3.70 (t, J = 5.0 Hz, 2H), 4.05 (d, J = 15.1 Hz, 1H), 4.13 (d, J = 15.1 Hz, 1H), 4.24-4.36 (m, 2H) 5.67 (brs, 1H), 6.90-6.98 (m, 2H), 7.21 (brs, 1H), 7.28-7.34 (m, 2H), 7.84 (s, 1H). |

TABLE 29-continued

| Example structural formula | $^1$H-NMR(CDCl$_3$) δ |
|---|---|
| 180 | 1.09 (t, J = 7.0 Hz, 3H), 1.41 (d, J = 7.0 Hz, 3H), 3.30-3.41 (m, 3H), 3.71 (t, J = 5.0 Hz, 2H), 4.05 (d, J = 14.8 Hz, 1H), 4.13 (d, J = 14.8 Hz, 1H), 4.25-4.37 (m, 2H), 5.68 (brs, 1H), 7.15-7.30 (m, 5H), 7.81 (s, 1H). |
| 181 | 1.09 (t, J = 7.0 Hz, 3H), 1.41 (d, J = 7.0 Hz, 3H), 3.30-3.42 (m, 3H), 3.70 (t, J = 5.0 Hz, 2H), 4.05 (d, J = 15.0 Hz, 1H), 4.14 (d, J = 15.0 Hz, 1H), 4.23-4.38 (m, 2H), 5.63 (brs, 1H), 7.20 (brs, 1H), 7.26-7.30 (m, 3H), 7.47-7.50 (m, 2H), 7.83 (s, 1H). |
| 182 | 1.10 (t, J = 7.0 Hz, 3H), 1.42 (d, J = 7.0 Hz, 3H), 3.37-3.44 (m, 3H), 3.72 (t, J = 5.0 Hz, 2H), 4.05 (d, J = 14.8 Hz, 1H), 4.14 (d, J = 14.8 Hz, 1H), 4.25-4.35 (m, 2H), 7.31 (m, 1H), 7.56-7.59 (m, 2H), 7.70-7.73 (m, 2H), 7.84 (s, 1H). |
| 183 | 1.10 (t, J = 7.0 Hz, 3H), 1.42 (d, J = 7.0 Hz, 3H), 3.31-3.43 (m, 3H), 3.74 (t, J = 5.0 Hz, 2H), 4.05 (d, J = 14.8 Hz, 1H), 4.14 (d, J = 14.8 Hz, 1H), 4.28-4.40 (m, 2H), 5.54 (brs, 1H), 7.18 (brs, 1H), 7.21-7.29 (m, 3H), 7.39 (m, 1H), 7.49 (s, 1H). |

TABLE 30

| Example structural formula | $^1$H-NMR(CDCl$_3$) δ |
|---|---|
| 184 | 1.10 (t, J = 7.0 Hz, 3H), 1.42 (d, J = 7.0 Hz, 3H), 2.42 (s, 3H), 3.31-3.42 (m, 3H), 3.73 (t, J = 5.0 Hz, 2H), 4.05 (d, J = 14.8 Hz, 1H), 4.13 (d, J = 14.8 Hz, 1H), 4.26-4.38 (m, 2H), 5.56 (brs, 1H), 7.24 (brs, 1H), 7.26-7.30 (m, 3H), 7.46-7.50 (s, 3H). |

TABLE 30-continued

| Example | structural formula | $^1$H-NMR(CDCl$_3$) δ |
|---|---|---|
| 185 | (benzimidazole structure with F, phenyl, N-CH2CH2OEt, CH2-NH-CH(Me)-C(O)NH2) | 1.10 (t, J = 7.0 Hz, 3H), 1.42 (d, J = 7.0 Hz, 3H), 3.31-3.42 (m, 3H), 3.73 (t, J = 5.0 Hz, 2H), 4.05 (d, J = 14.8 Hz, 1H), 4.13 (d, J = 14.8 Hz, 1H), 4.27-4.39 (m, 2H), 5.58 (brs, 1H), 7.23 (brs, 1H), 7.32 (d, J = 6.3 Hz, 1H), 7.39 (m, 1H), 7.45-7.51 (m, 3H), 7.57-7.59 (s, 2H). |
| 186 | (benzimidazole structure with F, 4-Cl-phenyl, N-CH2CH2OEt, CH2-NH-CH(Me)-C(O)NH2) | 1.10 (t, J = 7.0 Hz, 3H), 1.42 (d, J = 6.8 Hz, 3H), 3.31-3.42 (m, 3H), 3.73 (t, J = 5.0 Hz, 2H), 4.05 (d, J = 14.8 Hz, 1H), 4.13 (d, J = 14.8 Hz, 1H), 4.27-4.39 (m, 2H), 5.36 (brs, 1H), 7.20 (brs, 1H), 7.29 (d, J = 6.6 Hz, 1H), 7.42-7.44 (m, 3H), 7.48-7.52 (m, 2H). |
| 187 | (benzimidazole structure with F, 4-F-phenyl, N-Et, CH2-NH-C(Me)2-C(O)NH2) | 1.45 (t, J = 7.0 Hz, 3H), 1.48 (s, 3H), 3.99 (s, 2H), 4.20 (q, J = 7.0 Hz, 2H), 5.50 (brs, 1H), 7.13-7.18 (m, 2H), 7.28 (d, J = 6.6 Hz, 1H), 7.49 (d, J = 11.0 Hz, 1H), 7.52-7.56 (m, 2H). |
| 188 | (benzimidazole structure with F, 3-Me-4-F-phenyl, N-CH2CH2OEt, CH2-NH-CH(Me)-C(O)NH2) | 1.11 (t, J = 7.0 Hz, 3H), 1.42 (d, J = 7.0 Hz, 3H), 2.35 (s, 3H), 3.30-3.43 (m, 3H), 3.73 (t, J = 5.0 Hz, 2H), 4.05 (d, J = 14.8 Hz, 1H), 4.14 (d, J = 14.8 Hz, 1H), 4.27-4.39 (m, 2H), 5.35 (brs, 1H), 7.09 (t, J = 8.8 Hz, 1H), 7.23 (brs, 1H), 7.34-7.39 (m, 3H), 7.48 (d, J = 10.8 Hz, 1H). |

TABLE 31

| Example | structural formula | $^1$H-NMR(CDCl$_3$) δ |
|---|---|---|
| 189 | (benzimidazole structure with F, 3-F-4-Me-phenyl, N-CH2CH2OEt, CH2-NH-CH(Me)-C(O)NH2) | 1.10 (t, J = 7.0 Hz, 3H), 1.42 (d, J = 6.8 Hz, 3H), 2.34 (s, 3H), 3.31-3.42 (m, 3H), 3.73 (t, J = 5.0 Hz, 2H), 4.05 (d, J = 14.8 Hz, 1H), 4.13 (d, J = 14.8 Hz, 1H), 4.28-4.40 (m, 2H), 5.42 (brs, 1H), 7.22-7.31 (m, 5H), 7.49 (d, J = 10.7 Hz, 1H). |

| Example | structural formula | $^1$H-NMR(CDCl$_3$) δ |
|---|---|---|
| 190 | | 1.09 (t, J = 7.0 Hz, 3H), 1.41 (d, J = 6.8 Hz, 3H), 2.33 (s, 3H), 3.31-3.41 (m, 3H), 3.71 (t, J = 5.0 Hz, 2H), 4.05 (d, J = 14.8 Hz, 1H), 4.13 (d, J = 14.8 Hz, 1H), 4.24-4.36 (m, 2H), 5.41 (brs, 1H), 7.07-7.26 (m, 5H), 7.60 (s, 1H). |

Reference Example 55

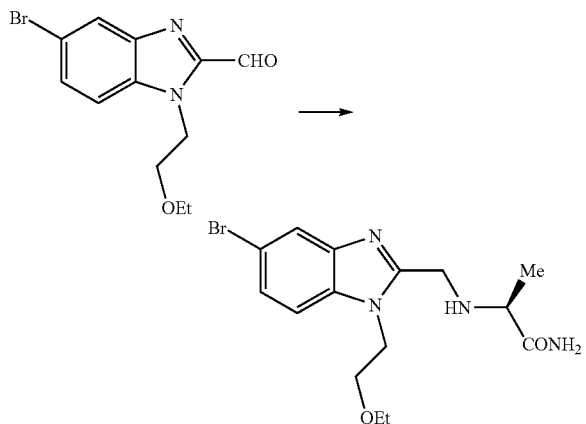

To a solution of the compound (1.4 g, 5.0 mmol) obtained in the same manner as in Reference Examples 9 and 10 from 2-fluoro-5-bromo-nitrobenzene in tetrahydrofuran (30 mL) were added anhydrous sodium sulfate (3.8 g, 26.8 mmol), triethylamine (2.1 ml, 15.4 mmol) and (L)-alaninamide hydrochloride (1.9 g, 15.2 mmol), and the mixture was stirred at room temperature for 30 min. Sodium cyanoborohydride (0.33 g, 5.2 mmol) was added to the reaction mixture, and the mixture was stirred at room temperature overnight. The reaction mixture was poured into saturated aqueous sodium hydrogen carbonate solution, and the mixture was extracted with chloroform. The organic layer was washed with saturated brine, dried over sodium sulfate, and concentrated. The residue was purified by silica gel column (dichloromethane:methanol=99:1-95:5) to give the object product (0.89 g, 51%).

Reference Example 56

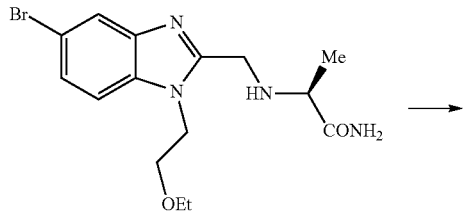

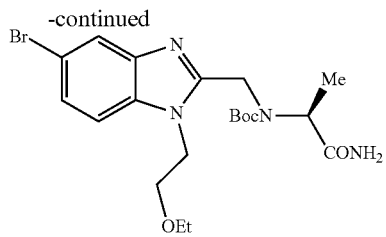

To a solution of the compound (0.48 g, 1.3 mmol) obtained in Reference Example 55 in dichloroethane (10 mL) were added di-tert-butyl bicarbonate (1.4 g, 6.5 mmol) and diisopropylethylamine (0.33 ml, 1.95 mmol), and the mixture was stirred at 80° C. for 14 hr. Dichloromethane was added to the reaction mixture, and the mixture was washed with water and saturated brine. The organic layer was dried over sodium sulfate, and concentrated. The residue was purified by silica gel column (dichloromethane:methanol=99:1-97:3) to give the object product (500 mg, 82%).

Reference Example 57

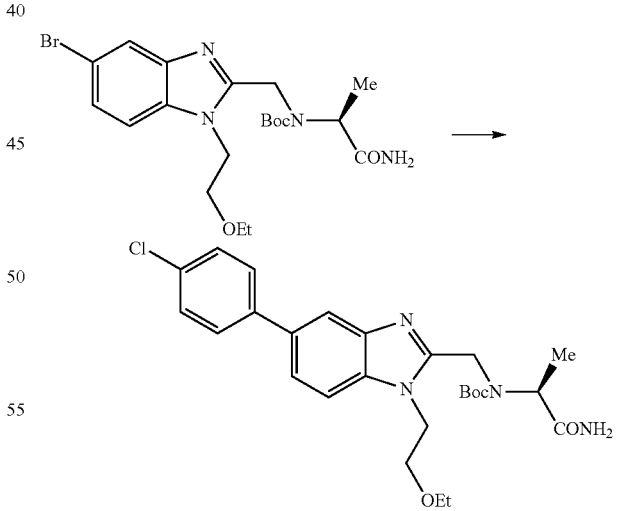

To a solution (3:1, 4 mL) of the compound (50 mg, 0.11 mmol) obtained in Reference Example 56 in aqueous acetonitrile were added 4-chlorophenylboranic acid (34 mg, 0.22 mmol), 3 mol/L aqueous sodium hydrogen carbonate solution (90 μl) and tetrakis(triphenylphosphine)palladium (13 mg, 0.00112 mmol), and the mixture was stirred at 85° C. for 5 hr under an argon atmosphere. The reaction mixture was filtered through celite, and the filtrate was concentrated. Ethyl acetate and saturated aqueous sodium hydrogen carbonate solution were added to partition the residue. The organic layer was washed with water, dried and concentrated. The residue was purified by silica gel column (ethyl acetate alone) to give the object product (48 mg, 90%).

Example 191

N²-{[5-(4-chlorophenyl)-1-(2-ethoxyethyl)-1H-benzimidazol-2-yl]methyl}-L-alaninamide hydrochloride

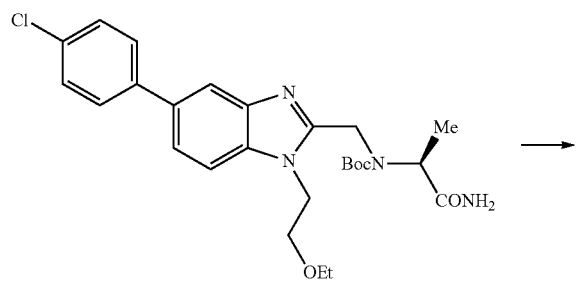

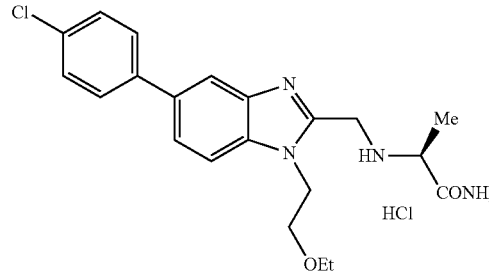

A solution (3 mL) of the compound (48 mg, 0.10 mmol) obtained in Reference Example 57 in hydrochloric acid-dioxane was stirred at room temperature for 1 hr. The reaction mixture was concentrated, and the resulting powder was washed with diethyl ether to give the object product (25 mg, 76%).

Example 192

N²-{[1-(2-ethoxyethyl)-5-(4-methoxyphenyl)-1H-benzimidazol-2-yl]methyl}-L-alaninamide trifluoroacetate

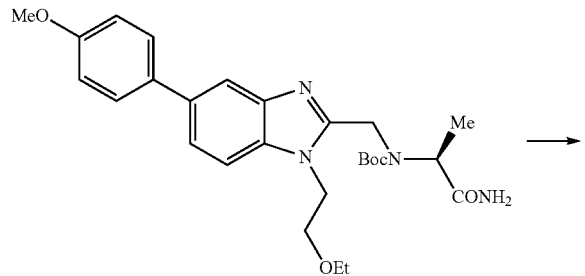

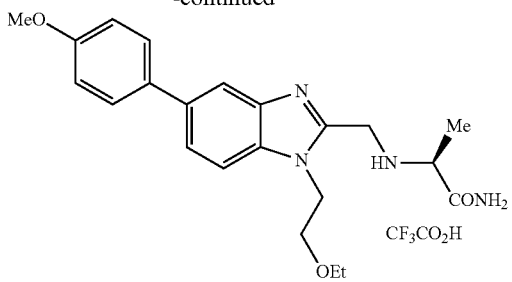

To a solution (3 mL) of the compound (62 mg, 0.13 mmol) obtained in the above-mentioned Reference Example in dichloromethane was added trifluoroacetic acid (0.3 ml) under ice-cooling. The mixture was allowed to warm to room temperature and stirred for 1 hr. The reaction mixture was concentrated and crystallized from diethyl ether to give the object product (48 mg, 76%).

Example 193-208

The compounds shown in Table 32 were prepared according to the methods described in the above-mentioned Reference Examples and Examples or methods analogous thereto.

The compounds were identified by LC/MS spectrum and retention time according to any of the following methods.

Analysis Conditions 1 detection instrument: LCMS/MS API2000 (manufactured by Applied Biosystems)

column: Phenomenex Gemini C18 4.6×50 mm, 5 μm detection wavelength: 220 nm, 260 nm flow rate: 1.2 mL/min elution solvent composition: SOLUTION A: 0.05% aqueous TFA solution, 0.05% aqueous HCOOH solution or 10 mM aqueous ammonium acetate solution, SOLUTION B: acetonitrile gradient: 0-0.01 min B 10%, 0.01-1.50 min B 10% to 30%, 1.50-3.00 min B 30% to 90%, 3.00-4.00 min B 90%, 4.00-5.00 min B 90% to 10%

Analysis Conditions 2 detection instrument: LCMS/MS API2000 (manufactured by Applied Biosystems)

column: Phenomenex Gemini C18 4.6×50 mm, 5 μm detection wavelength: 220 nm, 260 nm flow rate: 1 mL/min elution solvent composition: SOLUTION A: 0.05% aqueous TFA solution, 0.05% aqueous HCOOH solution or 10 mM aqueous ammonium acetate solution, SOLUTION B: acetonitrile gradient: 0-0.01 min B 5%, 0.01-1.00 min B 5%, 1.00-7.00 min B 5% to 50%, 7.00-10.00 min B 50% to 90%, 10.00-11.00 min B 90%, 11.00-12.00 min B 90% to 5%

TABLE 32

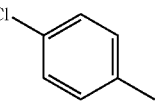

| Example | R | salt | molecular weight | m/e | retention time | analysis conditions |
|---|---|---|---|---|---|---|
| 191 | 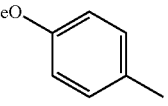 | HCl | 400.1666 | 401.4 | 2.74 | analysis conditions 1 MeCN-TFA |
| 192 | 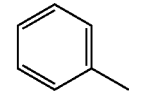 | CF$_3$CO$_2$H | 396.2161 | 397.4 | 2.61 | analysis conditions 1 MeCN-TFA |
| 193 | 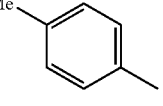 | HCl | 366.2056 | 367.4 | 3.86 | analysis conditions 1 MeCN-TFA |
| 194 | 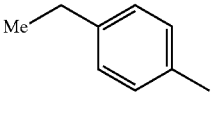 | CF$_3$CO$_2$H | 380.2212 | 381.4 | 6.29 | analysis conditions 2 MeCN-TFA |
| 195 | 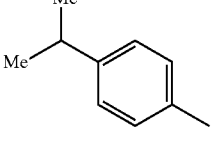 | HCl | 394.2369 | 395.4 | 2.77 | analysis conditions 1 MeCN-TFA |
| 196 | 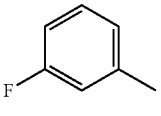 | HCl | 408.2525 | 409.4 | 2.84 | analysis conditions 1 MeCN-TFA |
| 197 | 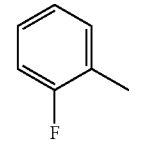 | HCl | 384.1962 | 385.2 | 5.94 | analysis conditions 2 MeCN-TFA |
| 198 | 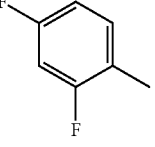 | HCl | 384.1962 | 385.2 | 5.94 | analysis conditions 2 MeCN-TFA |
| 199 | 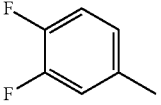 | HCl | 402.1867 | 403.2 | 6.1 | analysis conditions 2 MeCN-TFA |
| 200 | | CF$_3$CO$_2$H | 402.1867 | 403.4 | 2.75 | analysis conditions 1 MeCN-TFA |

TABLE 32-continued

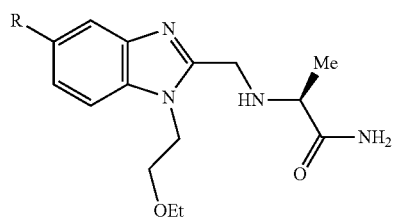

| Example | R | salt | molecular weight | m/e | retention time | analysis conditions |
|---|---|---|---|---|---|---|
| 201 | 3,4,5-trifluorophenyl | HCl | 420.1773 | 421.4 | 2.76 | analysis conditions 1 MeCN-TFA |
| 202 | 2,4,5-trifluorophenyl | HCl | 420.1773 | 421.2 | 6.25 | analysis conditions 1 MeCN-TFA |
| 203 | 4-EtO-phenyl | HCl | 410.2318 | 411.4 | 2.7 | analysis conditions 1 MeCN-TFA |
| 204 | 4-F3CO-phenyl | CF3CO2H | 450.1879 | 451.2 | 2.78 | analysis conditions 1 MeCN-TFA |
| 205 | 4-F3C-phenyl | CF3CO2H | 434.193 | 435.4 | 2.79 | analysis conditions 1 MeCN-TFA |
| 206 | 3,4,5-trifluorophenyl | HCl | 420.1773 | 421.2 | 2.71 | analysis conditions 1 MeCN-TFA |
| 207 | 3-pyridyl | HCl | 367.2008 | 368.6 | 5.99 | analysis conditions 2 MeCN-TFA |
| 208 | 4-NC-phenyl | HCl | 391.2008 | 392.2 | 5.63 | analysis conditions 2 MeCN-TFA |

Reference Example 58

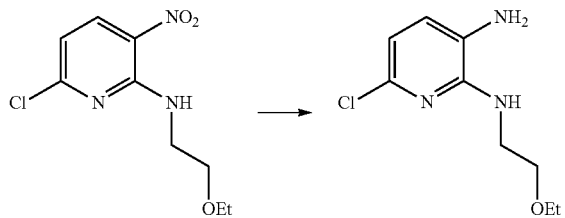 [SMILES: CCOCCNc1nc(Cl)ccc1[N+](=O)[O-] ; CCOCCNc1nc(Cl)ccc1N]

To a solution (25 mL) of iron (3.7 g, 66 mmol) and ammonium chloride (1.04 g, 19 mmol) in a mixed solvent (3:2:1) of tetrahydrofuran-methanol-water was added dropwise a solution (25 mL) of the compound (1.7 g, 6.9 mmol) obtained in Reference Example 18 in a mixed solvent (3:2:1) of tetrahydrofuran-methanol-water at 70° C. After 1.5 hr, the mixture was allowed to cool to room temperature, and the reaction mixture was filtered through celite. The filtrate was concentrated, water was added thereto, and the mixture was extracted with ethyl acetate. The organic layer was washed with water, dried and concentrated to give the object product (1.32 g, 89%). The product was used for the next reaction without purification.

Reference Example 59

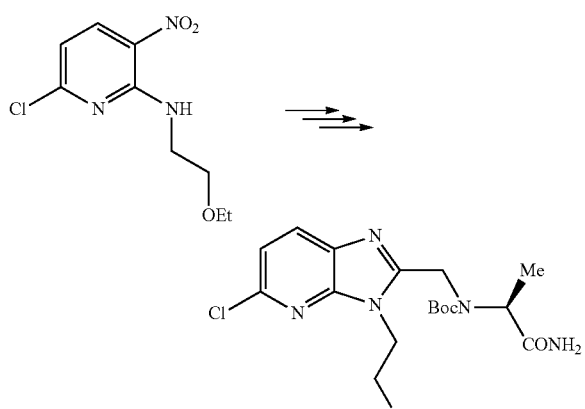

The object product was obtained in the same manner as in Reference Examples 4, 5, 55 and 56.

Reference Example 60

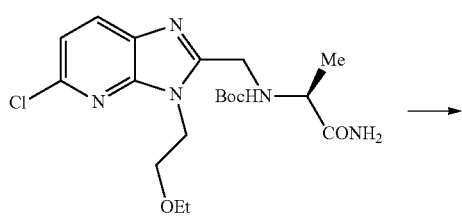

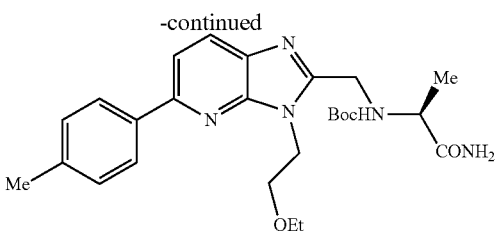

To a solution of the compound (60 mg, 0.14 mmol) obtained in Reference Example 59 and 4-methylphenylboronic acid (38 mg, 0.28 mmol) in n-butanol (2 mL) were added potassium phosphate (60 mg, 0.28 mmol), palladium acetate (3.2 mg, 0.014 mmol) and S-phos (11.6 mg, 0.0038 mmol), and the mixture was stirred at 100° C. for 14 hr under an argon atmosphere. After cooling, the reaction mixture was filtered through celite, and washed with methanol. The filtrate was concentrated, ethyl acetate was added thereto, and the mixture was washed with saturated aqueous sodium hydrogen carbonate solution and saturated brine, dried and concentrated. The residue was purified by silica gel column (ethyl acetate:hexane=65:35) to give the object product (43 mg, 52%).

Example 209

$N^2$-{[3-(2-ethoxyethyl)-5-(4-methylphenyl)-3H-imidazo[4,5-b]pyridin-2-yl]methyl}-L-alaninamide hydrochloride

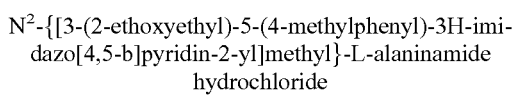

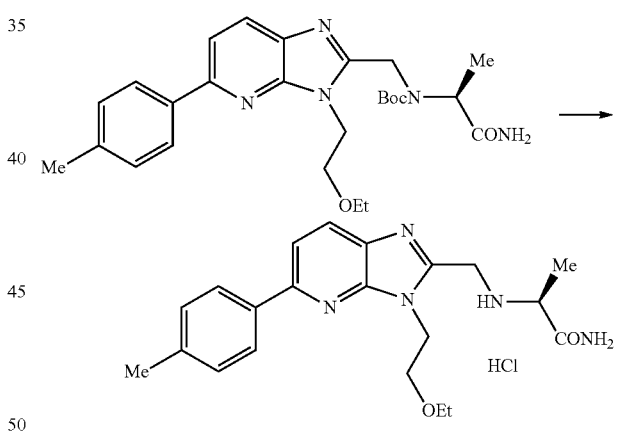

To a solution of the compound (34 mg) obtained in Reference Example 60 in dioxane (1 mL) was added 4 mol/L hydrochloric acid-dioxane (2 mL) under ice-cooling. The mixture was allowed to warm to room temperature, and stirred for 10 hr. The reaction mixture was concentrated, and the resulting powder was washed with diethyl ether to give the object product (28 mg, 95%).

Examples 210-226

The compounds shown in Table 33 were prepared according to the methods described in the above-mentioned Reference Examples and Examples or methods analogous thereto.
The compounds were identified by LC/MS spectrum and retention time under the conditions similar to those described above.

TABLE 33

[Structure: R-substituted imidazo[4,5-b]pyridine with N-CH2CH2OEt group, and -CH2-NH-CH(Me)-C(=O)-NH2 side chain]

| Example | R | salt | molecular weight | m/e | retention time | analysis conditions |
|---|---|---|---|---|---|---|
| 209 | 4-Me-C6H4- | HCl | 381.2165 | 382.3 | 6.15 | analysis conditions 2 MeCN-TFA |
| 210 | C6H5- | HCl | 367.2008 | 368.5 | 3.04 | analysis conditions 1 MeCN—NH4OAc |
| 211 | 4-Et-C6H4- | HCl | 395.2321 | 396.4 | 2.79 | analysis conditions 1 MeCN-TFA |
| 212 | 4-iPr-C6H4- | HCl | 409.2478 | 410.2 | 2.86 | analysis conditions 1 MeCN-TFA |
| 213 | 4-F-C6H4- | HCl | 385.1914 | 386.4 | 3.12 | analysis conditions 1 MeCN—NH4OAc |
| 214 | 3-F-C6H4- | HCl | 385.1914 | 386.2 | 2.63 | analysis conditions 1 MeCN-TFA |
| 215 | 2-F-C6H4- | HCl | 385.1914 | 386.2 | 2.63 | analysis conditions 1 MeCN-TFA |
| 216 | 2,4-di-F-C6H3- | HCl | 403.182 | 404.2 | 2.6 | analysis conditions 1 MeCN-TFA |
| 217 | 3,4-di-F-C6H3- | HCl | 403.182 | 404.4 | 2.71 | analysis conditions 1 MeCN-TFA |
| 218 | 3,4,5-tri-F-C6H2- | HCl | 421.1726 | 422.2 | 2.71 | analysis conditions 1 MeCN-TFA |

TABLE 33-continued

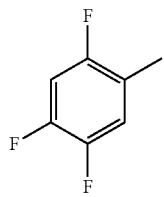

| Example | R | salt | molecular weight | m/e | retention time | analysis conditions |
|---|---|---|---|---|---|---|
| 219 | 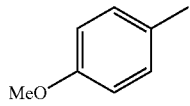 2,4,5-trifluorophenyl | HCl | 421.1726 | 422.1 | 6.25 | analysis conditions 2 MeCN-TFA |
| 220 | 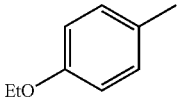 4-MeO-phenyl | HCl | 397.2114 | 398.2 | 2.67 | analysis conditions 1 MeCN-TFA |
| 221 | 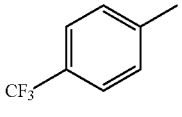 4-EtO-phenyl | HCl | 411.227 | 412.4 | 6.22 | analysis conditions 2 MeCN-TFA |
| 222 | 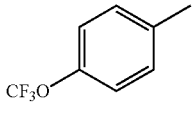 4-CF3-phenyl | HCl | 435.1882 | 436.6 | 2.79 | analysis conditions 1 MeCN-TFA |
| 223 | 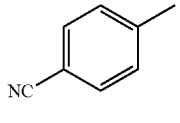 4-CF3O-phenyl | HCl | 451.1831 | 452.2 | 6.85 | analysis conditions 2 MeCN-TFA |
| 224 | 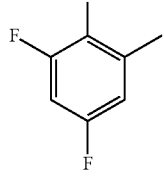 4-NC-phenyl | HCl | 392.1961 | 393.4 | 2.61 | analysis conditions 1 MeCN-TFA |
| 225 | 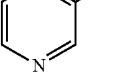 2,4,6-trifluorophenyl | HCl | 421.1726 | 422 | 2.65 | analysis conditions 1 MeCN-TFA |
| 226 | pyridin-3-yl | HCl | 368.1961 | 369.6 | 5.34 | analysis conditions 2 MeCN-TFA |

Example 227-237

The compounds of Examples 227-237 shown in Table 34 and Table 35 were prepared in the same manner as in Reference Examples 18-20 and Example 79.

The compounds were identified by LC/MS spectrum and retention time under the conditions similar to those described above.

TABLE 34

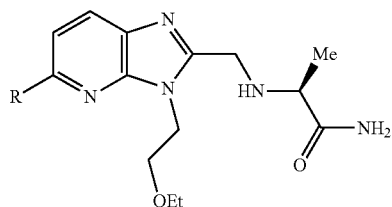

| Example | R | molecular weight | m/e | retention time | analysis conditions |
|---|---|---|---|---|---|
| 227 | 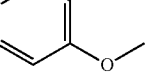 | 401.1863 | 402 | 2.64 | analysis conditions 1 MeCN-TFA |
| 228 |  | 417.1568 | 418 | 2.72 | analysis conditions 1 MeCN-TFA |
| 229 |  | 397.2114 | 398.2 | 2.67 | analysis conditions 1 MeCN-TFA |
| 230 | 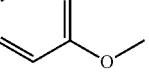 | 419.1769 | 420.2 | 2.68 | analysis conditions 1 MeCN-TFA |
| 231 |  | 419.1769 | 420.2 | 2.67 | analysis conditions 1 MeCN-TFA |
| 232 | 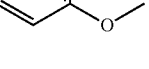 | 437.1675 | 438 | 2.68 | analysis conditions 1 MeCN-TFA |

TABLE 35

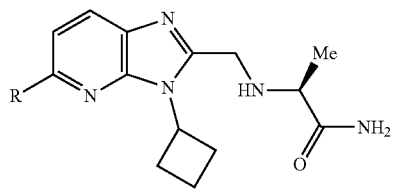

| Example | R | molecular weight | m/e | retention time | analysis conditions |
|---|---|---|---|---|---|
| 233 | 4-F, 3-OMe-phenyl | 383.1758 | 384.2 | 2.71 | analysis conditions 1 MeCN-TFA |
| 234 | 4-Me, 3-OMe-phenyl | 379.2008 | 380.4 | 2.78 | analysis conditions 1 MeCN-TFA |
| 235 | 3,4-diF, 5-OMe-phenyl | 401.1663 | 402.2 | 2.71 | analysis conditions 1 MeCN-TFA |
| 236 | 2,4-diF, 3-OMe-phenyl | 401.1663 | 402.2 | 2.72 | analysis conditions 1 MeCN-TFA |
| 237 | 2,3,4-triF, 5-OMe-phenyl | 419.1569 | 419.9 | 2.75 | analysis conditions 1 MeCN-TFA |

The compounds shown in Tables 36-38 can be prepared according to the methods described in the above-mentioned Reference Examples and Examples or methods analogous thereto.

TABLE 36

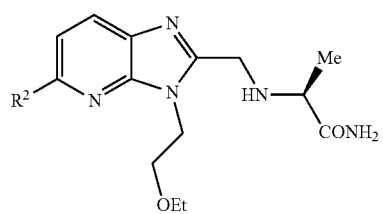

| No. | R² |
|---|---|
| 1 | 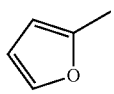 |

TABLE 36-continued

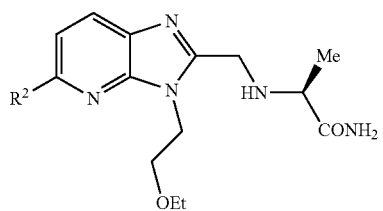

| No. | R² |
|---|---|
| 2 | 4-Cl-phenyl |
| 3 | 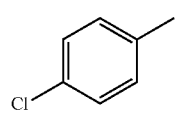 |

TABLE 37
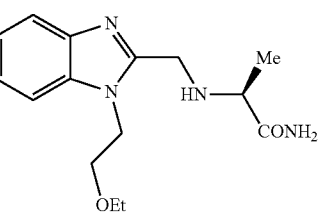
| No. | R² |
|---|---|
| 4 | 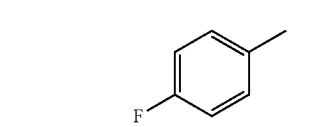 |
| 5 | 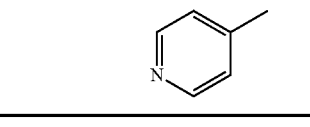 |
| 6 | 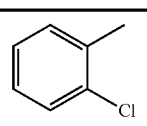 |
TABLE 38
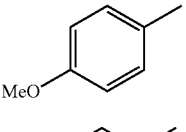
| No. | R² |
|---|---|
| 7 | 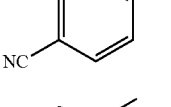 |
| 8 | 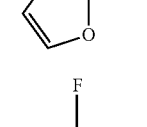 |
| 9 | 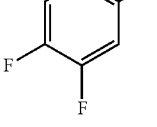 |
| 10 | 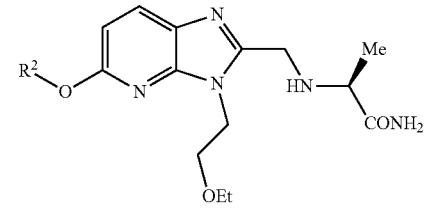 |
| 11 | 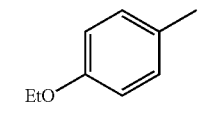 |
TABLE 38-continued
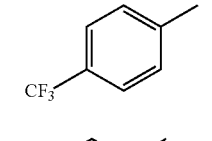
| No. | R² |
|---|---|
| 12 | 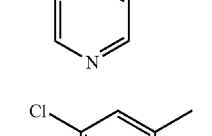 |
| 13 | 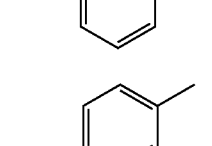 |
| 14 | 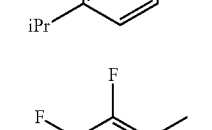 |
| 15 | 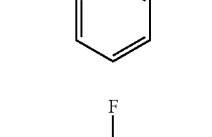 |
| 16 |  |
| 17 | 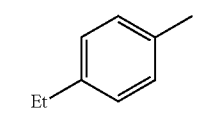 |
| 18 | 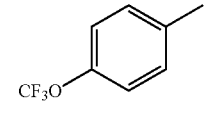 |
| 19 | 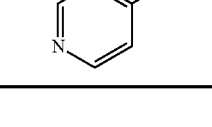 |
| 20 | |
| 21 | |

Experimental Example 1

Inhibition Experiment of TTX Resistant Na Channel on Human SNS Gene-Expressing Cell Human SNS gene-expressing cell is obtained by incorporating human SNS gene into Chinese hamster ovary cell (CHO-K1) and allowing stable expression. Since CHO-K1 cell does not inherently have a TTX resistant Na channel component, TTX resistant Na channel component of human SNS gene-expressing cell is SNS and the compound of the present invention is considered an SNS inhibitor.

1) Construction of Human SNS-Expressing Cell and Confirmation of Expression of SNS Function Full-length human SNS α subunit gene was incorporated into an expression plasmid (pcDNA3.1Zeo(+)) having a Zeocin resistance gene, and full-length Annexin II light chain gene was introduced into an expression plasmid (pcDNA3.1(+)) containing a Neomycin resistance gene. These two genes were simultaneously introduced into CHO-K1 cell by using lipofectamine 2000, cultured in F-12 medium containing Neomycin and Zeocin, and a cell resistant to the both drugs, namely, a cell harboring the both genes, was selected. The two drug-resistance strain was subjected to limiting dilution twice, and the SNS gene-incorporating cell was cloned. Transgenic SNS was confirmed by RT-PCR, a TTX resistant component responsive to Na channel stimulation was detected by using a membrane potential sensitive fluorescent indicator, and functional expression of SNS was confirmed.

2) Pharmacological Effect on TTX Resistant Na Channel of Human SNS Gene-Expressing Cell Using the human SNS-expressing cell obtained in the aforementioned 1, the SNS inhibitory action of the compound of the present invention was evaluated. To be specific, a test compound was added in advance to a human SNS-expressing cell, veratridine (50 μM), an Na channel stimulant, was added about 30 min later in the presence of TTX (1 μM), the membrane potencial was increased via the TTX resistant Na channel, and the suppressive action on the membrane potencial increase of the test compound was evaluated.

3) Pharmacological Evaluation Method

SNS inhibitory rate of the test compound was determined by the following calculation formula.

SNS inhibitory rate (%)=100×[(peak value by veratridine stimulation alone without test compound)−(peak value by veratridine stimulation with test compound)]/[(peak value by veratridine stimulation alone without test compound)−(standard value without stimulation)]

4) Test Results

The compounds obtained in the Examples were evaluated for an inhibitory action (SNS inhibitory rate) on TTX resistant Na channel of human SNS-expressing cell. As a result, the compound of the present invention was observed to show an SNS inhibitory action. The SNS inhibitory rate (%) when the compound concentration was 12.5 μM is shown in Tables 39-47.

TABLE 39

| compound | SNS inhibitory rate (%) |
| --- | --- |
| Example 1 | 45.8 |
| Example 2 | 8.4 |
| Example 3 | 12.9 |
| Example 4 | 66.8 |
| Example 5 | 59.3 |

TABLE 39-continued

| compound | SNS inhibitory rate (%) |
| --- | --- |
| Example 6 | 77.8 |
| Example 7 | 83.1 |
| Example 8 | 90.4 |
| Example 9 | 28.9 |
| Example 10 | 16.3 |
| Example 11 | 63.0 |
| Example 12 | 17.0 |
| Example 13 | 29.8 |
| Example 14 | 16.4 |
| Example 15 | 95.7 |
| Example 16 | 96.2 |
| Example 17 | 89.3 |
| Example 18 | 14.2 |
| Example 19 | 100 |
| Example 20 | 7.2 |
| Example 21 | 100 |
| Example 22 | 16.4 |
| Example 23 | 0.8 |
| Example 24 | 5.8 |
| Example 25 | 0.0 |
| Example 26 | 26.6 |
| Example 27 | 78.2 |
| Example 28 | 27.4 |
| Example 29 | 27.0 |
| Example 30 | 31.5 |

TABLE 40

| compound | SNS inhibitory rate (%) |
| --- | --- |
| Example 31 | 92.1 |
| Example 32 | 91.2 |
| Example 33 | 32.9 |
| Example 34 | 6.7 |
| Example 35 | 10.8 |
| Example 36 | 0.4 |
| Example 37 | 42.3 |
| Example 38 | 48.8 |
| Example 39 | 48.8 |
| Example 40 | 95.8 |
| Example 41 | 99.7 |
| Example 42 | 76.7 |
| Example 43 | 61.0 |
| Example 44 | 84.9 |
| Example 45 | 40.6 |
| Example 46 | 95.5 |
| Example 47 | 86.6 |
| Example 48 | 96.7 |
| Example 49 | 94.8 |
| Example 50 | 86.8 |
| Example 51 | 90.5 |
| Example 52 | 89.7 |
| Example 53 | 94.0 |
| Example 54 | 95.7 |
| Example 55 | 89.4 |
| Example 56 | 82.2 |
| Example 57 | 87.6 |
| Example 58 | 71.2 |
| Example 59 | 54.8 |
| Example 60 | 75.7 |

TABLE 41

| compound | SNS inhibitory rate (%) |
| --- | --- |
| Example 61 | 26.1 |
| Example 62 | 93.8 |
| Example 63 | 9.2 |
| Example 64 | 82.7 |
| Example 65 | 47.8 |

TABLE 41-continued

| compound | SNS inhibitory rate (%) |
|---|---|
| Example 66 | 16.8 |
| Example 67 | 30.8 |
| Example 68 | 16.0 |
| Example 69 | 22.3 |
| Example 70 | 11.2 |
| Example 71 | 73.7 |
| Example 72 | 7.3 |
| Example 73 | 8.0 |
| Example 74 | 58.2 |
| Example 75 | 0.0 |
| Example 76 | 18.8 |
| Example 77 | 16.0 |
| Example 78 | 22.2 |
| Example 79 | 3.5 |
| Example 80 | 2.5 |
| Example 81 | 69.1 |
| Example 82 | 30.7 |
| Example 83 | 0.0 |
| Example 84 | 76.8 |
| Example 85 | 24.9 |
| Example 86 | 8.3 |
| Example 87 | 90.1 |
| Example 88 | 83.5 |
| Example 89 | 83.0 |
| Example 90 | 96.1 |

TABLE 42

| compound | SNS inhibitory rate (%) |
|---|---|
| Example 91 | 76.4 |
| Example 92 | 66.7 |
| Example 93 | 82.1 |
| Example 94 | 63.9 |
| Example 95 | 26.8 |
| Example 96 | 84.8 |
| Example 97 | 82.4 |
| Example 98 | 69.8 |
| Example 99 | 65.4 |
| Example 100 | 72.1 |
| Example 101 | 85.2 |
| Example 102 | 96.3 |
| Example 103 | 87.9 |
| Example 104 | 83.6 |
| Example 105 | 75.1 |
| Example 106 | 86.4 |
| Example 107 | 83.7 |
| Example 108 | 85.3 |

TABLE 43

| compound | SNS inhibitory rate (%) |
|---|---|
| Example 109 | 89.3 |
| Example 110 | 9.8 |
| Example 111 | 88.4 |
| Example 112 | 0 |
| Example 113 | 64.7 |
| Example 114 | 6.5 |
| Example 115 | 3.5 |
| Example 116 | 33.2 |
| Example 117 | 78.8 |
| Example 118 | 64.5 |
| Example 119 | 87.2 |
| Example 120 | 92.4 |
| Example 121 | 94.3 |
| Example 122 | 100 |
| Example 123 | 96.8 |
| Example 124 | 87.8 |
| Example 125 | 95.9 |

TABLE 43-continued

| compound | SNS inhibitory rate (%) |
|---|---|
| Example 126 | 56.9 |
| Example 127 | 93.9 |
| Example 128 | 85 |
| Example 129 | 90.3 |
| Example 130 | 42.1 |
| Example 131 | 55.9 |
| Example 132 | 86.4 |
| Example 133 | 91.7 |
| Example 134 | 95.7 |
| Example 135 | 57.8 |
| Example 136 | 28.7 |
| Example 137 | 90.7 |
| Example 138 | 93.1 |

TABLE 44

| compound | SNS inhibitory rate (%) |
|---|---|
| Example 139 | 96 |
| Example 140 | 97.5 |
| Example 141 | 90.3 |
| Example 142 | 47.9 |
| Example 143 | 27.7 |
| Example 144 | 6.1 |
| Example 145 | 1.3 |
| Example 146 | 19.7 |
| Example 147 | 23.5 |
| Example 148 | 17 |
| Example 149 | 30.6 |
| Example 150 | 45.6 |
| Example 151 | 26.6 |
| Example 152 | 8.9 |
| Example 153 | 28.5 |
| Example 154 | 11.2 |
| Example 155 | 86.1 |
| Example 156 | 71.2 |
| Example 157 | 89.9 |
| Example 158 | 86.1 |
| Example 159 | 96.1 |
| Example 160 | 97 |
| Example 161 | 76.2 |
| Example 162 | 67.3 |
| Example 163 | 36.5 |
| Example 164 | 3.7 |
| Example 165 | 100 |
| Example 166 | 62.7 |
| Example 167 | 82.8 |
| Example 168 | 20.2 |

TABLE 45

| compound | SNS inhibitory rate (%) |
|---|---|
| Example 169 | 68.1 |
| Example 170 | 14.2 |
| Example 171 | 38.3 |
| Example 172 | 50.9 |
| Example 173 | 27.1 |
| Example 174 | 33.4 |
| Example 175 | 5.9 |
| Example 176 | 68.8 |
| Example 177 | 22.5 |
| Example 178 | 16 |
| Example 179 | 67.4 |
| Example 180 | 4.5 |
| Example 181 | 0 |
| Example 182 | 0 |
| Example 183 | 72.3 |
| Example 184 | 87.9 |
| Example 185 | 64.6 |

TABLE 45-continued

| compound | SNS inhibitory rate (%) |
| --- | --- |
| Example 186 | 55.6 |
| Example 187 | 53.3 |
| Example 188 | 87 |
| Example 189 | 97.7 |
| Example 190 | 34.3 |
| Example 191 | 23.3 |
| Example 192 | 11.9 |
| Example 193 | 22.3 |
| Example 194 | 19.7 |
| Example 195 | 20.1 |
| Example 196 | 23 |
| Example 197 | 9.3 |
| Example 198 | 10.2 |

TABLE 46

| compound | SNS inhibitory rate (%) |
| --- | --- |
| Example 199 | 14.7 |
| Example 200 | 22.4 |
| Example 201 | 11.1 |
| Example 202 | 26 |
| Example 203 | 18.4 |
| Example 204 | 0 |
| Example 205 | 24.2 |
| Example 206 | 14.5 |
| Example 207 | 7 |
| Example 208 | 0 |
| Example 209 | 6.5 |
| Example 210 | 2.1 |
| Example 211 | 9.5 |
| Example 212 | 20.6 |
| Example 213 | 8.1 |
| Example 214 | 0.2 |
| Example 215 | 12.4 |
| Example 216 | 0.7 |
| Example 217 | 3.2 |
| Example 218 | 12.5 |
| Example 219 | 9.7 |
| Example 220 | 12.2 |
| Example 221 | 22 |
| Example 222 | 10.1 |
| Example 223 | 0 |
| Example 224 | 0 |
| Example 225 | 25.1 |
| Example 226 | 14 |
| Example 227 | 20.4 |
| Example 228 | 31 |

TABLE 47

| compound | SNS inhibitory rate (%) |
| --- | --- |
| Example 229 | 10.1 |
| Example 230 | 33.2 |
| Example 231 | 17.9 |
| Example 232 | 16.1 |
| Example 233 | 49.9 |
| Example 234 | 94.3 |
| Example 235 | 100 |
| Example 236 | 71 |
| Example 237 | 100 |

INDUSTRIAL APPLICABILITY

The novel bicyclic heterocyclic compound of the present invention can be used as a superior drug for the treatment or prophylaxis of pathology in which SNS is involved, specifically, diseases such as neuropathic pain, nociceptive pain, dysuria, multiple sclerosis and the like.

The invention claimed is:
1. A compound represented by formula (1):

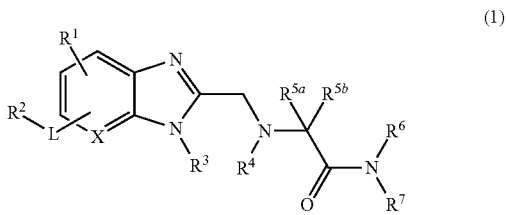

wherein
$R^1$ is a hydrogen atom, a halogen atom, an alkyl group having 1 to 6 carbon atoms, a haloalkyl group having 1 to 6 carbon atoms, an alkoxy group having 1 to 6 carbon atoms or a haloalkoxy group having 1 to 6 carbon atoms ($R^1$ can substitute the benzene ring or pyridine ring at any substitutable position thereon), L is a single bond, —O— or —CH$_2$O— (L can substitute the benzene ring or pyridine ring at any substitutable position thereon), $R^2$ is a substituted or unsubstituted 6- to 10-membered aryl group, or a substituted or unsubstituted 5- to 10-membered aromatic heterocyclic group, X is a carbon atom or a nitrogen atom, $R^3$ is a substituted or unsubstituted alkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, or a substituted or unsubstituted 5- to 10-membered unsaturated aliphatic heterocyclic group, $R^4$ is a hydrogen atom, a substituted or unsubstituted alkyl group having 1 to 6 carbon atoms, or a substituted or unsubstituted 3- to 8-membered cycloalkyl group, $R^{5a}$ and $R^{5b}$ are each independently a hydrogen atom, or a substituted or unsubstituted alkyl group having 1 to 6 carbon atoms, or $R^4$ and $R^{5a}$ are optionally bonded to form, together with the nitrogen atom that $R^4$ is bonded to, a 4- to 8-membered saturated nitrogen-containing aliphatic heterocycle (in this case, $R^{5b}$ is a hydrogen atom), $R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted alkenyl group having 2 to 6 carbon atoms, a substituted or unsubstituted alkynyl group having 2 to 6 carbon atoms, a substituted or unsubstituted 3- to 8-membered cycloalkyl group, a substituted or unsubstituted 4- to 8-membered cycloalkenyl group, a substituted or unsubstituted 4- to 8-membered saturated aliphatic heterocyclic group, a substituted or unsubstituted 5- to 10-membered unsaturated aliphatic heterocyclic group, a substituted or unsubstituted 6- to 10-membered aryl group, or a substituted or unsubstituted 5- to 10-membered aromatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms), or a pharmaceutically acceptable salt thereof.

2. The compound of claim 1, which is represented by formula (2):

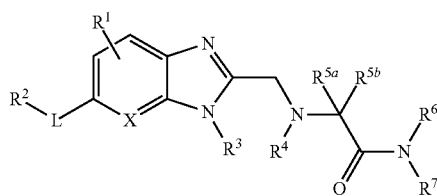

or a pharmaceutically acceptable salt thereof.

3. The compound of claim 1, which is represented by formula (3):

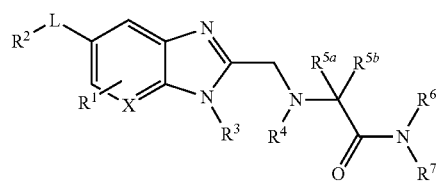

or a pharmaceutically acceptable salt thereof.

4. The compound of claim 1, wherein $R^2$ is a substituted or unsubstituted phenyl group, or a pharmaceutically acceptable salt thereof.

5. The compound of claim 1, wherein $R^3$ is a substituted or unsubstituted alkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, or a pharmaceutically acceptable salt thereof.

6. The compound of claim 1, wherein $R^6$ and $R^7$ are each independently a hydrogen atom, a substituted or unsubstituted alkyl group having 1 to 6 carbon atoms, a haloalkyl group having 1 to 6 carbon atoms, a substituted or unsubstituted 3- to 8-membered cycloalkyl group, a substituted or unsubstituted 4- to 8-membered saturated aliphatic heterocyclic group, or a substituted or unsubstituted 5- to 10-membered unsaturated aliphatic heterocyclic group, or $R^6$ and $R^7$ are optionally bonded to form, together with the nitrogen atom that they are bond to, a substituted or unsubstituted 4- to 8-membered saturated nitrogen-containing aliphatic heterocycle, or a substituted or unsubstituted 5- to 10-membered unsaturated nitrogen-containing aliphatic heterocycle (the saturated or unsaturated nitrogen-containing aliphatic heterocycle contains 0 to 2 oxygen atoms, 0 to 2 sulfur atoms and 1 to 3 nitrogen atoms), or a pharmaceutically acceptable salt thereof.

7. The compound of claim 1, wherein $R^4$ is a hydrogen atom, or a substituted or unsubstituted alkyl group having 1 to 6 carbon atoms, or a pharmaceutically acceptable salt thereof.

8. The compound of claim 1, wherein $R^{5a}$ and $R^{5b}$ are each independently a hydrogen atom, or a substituted or unsubstituted alkyl group having 1 to 6 carbon atoms, or a pharmaceutically acceptable salt thereof.

9. The compound of claim 1, wherein X is a carbon atom, or a pharmaceutically acceptable salt thereof.

10. The compound of claim 1, wherein $R^1$ is a hydrogen atom or a halogen atom, or a pharmaceutically acceptable salt thereof.

11. The compound of claim 1, wherein L is a single bond, or a pharmaceutically acceptable salt thereof.

12. The compound of claim 1, wherein L is —O—, or a pharmaceutically acceptable salt thereof.

13. The compound of claim 1, wherein L is —CH$_2$O—, or a pharmaceutically acceptable salt thereof.

14. $N^2$-{[1-(2-ethoxyethyl)-6-(4-fluorophenoxy)-1H-benzimidazol-2-yl]methyl}glycinamide,
   $N^2$-{[1-(2-ethoxyethyl)-6-(4-fluorophenoxy)-1H-benzimidazol-2-yl]methyl}-2-methylalaninamide,
   $N^2$-{[1-cyclopropyl-6-(4-fluorophenoxy)-1H-benzimidazol-2-yl]methyl}-L-alaninamide,
   $N^2$-{[1-cyclobutyl-6-(4-fluorophenoxy)-1H-benzimidazol-2-yl]methyl}-L-alaninamide,
   $N^2$-{[6-(4-chlorophenoxy)-1-(2-ethoxyethyl)-1H-benzimidazol-2-yl]methyl}-L-alaninamide,
   $N^2$-{[6-(4-fluorophenoxy)-1-(2-hydroxy-2-methylpropyl)-1H-benzimidazol-2-yl]methyl}-L-alaninamide,
   $N^2$-{[1-(2-ethoxyethyl)-6-(4-fluorophenoxy)-1H-benzimidazol-2-yl]methyl}-L-alaninamide,
   $N^2$-{[6-(4-fluorophenoxy)-1-(3-methoxypropyl)-1H-benzimidazol-2-yl]methyl}-L-alaninamide,
   $N^2$-{[6-(2-chloro-4-fluorophenoxy)-1-(2-ethoxyethyl)-1H-benzimidazol-2-yl]methyl}-L-alaninamide,
   $N^2$-{[1-ethyl-6-(4-methylphenoxy)-1H-benzimidazol-2-yl]methyl}-L-alaninamide,
   $N^2$-{[6-(2,4-difluorophenoxy)-1-(2-hydroxy-2-methylpropyl)-1H-benzimidazol-2-yl]methyl}-L-alaninamide,
   $N^2$-{[1-(2-ethoxyethyl)-5-fluoro-6-(4-fluorophenyl)-1H-benzimidazol-2-yl]methyl}-L-alaninamide,
   $N^2$-{[1-ethyl-5-fluoro-6-(4-fluorophenyl)-1H-benzimidazol-2-yl]methyl}-L-alaninamide,
   $N^2$-{[1-(3-methoxypropyl)-6-(4-methylphenoxy)-1H-benzimidazol-2-yl]methyl}-L-alaninamide,
   $N^2$-{[6-(4-methylphenoxy)-1-(tetrahydro-2H-pyran-4-yl)-1H-benzimidazol-2-yl]methyl}-L-alaninamide,
   $N^2$-{[5-chloro-1-(2-ethoxyethyl)-6-(4-fluorophenyl)-1H-benzimidazol-2-yl]methyl}-L-alaninamide, or
   $N^2$-{[5-chloro-6-(3,4-difluorophenyl)-1-(2-ethoxyethyl)-1H-benzimidazol-2-yl]methyl}-L-alaninamide,
   or a pharmaceutically acceptable salt thereof.

15. A pharmaceutical composition comprising the compound of claim 1 or a pharmaceutically acceptable salt thereof, and a pharmaceutically acceptable carrier.

16. A method for the treatment of neuropathic pain, nociceptive pain, dysuria, or multiple sclerosis in a patient, which method comprises administering an effective amount of the compound of claim 1 or a pharmaceutically acceptable salt thereof to a patient in need of treatment of neuropathic pain, nociceptive pain, dysuria, or multiple sclerosis, thereby providing treatment of neuropathic pain, nociceptive pain, dysuria, or multiple sclerosis in the patient.

17. The method of claim 16, wherein the neuropathic pain is selected from neuralgia after lumbar operation, diabetic neuropathy, neuralgia after herpes zoster, reflex sympathetic dystrophy, phantom limb pain, spinal cord injury, late stage carcinomatous pain, and prolonged postoperative pain.

18. $N^2$-{[1-(2-ethoxyethyl)-6-(4-fluorophenoxy)-1H-benzimidazol-2-yl]methyl}-2-methylalaninamide, or a pharmaceutically acceptable salt thereof.

19. $N^2$-{[6-(2-chloro-4-fluorophenoxy)-1-(2-ethoxyethyl)-1H-benzimidazol-2-yl]methyl}-L-alaninamide, or a pharmaceutically acceptable salt thereof.

20. $N^2$-{[1-ethyl-6-(4-methylphenoxy)-1H-benzimidazol-2-yl]methyl}-L-alaninamide, or a pharmaceutically acceptable salt thereof.

21. $N^2$-{[1-(3-methoxypropyl)-6-(4-methylphenoxy)-1H-benzimidazol-2-yl]methyl}-L-alaninamide, or a pharmaceutically acceptable salt thereof.

22. $N^2$-{[6-(4-methylphenoxy)-1-(tetrahydro-2H-pyran-4-yl)-1H-benzimidazol-2-yl]methyl}-L-alaninamide, or a pharmaceutically acceptable salt thereof.

23. A pharmaceutical composition comprising the compound of claim 14 or a pharmaceutically acceptable salt thereof, and a pharmaceutically acceptable carrier.

24. The pharmaceutical composition of claim 23, wherein the compound is $N^2$-{[1-(2-ethoxyethyl)-6-(4-fluorophenoxy)-1H-benzimidazol-2-yl]methyl}-2-methylalaninamide, or a pharmaceutically acceptable salt thereof.

25. The pharmaceutical composition of claim 23, wherein the compound is $N^2$-{[6-(2-chloro-4-fluorophenoxy)-1-(2-ethoxyethyl)-1H-benzimidazol-2-yl]methyl}-L-alaninamide, or a pharmaceutically acceptable salt thereof.

26. The pharmaceutical composition of claim 23, wherein the compound is $N^2$-{[1-ethyl-6-(4-methylphenoxy)-1H-benzimidazol-2-yl]methyl}-L-alaninamide, or a pharmaceutically acceptable salt thereof.

27. The pharmaceutical composition of claim 23, wherein the compound is $N^2$-{[1-(3-methoxypropyl)-6-(4-methylphenoxy)-1H-benzimidazol-2-yl]methyl}-L-alaninamide, or a pharmaceutically acceptable salt thereof.

28. The pharmaceutical composition of claim 23, wherein the compound is $N^2$-{[6-(4-methylphenoxy)-1-(tetrahydro-2H-pyran-4-yl)-1H-benzimidazol-2-yl]methyl}-L-alaninamide, or a pharmaceutically acceptable salt thereof.

29. A method for the treatment of neuropathic pain, nociceptive pain, dysuria, or multiple sclerosis in a patient, which method comprises administering an effective amount of the compound of claim 14 or a pharmaceutically acceptable salt thereof to a patient in need of treatment of neuropathic pain, nociceptive pain, dysuria, or multiple sclerosis, thereby providing treatment of neuropathic pain, nociceptive pain, dysuria, or multiple sclerosis in the patient.

30. The method of claim 29, wherein the compound is $N^2$-{[1-(2-ethoxyethyl)-6-(4-fluorophenoxy)-1H-benzimidazol-2-yl]methyl}-2-methylalaninamide, or a pharmaceutically acceptable salt thereof.

31. The method of claim 29, wherein the compound is $N^2$-{[6-(2-chloro-4-fluorophenoxy)-1-(2-ethoxyethyl)-1H-benzimidazol-2-yl]methyl}-L-alaninamide, or a pharmaceutically acceptable salt thereof.

32. The method of claim 29, wherein the compound is $N^2$-{[1-ethyl-6-(4-methylphenoxy)-1H-benzimidazol-2-yl]methyl}-L-alaninamide, or a pharmaceutically acceptable salt thereof.

33. The method of claim 29, wherein the compound is $N^2$-{[1-(3-methoxypropyl)-6-(4-methylphenoxy)-1H-benzimidazol-2-yl]methyl}-L-alaninamide, or a pharmaceutically acceptable salt thereof.

34. The method of claim 29, wherein the compound is $N^2$-{[6-(4-methylphenoxy)-1-(tetrahydro-2H-pyran-4-yl)-1H-benzimidazol-2-yl]methyl}-L-alaninamide, or a pharmaceutically acceptable salt thereof.

35. The method of claim 29, wherein the neuropathic pain is selected from neuralgia after lumbar operation, diabetic neuropathy, neuralgia after herpes zoster, reflex sympathetic dystrophy, phantom limb pain, spinal cord injury, late stage carcinomatous pain, and prolonged postoperative pain.

36. The method of claim 24, wherein the compound is $N^2$-{[1-(2-ethoxyethyl)-6-(4-fluorophenoxy)-1H-benzimidazol-2-yl]methyl}-2-methylalaninamide, or a pharmaceutically acceptable salt thereof.

37. The method of claim 35, wherein the compound is $N^2$-{[6-(2-chloro-4-fluorophenoxy)-1-(2-ethoxyethyl)-1H-benzimidazol-2-yl]methyl}-L-alaninamide, or a pharmaceutically acceptable salt thereof.

38. The method of claim 35, wherein the compound is $N^2$-{[1-ethyl-6-(4-methylphenoxy)-1H-benzimidazol-2-yl]methyl}-L-alaninamide, or a pharmaceutically acceptable salt thereof.

39. The method of claim 35, wherein the compound is $N^2$-{[1-(3-methoxypropyl)-6-(4-methylphenoxy)-1H-benzimidazol-2-yl]methyl}-L-alaninamide, or a pharmaceutically acceptable salt thereof.

40. The method of claim 35, wherein the compound is $N^2$-{[6-(4-methylphenoxy)-1-(tetrahydro-2H-pyran-4-yl)-1H-benzimidazol-2-yl]methyl}-L-alaninamide, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,471,038 B2 |
| APPLICATION NO. | : 13/141301 |
| DATED | : June 25, 2013 |
| INVENTOR(S) | : Tsuboi et al. |

Page 1 of 1

It is certified that error appears in the above-identified patent and that said Letters Patent is hereby corrected as shown below:

IN THE CLAIMS

Claim 36, at column 176, line 26, "The method of claim 24" should read "The method of claim 35"

Signed and Sealed this
Eleventh Day of March, 2014

Michelle K. Lee
*Deputy Director of the United States Patent and Trademark Office*